(12) United States Patent
Montminy et al.

(10) Patent No.: US 8,389,207 B2
(45) Date of Patent: Mar. 5, 2013

(54) METHODS FOR IDENTIFYING CANDIDATE FAT-MOBILIZING AGENTS

(75) Inventors: Marc Montminy, San Diego, CA (US); Jose E. Heredia, Lo Jolla, CA (US); Ling Qi, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 1270 days.

(21) Appl. No.: 11/756,392

(22) Filed: May 31, 2007

(65) Prior Publication Data

US 2008/0014583 A1 Jan. 17, 2008

Related U.S. Application Data

(60) Provisional application No. 60/804,275, filed on Jun. 8, 2006.

(51) Int. Cl.
| | | |
|---|---|---|
| *C12Q 1/00* | (2006.01) | |
| *C12Q 1/68* | (2006.01) | |
| *G01N 33/567* | (2006.01) | |
| *G01N 33/53* | (2006.01) | |
| *C12P 21/06* | (2006.01) | |

(52) U.S. Cl. ............ 435/4; 435/6.1; 435/7.21; 435/7.1
(58) Field of Classification Search ........................ None
See application file for complete search history.

(56) References Cited

U.S. PATENT DOCUMENTS

| | | | |
|---|---|---|---|
| 7,220,539 B1 * | 5/2007 | Du et al. ............................ 435/4 |
| 2005/0171027 A1 | 8/2005 | Sinclair et al. | |
| 2005/0171338 A1 * | 8/2005 | Dower et al. ................. 530/351 |
| 2006/0111556 A1 | 5/2006 | Matsui et al. | |
| 2006/0115813 A1 | 6/2006 | Yang et al. | |
| 2006/0182825 A1 * | 8/2006 | Prasad et al. .................. 424/760 |
| 2006/0223104 A1 * | 10/2006 | Kahn et al. ........................ 435/6 |

FOREIGN PATENT DOCUMENTS

| | | | |
|---|---|---|---|
| WO | WO 02/051355 A2 | 7/2002 | |
| WO | WO02053743 | * | 7/2002 |
| WO | WO/02/053743 | * | 11/2002 |

OTHER PUBLICATIONS

West & Marnett in "Alterations in Gene Expression Induced by the Lipid Peroxidation Product, 4-Hydroxy-2-nonenal" (Chem. Res. Toxicol. 2005: vol. 18, pp. 1642-1653).*
Babendure et al., "TRB3 Overexpression Inhibits GLUT4 Translocation and Glucose Uptake in 3T3-L1 Adipocytes," *Diabetes 54*:A54, 2005 (Abstract).
Du et al., "TRB3: A *tribbles* Homolog That Inhibits Akt/PKB Activation by Insulin in Liver," *Science 300*:1574-1577, 2003.
Hegedus et al., "Tribbles: Novel Regulators of Cell Function; Evolutionary Aspects," *Cell. Mol. Life Sci. 63*:1632-1641, 2006.
Klingenspor et al., "Altered Gene Expression Pattern in the Fatty Liver Dystrophy Mouse Reveals Impaired Insulin-Mediated Cytoskeleton Dynamics," *J. Biol. Chem. 274*:23078-23084, 1999.
Örd and Örd, "Characterization of Human *NIPK* (*TRB3*, *SKIP3*) Gene Activation in Stressful Conditions," *Biochem. Biophys. Res. Comm. 330*:210-218, 2005.
Schwarzer et al., "TRB3 is a PI 3-Kinase Dependent Indicator for Nutrient Starvation," *Cellular Signaling 18*:899-909, 2006.
Gloffke, "Detecting Protein Phosphorylation," *The Scientist 16*:52, 2002.
Kiss-Toth et al., "Human Tribbies, a Protein Family Controlling Mitogen-Activated Protein Kinase Cascades," *J. Biol. Chem. 279*:42703-42708, 2004.
Oh et al., "Glucose and Fat Metabolism in Adipose Tissue of Acetyl-CoA Carboxylase 2 Knockout Mice," *Proc. Natl. Acad. Sci. USA 102*:1384-1389, 2005.
Orci et al., "Rapid Transformation of White Adipocytes into Fat-Oxidizing Machines", *Proc, Natl Acad Sci. USA 101*:2058-2063, 2004.
Qi et al., "TRB3 Links the E3 Ubiquitin Ligase COP1 to Lipid Metabolism," *Science 312*:1763-1766, 2006.
Wu et al., "SINK is a p65-Interacting Negative Regulator of NF-κB-Dependent Transcription," *J Biol. Chem. 278*:27072-27079, 2003.

* cited by examiner

*Primary Examiner* — Nancy T Vogel
*Assistant Examiner* — Catherine Hibbert
(74) *Attorney, Agent, or Firm* — Klarquist Sparkman, LLP

(57) ABSTRACT

Disclosed herein are methods for identifying agents capable of affecting the expression, posttranslational modification, and/or an activity of TRB3, for example, in adipose tissue and/or adipocytes. Such agents are useful, for example, to mobilize fat stores and as prospective obesity therapeutics.

17 Claims, 9 Drawing Sheets

FIG. 11

| (ACC1) AA# | Acetyl coA Carboxylase: 13.5% Coverage | Residues of SEQ ID NO: 15 |
|---|---|---|
| 152 | R.FVVMVTPEDLK.A | 151-163 |
| 198 | K.RIPVQAVWAGWGHASENPK.L | 197-217 |
| 199 | R.IPVQAVWAGWGHASENPKLPELLLK.N | 198-224 |
| 322 | R.KVNNADDFPNLFR.Q | 321-335 |
| 356 | R.HLEVQILADQYGNAISLFGR.D | 355-376 |
| 645 | R.NSVSNFLHSLER.G | 644-657 |
| 803 | K.RPGAALDPGCVLAK.M | 802-817 |
| 825 | K.VQQAELHTGSLPR.I | 824-838 |
| 920 | K.EMAQYASNITSVLCQFPSQQIANILDSHAATLNR.K | 919-954 |
| 958 | R.EVFFMNTQSIVQLVQR.Y | 957-974 |
| 1247 | R.IFDEVMGCFCDSPPQSPTFPEAGHTSLYDEDKVPR.D | 1246-1282 |
| 1339 | Q.VNYEVDRRFHREFPKFFTFRARDK.F | 1338-1363 |
| 1904 | K.SVHSSVPLLNSKDPIDR.I | 1903-1921 |
| 1985 | V.VAVETRTVELSVPADPANLDSEAKIIQHAGQVWFPDSAFKTYQAIK.D | 1984-2031 |
| 2035 | R.EGLPLMVFANWR.G | 2034-2047 |
| 2171 | R.EEFLIPIYHQVAVQFADLHDTPGR.M | 2170-2195 |

FIG. 12

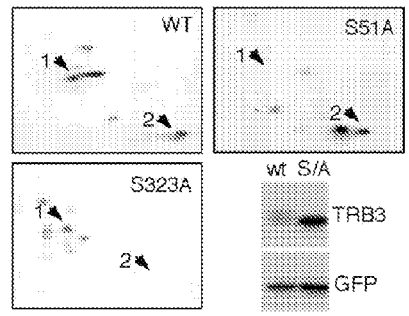

SEQUENCE LISTING

<160> NUMBER OF SEQ ID NOS: 49

<210> SEQ ID NO 1
<211> LENGTH: 1065
<212> TYPE: DNA
<213> ORGANISM: Mus musculus
<220> FEATURE:
<221> NAME/KEY: CDS
<222> LOCATION: (1)..(1065)
<220> FEATURE:
<221> NAME/KEY: misc_feature
<222> LOCATION: (824)..(824)
<223> OTHER INFORMATION: n is a, c, g, or t

<400> SEQUENCE: 1

```
atg cga gct aca cct ctg gct gct tct gct gat gtt tcc tgc agg aag      48
Met Arg Ala Thr Pro Leu Ala Ala Ser Ala Asp Val Ser Cys Arg Lys
 1               5                  10                  15 aaa ccg ttg gag ttt gat gac aat att gat gcc aag tgt cca gtc cta      96
Lys Pro Leu Glu Phe Asp Asp Asn Ile Asp Ala Lys Cys Pro Val Leu
             20                  25                  30 aaa cga gtg aga gat gag cct gag ccc gga cca ctc ccc agc ctg ctg     144
Lys Arg Val Arg Asp Glu Pro Glu Pro Gly Pro Leu Pro Ser Leu Leu
         35                  40                  45 ccc ccc agc cca cct ccc gcc tca gac ttg tca cct gct gtg gcc cct     192
Pro Pro Ser Pro Pro Ala Ser Asp Leu Ser Pro Ala Val Ala Pro
 50                  55                  60 gca act cga ctg ggg cct tat atc ctt ttg gaa cga gag caa ggc agc     240
Ala Thr Arg Leu Gly Pro Tyr Ile Leu Leu Glu Arg Glu Gln Gly Ser
 65                  70                  75                  80 tgc agc tat cga gcc ctg cac tgc ccc aca ggc aca gag tac acc tgc     288
Cys Ser Tyr Arg Ala Leu His Cys Pro Thr Gly Thr Glu Tyr Thr Cys
                 85                  90                  95 aag gtg tac cct gcc agc gag gcc cag gcg gtg ctg gca cct tat gcc     336
Lys Val Tyr Pro Ala Ser Glu Ala Gln Ala Val Leu Ala Pro Tyr Ala
            100                 105                 110 cgg ctg cct acc cac cag cat gtg gcc cgt ccc aca gag gtc ctg ctg     384
Arg Leu Pro Thr His Gln His Val Ala Arg Pro Thr Glu Val Leu Leu
        115                 120                 125 ggc tct cgg ctc ctt tac atc ttt ttc acg aag acc cat ggg gac ttg     432
Gly Ser Arg Leu Leu Tyr Ile Phe Phe Thr Lys Thr His Gly Asp Leu
130                 135                 140 cac agc ctg gtg cgc agc cgc cgc ggt atc cca gag tcc gag gct gcc     480
His Ser Leu Val Arg Ser Arg Arg Gly Ile Pro Glu Ser Glu Ala Ala
145                 150                 155                 160 ggg ctc ttc cgg cag atg gct agt gcc gtg gca cac tgc cac aag cac     528
Gly Leu Phe Arg Gln Met Ala Ser Ala Val Ala His Cys His Lys His
                165                 170                 175 ggg ctt gtc ttg cgc gac ctc aag ctg cgt cgc ttt gtc ttc agc aac     576
Gly Leu Val Leu Arg Asp Leu Lys Leu Arg Arg Phe Val Phe Ser Asn
            180                 185                 190 tgt gag agg acg aag ctg gtg ctg gag aac ctg gaa gat gcc tgc gtg     624
Cys Glu Arg Thr Lys Leu Val Leu Glu Asn Leu Glu Asp Ala Cys Val
        195                 200                 205 atg act gga tca gat gac tct ctg tgg gac acg cat gcg tgc cct gcc     672
Met Thr Gly Ser Asp Asp Ser Leu Trp Asp Thr His Ala Cys Pro Ala
    210                 215                 220 tac gtg gga cca gag ata ctc agc tcc cgg cca tcc tac tct ggc aaa     720
Tyr Val Gly Pro Glu Ile Leu Ser Ser Arg Pro Ser Tyr Ser Gly Lys
225                 230                 235                 240 gcg gct gat gtc tgg agc ctg ggt gtg gcg ctc ttc acc atg ctg gct     768
Ala Ala Asp Val Trp Ser Leu Gly Val Ala Leu Phe Thr Met Leu Ala
```

```
Ala Ala Asp Val Trp Ser Leu Gly Val Ala Leu Phe Thr Met Leu Ala
            245                 250                 255 ggc aga tac cca ttc cac gac tct gag cca gtc ctg ctc ttt ggc aag      816
Gly Arg Tyr Pro Phe His Asp Ser Glu Pro Val Leu Leu Phe Gly Lys
            260                 265                 270 atc cgt ana ggg acc ttt gcc ctg cct gag ggc cta tca gcc cca gcc      864
Ile Arg Xaa Gly Thr Phe Ala Leu Pro Glu Gly Leu Ser Ala Pro Ala
            275                 280                 285 cgc tgt ctg atc cgc tgt ctc ctc cgc aag gaa cct tca gag cga ctt      912
Arg Cys Leu Ile Arg Cys Leu Leu Arg Lys Glu Pro Ser Glu Arg Leu
            290                 295                 300 gtg gcc ctg gga atc ctc ttg cat ccc tgg ttg aga gag gat cac ggc      960
Val Ala Leu Gly Ile Leu Leu His Pro Trp Leu Arg Glu Asp His Gly
305                 310                 315                 320 cga gtc tct cct cca cag tct gac cga agg gag atg gac cag gtg gtc    1008
Arg Val Ser Pro Pro Gln Ser Asp Arg Arg Glu Met Asp Gln Val Val
                325                 330                 335 cca gat ggg cca cag ctg gag gag gct gag gaa ggg gag gtg ggg ctg    1056
Pro Asp Gly Pro Gln Leu Glu Glu Ala Glu Glu Gly Glu Val Gly Leu
            340                 345                 350 tac ggc tag                                                         1065
Tyr Gly <210> SEQ ID NO 2
<211> LENGTH: 354
<212> TYPE: PRT
<213> ORGANISM: Mus musculus
<220> FEATURE:
<221> NAME/KEY: misc_feature
<222> LOCATION: (275)..(275)
<223> OTHER INFORMATION: The 'Xaa' at location 275 stands for Lys, Arg,
      Thr, or Ile.

<400> SEQUENCE: 2

Met Arg Ala Thr Pro Leu Ala Ala Ser Ala Asp Val Ser Cys Arg Lys
1               5                   10                  15

Lys Pro Leu Glu Phe Asp Asp Asn Ile Asp Ala Lys Cys Pro Val Leu
            20                  25                  30

Lys Arg Val Arg Asp Glu Pro Glu Pro Gly Pro Leu Pro Ser Leu Leu
        35                  40                  45

Pro Pro Ser Pro Pro Ala Ser Asp Leu Ser Pro Ala Val Ala Pro
    50                  55                  60

Ala Thr Arg Leu Gly Pro Tyr Ile Leu Leu Glu Arg Glu Gln Gly Ser
65                  70                  75                  80

Cys Ser Tyr Arg Ala Leu His Cys Pro Thr Gly Thr Glu Tyr Thr Cys
                85                  90                  95

Lys Val Tyr Pro Ala Ser Glu Ala Gln Ala Val Leu Ala Pro Tyr Ala
            100                 105                 110

Arg Leu Pro Thr His Gln His Val Ala Arg Pro Thr Glu Val Leu Leu
        115                 120                 125

Gly Ser Arg Leu Leu Tyr Ile Phe Phe Thr Lys Thr His Gly Asp Leu
    130                 135                 140

His Ser Leu Val Arg Ser Arg Arg Gly Ile Pro Glu Ser Glu Ala Ala
145                 150                 155                 160

Gly Leu Phe Arg Gln Met Ala Ser Ala Val Ala His Cys His Lys His
                165                 170                 175

Gly Leu Val Leu Arg Asp Leu Lys Leu Arg Arg Phe Val Phe Ser Asn
            180                 185                 190

Cys Glu Arg Thr Lys Leu Val Leu Glu Asn Leu Glu Asp Ala Cys Val
```

```
               195                 200                 205
Met Thr Gly Ser Asp Asp Ser Leu Trp Asp Thr His Ala Cys Pro Ala
210                 215                 220

Tyr Val Gly Pro Glu Ile Leu Ser Ser Arg Pro Ser Tyr Ser Gly Lys
225                 230                 235                 240

Ala Ala Asp Val Trp Ser Leu Gly Val Ala Leu Phe Thr Met Leu Ala
            245                 250                 255

Gly Arg Tyr Pro Phe His Asp Ser Glu Pro Val Leu Leu Phe Gly Lys
                260                 265                 270

Ile Arg Xaa Gly Thr Phe Ala Leu Pro Glu Gly Leu Ser Ala Pro Ala
            275                 280                 285

Arg Cys Leu Ile Arg Cys Leu Leu Arg Lys Glu Pro Ser Glu Arg Leu
        290                 295                 300

Val Ala Leu Gly Ile Leu Leu His Pro Trp Leu Arg Glu Asp His Gly
305                 310                 315                 320

Arg Val Ser Pro Pro Gln Ser Asp Arg Arg Glu Met Asp Gln Val Val
                325                 330                 335

Pro Asp Gly Pro Gln Leu Glu Glu Ala Glu Glu Gly Glu Val Gly Leu
            340                 345                 350

Tyr Gly

<210> SEQ ID NO 3
<211> LENGTH: 2469
<212> TYPE: DNA
<213> ORGANISM: Homo sapiens
<220> FEATURE:
<221> NAME/KEY: CDS
<222> LOCATION: (507)..(1583)

<400> SEQUENCE: 3
gacagagcaa gactctgtct caaaaaaaaa aaaaaaaga gcaaatttttt tttccaaggt      60 gatagggaga gtccgtggct gatgtctgca ctgaccagac gccccctaggg ggccagcgag     120 ggcgggtccc aggtgcagcg gatgcagagg agagaggccc gggcgcggcg cgggggatgg     180
tgcgatcccg ggcccagggg catcagacgc gggctgatta gctccggttt gcatcacccg     240
gaccggggga ttagctccgg tttgcatcac ccggaccggg ggattagctc cggtttgcat     300
cacccggacc gggggccggg cgcgcacgag actcgcagcg gaagtggagg cggctccgcg     360
cgcgtccgct gctaggaccc gggcagggct ggagctgggc tgggatcccg agctcggcag     420
cagcgcagcg ggccggccca cctgctggtg ccctggaggc tctgagcccc ggcggcgccc     480
gggcccacgc ggaacgacgg ggcgag atg cga gcc acc cct ctg gct gct cct       533
                              Met Arg Ala Thr Pro Leu Ala Ala Pro
                                1               5 gcg ggt tcc ctg tcc agg aag aag cgg ttg gag ttg gat gac aac tta        581
Ala Gly Ser Leu Ser Arg Lys Lys Arg Leu Glu Leu Asp Asp Asn Leu
 10                  15                  20                  25 gat acc gag cgt ccc gtc cag aaa cga gct cga agt ggg ccc cag ccc        629
Asp Thr Glu Arg Pro Val Gln Lys Arg Ala Arg Ser Gly Pro Gln Pro
                 30                  35                  40 aga ctg ccc ccc tgc ctg ttg ccc ctg agc cca cct act gct cca gat        677
Arg Leu Pro Pro Cys Leu Leu Pro Leu Ser Pro Pro Thr Ala Pro Asp
             45                  50                  55 cgt gca act gct gtg gcc act gcc tcc cgt ctt ggg ccc tat gtc ctc        725
Arg Ala Thr Ala Val Ala Thr Ala Ser Arg Leu Gly Pro Tyr Val Leu
         60                  65                  70 ctg gag ccc gag gag ggc ggg cgg gcc tac cag gcc ctg cac tgc cct        773
Leu Glu Pro Glu Glu Gly Gly Arg Ala Tyr Gln Ala Leu His Cys Pro
```

-continued

```
            75                  80                  85
aca ggc act gag tat acc tgc aag gtg tac ccc gtc cag gaa gcc ctg         821
Thr Gly Thr Glu Tyr Thr Cys Lys Val Tyr Pro Val Gln Glu Ala Leu
 90                  95                 100                 105 gcc gtg ctg gag ccc tat gcg cgg ctg ccc ccg cac aag cat gtg gct         869
Ala Val Leu Glu Pro Tyr Ala Arg Leu Pro Pro His Lys His Val Ala
                 110                 115                 120 cgg ccc act gag gtc ctg gct ggt acc cag ctc ctc tac gcc ttt ttc         917
Arg Pro Thr Glu Val Leu Ala Gly Thr Gln Leu Leu Tyr Ala Phe Phe
             125                 130                 135 act cgg acc cat ggg gac atg cac agc ctg gtg cga agc cgc cac cgt         965
Thr Arg Thr His Gly Asp Met His Ser Leu Val Arg Ser Arg His Arg
         140                 145                 150 atc cct gag cct gag gct gcc gtg ctc ttc cgc cag atg gcc acc gcc        1013
Ile Pro Glu Pro Glu Ala Ala Val Leu Phe Arg Gln Met Ala Thr Ala
     155                 160                 165 ctg gcg cac tgt cac cag cac ggt ctg gtc ctg cgt gat ctc aag ctg        1061
Leu Ala His Cys His Gln His Gly Leu Val Leu Arg Asp Leu Lys Leu
170                 175                 180                 185 tgt cgc ttt gtc ttc gct gac cgt gag agg aag aag ctg gtg ctg gag        1109
Cys Arg Phe Val Phe Ala Asp Arg Glu Arg Lys Lys Leu Val Leu Glu
                 190                 195                 200 aac ctg gag gac tcc tgc gtg ctg act ggg cca gat gat tcc ctg tgg        1157
Asn Leu Glu Asp Ser Cys Val Leu Thr Gly Pro Asp Asp Ser Leu Trp
             205                 210                 215 gac aag cac gcg tgc cca gcc tac gtg gga cct gag ata ctc agc tca        1205
Asp Lys His Ala Cys Pro Ala Tyr Val Gly Pro Glu Ile Leu Ser Ser
         220                 225                 230 cgg gcc tca tac tcg ggc aag gca gcc gat gtc tgg agc ctg ggc gtg        1253
Arg Ala Ser Tyr Ser Gly Lys Ala Ala Asp Val Trp Ser Leu Gly Val
     235                 240                 245 gcg ctc ttc acc atg ctg gcc ggc cac tac ccc ttc cag gac tcg gag        1301
Ala Leu Phe Thr Met Leu Ala Gly His Tyr Pro Phe Gln Asp Ser Glu
250                 255                 260                 265 cct gtc ctg ctc ttc ggc aag atc cgc cgc ggg gcc tac gcc ttg cct        1349
Pro Val Leu Leu Phe Gly Lys Ile Arg Arg Gly Ala Tyr Ala Leu Pro
                 270                 275                 280 gca ggc ctc tcg gcc cct gcc cgc tgt ctg gtt cgc tgc ctc ctt cgt        1397
Ala Gly Leu Ser Ala Pro Ala Arg Cys Leu Val Arg Cys Leu Leu Arg
             285                 290                 295 cgg gag cca gct gaa cgg ctc aca gcc aca ggc atc ctc ctg cac ccc        1445
Arg Glu Pro Ala Glu Arg Leu Thr Ala Thr Gly Ile Leu Leu His Pro
         300                 305                 310 tgg ctg cga cag gac ccg atg ccc tta gcc cca acc cga tcc cat ctc        1493
Trp Leu Arg Gln Asp Pro Met Pro Leu Ala Pro Thr Arg Ser His Leu
     315                 320                 325 tgg gag gct gcc cag gtg gtc cct gat gga ctg ggg ctg gac gaa gcc        1541
Trp Glu Ala Ala Gln Val Val Pro Asp Gly Leu Gly Leu Asp Glu Ala
330                 335                 340                 345 agg gaa gag gag gga gac aga gaa gtg gtt ctg tat ggc tag             1583
Arg Glu Glu Glu Gly Asp Arg Glu Val Val Leu Tyr Gly
                 350                 355 gaccacccta ctacacgctc agctgccaac agtggattga gtttgggggt agctccaagc    1643
cttctcctgc ctctgaactg agccaaacct tcagtgcctt ccagaaggga gaaaggcaga    1703
agcctgtgtg gagtgtgctg tgtacacatc tgctttgttc cacacacatg cagttcctgc    1763
ttgggtgctt atcaggtgcc aagccctgtt ctcggtgctg ggagtacagc agtgagcaaa    1823
ggagacaata ttccctgctc acagagatga caaactggca tccttgagct gacaacactt    1883
```

-continued

```
ttccatgacc ataggtcact gtctacactg ggtacacttt gtaccagtgt cggcctccac    1943
tgatgctggt gctcaggcac ctctgtccaa ggacaatccc tttcacaaac aaaccagctg    2003
cctttgtatc ttgtaccttt tcagagaaag ggaggtatcc ctgtgccaaa ggctccaggc    2063
ctctcccctg caactcagga cccaagccca gctcactctg gaactgtgt tcccagcatc    2123 tctgtcctct tgattaagag attctccttc caggcctaag cctgggattt gggccagaga    2183
taagaatcca aactatgagg ctagttcttg tctaactcaa gactgttctg gaatgagggt    2243
ccaggcctgt caaccatggg gcttctgacc tgagcaccaa ggttgaggga caggattagg    2303
cagggtctgt cctgtggcca cctggaaagt cccaggtggg actcttctgg ggacacttgg    2363
ggtccacaat cccaggtcca tactctaggt tttggatacc atgagtatgt atgtttacct    2423
gtgcctaata aaggagaatt atgaaataaa aaaaaaaaa aaaaaa                   2469

<210> SEQ ID NO 4
<211> LENGTH: 358
<212> TYPE: PRT
<213> ORGANISM: Homo sapiens

<400> SEQUENCE: 4

Met Arg Ala Thr Pro Leu Ala Ala Pro Ala Gly Ser Leu Ser Arg Lys
1               5                   10                  15

Lys Arg Leu Glu Leu Asp Asp Asn Leu Asp Thr Glu Arg Pro Val Gln
            20                  25                  30

Lys Arg Ala Arg Ser Gly Pro Gln Pro Arg Leu Pro Pro Cys Leu Leu
        35                  40                  45

Pro Leu Ser Pro Pro Thr Ala Pro Asp Arg Ala Thr Ala Val Ala Thr
    50                  55                  60

Ala Ser Arg Leu Gly Pro Tyr Val Leu Leu Glu Pro Glu Glu Gly Gly
65                  70                  75                  80

Arg Ala Tyr Gln Ala Leu His Cys Pro Thr Gly Thr Glu Tyr Thr Cys
                85                  90                  95

Lys Val Tyr Pro Val Gln Glu Ala Leu Ala Val Leu Glu Pro Tyr Ala
            100                 105                 110

Arg Leu Pro Pro His Lys His Val Ala Arg Pro Thr Glu Val Leu Ala
        115                 120                 125

Gly Thr Gln Leu Leu Tyr Ala Phe Phe Thr Arg Thr His Gly Asp Met
    130                 135                 140

His Ser Leu Val Arg Ser Arg His Arg Ile Pro Glu Pro Glu Ala Ala
145                 150                 155                 160

Val Leu Phe Arg Gln Met Ala Thr Ala Leu Ala His Cys His Gln His
                165                 170                 175

Gly Leu Val Leu Arg Asp Leu Lys Leu Cys Arg Phe Val Phe Ala Asp
            180                 185                 190

Arg Glu Arg Lys Lys Leu Val Leu Glu Asn Leu Glu Asp Ser Cys Val
        195                 200                 205

Leu Thr Gly Pro Asp Asp Ser Leu Trp Asp Lys His Ala Cys Pro Ala
    210                 215                 220

Tyr Val Gly Pro Glu Ile Leu Ser Ser Arg Ala Ser Tyr Ser Gly Lys
225                 230                 235                 240

Ala Ala Asp Val Trp Ser Leu Gly Val Ala Leu Phe Thr Met Leu Ala
                245                 250                 255

Gly His Tyr Pro Phe Gln Asp Ser Glu Pro Val Leu Leu Phe Gly Lys
            260                 265                 270

Ile Arg Arg Gly Ala Tyr Ala Leu Pro Ala Gly Leu Ser Ala Pro Ala
```

```
                  275                 280                 285
Arg Cys Leu Val Arg Cys Leu Leu Arg Arg Glu Pro Ala Glu Arg Leu
            290                 295                 300
Thr Ala Thr Gly Ile Leu Leu His Pro Trp Leu Arg Gln Asp Pro Met
305                 310                 315                 320
Pro Leu Ala Pro Thr Arg Ser His Leu Trp Glu Ala Ala Gln Val Val
                325                 330                 335
Pro Asp Gly Leu Gly Leu Asp Glu Ala Arg Glu Glu Gly Asp Arg
            340                 345                 350
Glu Val Val Leu Tyr Gly
        355

<210> SEQ ID NO 5
<211> LENGTH: 1119
<212> TYPE: DNA
<213> ORGANISM: Canis familiaris
<220> FEATURE:
<221> NAME/KEY: CDS
<222> LOCATION: (1)..(1119)

<400> SEQUENCE: 5 atg cgg gtc ggt ccc gtg cgc tcg gcc atg agc ggc gcc tcg cag ccc     48
Met Arg Val Gly Pro Val Arg Ser Ala Met Ser Gly Ala Ser Gln Pro
1               5                   10                  15 cgc ggc ccg gcc ctg ctc ctc ccg gcc gcc cgg ggc gcc ccg gcc aaa     96
Arg Gly Pro Ala Leu Leu Leu Pro Ala Ala Arg Gly Ala Pro Ala Lys
                20                  25                  30 cgc ctg ctg gac gcg gac gac gcg gcg gcc gtg gcg gcc aag tgc ccg    144
Arg Leu Leu Asp Ala Asp Asp Ala Ala Ala Val Ala Ala Lys Cys Pro
            35                  40                  45 cgc ctc tcc gag tgc tcg agc ccc ccg gac tac ctc agc ccc ccc ggc    192
Arg Leu Ser Glu Cys Ser Ser Pro Pro Asp Tyr Leu Ser Pro Pro Gly
        50                  55                  60 tcg ccc tgc agc ccg cag ccg ccg ccc gcc gtt ccg gga gcc ggc ggc    240
Ser Pro Cys Ser Pro Gln Pro Pro Pro Ala Val Pro Gly Ala Gly Gly
65                  70                  75                  80 ggc tgc ggg agc gcg ccg ggg ccc agc cgc atc gcc gac tac ctg ctg    288
Gly Cys Gly Ser Ala Pro Gly Pro Ser Arg Ile Ala Asp Tyr Leu Leu
                85                  90                  95 ctg ccg ctg gcg gag cgc gag cat gtg tcc cgg gcg ctg tgc atc cac    336
Leu Pro Leu Ala Glu Arg Glu His Val Ser Arg Ala Leu Cys Ile His
                100                 105                 110 acc ggc cgc gag ctg cgc tgc aag gtg ttt cct att aaa cac tac cag    384
Thr Gly Arg Glu Leu Arg Cys Lys Val Phe Pro Ile Lys His Tyr Gln
            115                 120                 125 gac aaa atc agg cct tac atc cag ctg ccg tca cac agg aac atc act    432
Asp Lys Ile Arg Pro Tyr Ile Gln Leu Pro Ser His Arg Asn Ile Thr
        130                 135                 140 ggc att gtg gaa gtg atc ctt ggg gaa acc aag gcc tat gtc ttc ttt    480
Gly Ile Val Glu Val Ile Leu Gly Glu Thr Lys Ala Tyr Val Phe Phe
145                 150                 155                 160 gag aag gac ttt ggg gac atg cac tcc tat gtg cga agc cgg aag agg    528
Glu Lys Asp Phe Gly Asp Met His Ser Tyr Val Arg Ser Arg Lys Arg
                165                 170                 175 ctg cgg gaa gag gag gct gcc cgg ctc ttc aag cag att gtt tcc gcc    576
Leu Arg Glu Glu Glu Ala Ala Arg Leu Phe Lys Gln Ile Val Ser Ala
                180                 185                 190 gtt gcc cac tgc cat cag tcg gcc atc gtg ctc ggg gac ctg aaa ctt    624
Val Ala His Cys His Gln Ser Ala Ile Val Leu Gly Asp Leu Lys Leu
            195                 200                 205
```

```
agg aaa ttc gtc ttc tcc acg gag gag aga agc cag ctc aga ctg gaa    672
Arg Lys Phe Val Phe Ser Thr Glu Glu Arg Ser Gln Leu Arg Leu Glu
    210                 215                 220 agt cta gaa gac aca cac ata atc aag ggg gaa gac gat gct ctg tca    720
Ser Leu Glu Asp Thr His Ile Ile Lys Gly Glu Asp Asp Ala Leu Ser
225                 230                 235                 240 gac aag cac ggc tgc ccg gcc tac gtg agc cct gag att ctg aac acc    768
Asp Lys His Gly Cys Pro Ala Tyr Val Ser Pro Glu Ile Leu Asn Thr
                245                 250                 255 acg ggg acc tac tcc gga aag gcg gca gac gtt tgg agc cta ggg gtg    816
Thr Gly Thr Tyr Ser Gly Lys Ala Ala Asp Val Trp Ser Leu Gly Val
        260                 265                 270 atg ctc tac acc ctt ttg gtg gga cga tac ccc ttc cat gac tca gat    864
Met Leu Tyr Thr Leu Leu Val Gly Arg Tyr Pro Phe His Asp Ser Asp
    275                 280                 285 ccc agt gcc ctc ttc tcc aaa atc cga cgt gga cag ttc tgc att cct    912
Pro Ser Ala Leu Phe Ser Lys Ile Arg Arg Gly Gln Phe Cys Ile Pro
290                 295                 300 gac cac att tcc ccc aaa gcc agg tgc ctc att cgc agc ctc ctg aga    960
Asp His Ile Ser Pro Lys Ala Arg Cys Leu Ile Arg Ser Leu Leu Arg
305                 310                 315                 320 cgg gag ccc tcc gag aga ctc act gcc ccg gag atc tta ctc cat ccc   1008
Arg Glu Pro Ser Glu Arg Leu Thr Ala Pro Glu Ile Leu Leu His Pro
                325                 330                 335 tgg ttt gag tct gtc ttg gaa cct gga tac gtt gac tca gaa atg gga   1056
Trp Phe Glu Ser Val Leu Glu Pro Gly Tyr Val Asp Ser Glu Met Gly
        340                 345                 350 act tca gac cag att gtt cca gac tac caa gag gac agt gac att agt   1104
Thr Ser Asp Gln Ile Val Pro Asp Tyr Gln Glu Asp Ser Asp Ile Ser
    355                 360                 365 tcc ttc ttc tgc taa                                                1119
Ser Phe Phe Cys
    370

<210> SEQ ID NO 6
<211> LENGTH: 372
<212> TYPE: PRT
<213> ORGANISM: Canis familiaris

<400> SEQUENCE: 6

Met Arg Val Gly Pro Val Arg Ser Ala Met Ser Gly Ala Ser Gln Pro
1               5                   10                  15

Arg Gly Pro Ala Leu Leu Pro Ala Ala Arg Gly Ala Pro Ala Lys
            20                  25                  30

Arg Leu Leu Asp Ala Asp Ala Ala Val Ala Ala Lys Cys Pro
            35                  40                  45

Arg Leu Ser Glu Cys Ser Pro Pro Asp Tyr Leu Ser Pro Gly
    50                  55                  60

Ser Pro Cys Ser Pro Gln Pro Pro Ala Val Pro Gly Ala Gly
65                  70                  75                  80

Gly Cys Gly Ser Ala Pro Gly Pro Ser Arg Ile Ala Asp Tyr Leu Leu
                85                  90                  95

Leu Pro Leu Ala Glu Arg Glu His Val Ser Arg Ala Leu Cys Ile His
            100                 105                 110

Thr Gly Arg Glu Leu Arg Cys Lys Val Phe Pro Ile Lys His Tyr Gln
        115                 120                 125

Asp Lys Ile Arg Pro Tyr Ile Gln Leu Pro Ser His Arg Asn Ile Thr
    130                 135                 140

Gly Ile Val Glu Val Ile Leu Gly Glu Thr Lys Ala Tyr Val Phe Phe
```

```
                145                 150                 155                 160
Glu Lys Asp Phe Gly Asp Met His Ser Tyr Val Arg Ser Arg Lys Arg
                165                 170                 175

Leu Arg Glu Glu Glu Ala Ala Arg Leu Phe Lys Gln Ile Val Ser Ala
            180                 185                 190

Val Ala His Cys His Gln Ser Ala Ile Val Leu Gly Asp Leu Lys Leu
        195                 200                 205

Arg Lys Phe Val Phe Ser Thr Glu Glu Arg Ser Gln Leu Arg Leu Glu
    210                 215                 220

Ser Leu Glu Asp Thr His Ile Ile Lys Gly Glu Asp Ala Leu Ser
225                 230                 235                 240

Asp Lys His Gly Cys Pro Ala Tyr Val Ser Pro Glu Ile Leu Asn Thr
                245                 250                 255

Thr Gly Thr Tyr Ser Gly Lys Ala Ala Asp Val Trp Ser Leu Gly Val
            260                 265                 270

Met Leu Tyr Thr Leu Leu Val Gly Arg Tyr Pro Phe His Asp Ser Asp
        275                 280                 285

Pro Ser Ala Leu Phe Ser Lys Ile Arg Arg Gly Gln Phe Cys Ile Pro
    290                 295                 300

Asp His Ile Ser Pro Lys Ala Arg Cys Leu Ile Arg Ser Leu Leu Arg
305                 310                 315                 320

Arg Glu Pro Ser Glu Arg Leu Thr Ala Pro Glu Ile Leu Leu His Pro
                325                 330                 335

Trp Phe Glu Ser Val Leu Glu Pro Gly Tyr Val Asp Ser Glu Met Gly
            340                 345                 350

Thr Ser Asp Gln Ile Val Pro Asp Tyr Gln Glu Asp Ser Asp Ile Ser
        355                 360                 365

Ser Phe Phe Cys
    370

<210> SEQ ID NO 7
<211> LENGTH: 1119
<212> TYPE: DNA
<213> ORGANISM: Bos taurus
<220> FEATURE:
<221> NAME/KEY: CDS
<222> LOCATION: (1)..(1119)

<400> SEQUENCE: 7 atg cgg gtc ggt ccc gtg cgc tct gcc atg aac ggc gtc tcg cag ccc     48
Met Arg Val Gly Pro Val Arg Ser Ala Met Asn Gly Val Ser Gln Pro
1               5                   10                  15 cgc act ccg gcc ttg ttg ctc gcc gcc ggc cgg ggc acc ccg gcc aaa     96
Arg Thr Pro Ala Leu Leu Leu Ala Ala Gly Arg Gly Thr Pro Ala Lys
            20                  25                  30 cgc ctg ctg gac gcg gac gac gca gcg gcc gtg gcg gcc aag tgc cca    144
Arg Leu Leu Asp Ala Asp Asp Ala Ala Ala Val Ala Ala Lys Cys Pro
        35                  40                  45 cgt ctc tcc gag tgt tcg agc ccc ccg gac tac ctc agc ccc cct ggc    192
Arg Leu Ser Glu Cys Ser Ser Pro Pro Asp Tyr Leu Ser Pro Pro Gly
    50                  55                  60 tct ccc tgc agc ccg cag cct ccg ccc gcc gct cca ggg gcc ggc ggc    240
Ser Pro Cys Ser Pro Gln Pro Pro Pro Ala Ala Pro Gly Ala Gly Gly
65                  70                  75                  80 ggc tcc ggg agc gct ccg ggg ccc agc cgc atc gcc gac tac ctg ctg    288
Gly Ser Gly Ser Ala Pro Gly Pro Ser Arg Ile Ala Asp Tyr Leu Leu
                85                  90                  95 ctg ccc ctg gct gag cgc gag cat gtg tcc cgg gcg ctg tgc atc cac    336
```

| | | | | | | | | | | | | |
|---|---|---|---|---|---|---|---|---|---|---|---|---|
| Leu | Pro | Leu | Ala | Glu | Arg | Glu | His | Val | Ser | Arg | Ala | Leu | Cys | Ile | His |
| | | | 100 | | | | | 105 | | | | | 110 | | |

```
acc ggc cgc gag ctg cgc tgc aag gtg ttt ccc att aaa cac tac cag      384
Thr Gly Arg Glu Leu Arg Cys Lys Val Phe Pro Ile Lys His Tyr Gln
        115                 120                 125 gac aaa atc cgg cct tac atc cag ctg cca tca cat agg aac atc acg      432
Asp Lys Ile Arg Pro Tyr Ile Gln Leu Pro Ser His Arg Asn Ile Thr
    130                 135                 140 ggc atc gtg gag gtg atc ctt ggg gaa aca aag gcc tac gtc ttc ttt      480
Gly Ile Val Glu Val Ile Leu Gly Glu Thr Lys Ala Tyr Val Phe Phe
145                 150                 155                 160 gag agg gac ttt ggg gac atg cac tcc tac gtg cgc agc cgg aag agg      528
Glu Arg Asp Phe Gly Asp Met His Ser Tyr Val Arg Ser Arg Lys Arg
                165                 170                 175 ttg cgg gaa gag gag gcc gcc cgg ctc ttc aag cag att gtc tct gcc      576
Leu Arg Glu Glu Glu Ala Ala Arg Leu Phe Lys Gln Ile Val Ser Ala
            180                 185                 190 gtc gcc cac tgc cac cag tca gcc att gtg ctg ggg gac ctg aag ctt      624
Val Ala His Cys His Gln Ser Ala Ile Val Leu Gly Asp Leu Lys Leu
        195                 200                 205 agg aag ttt gtc ttc tcc acc gaa gag aga acc cag ctc aga ctg gaa      672
Arg Lys Phe Val Phe Ser Thr Glu Glu Arg Thr Gln Leu Arg Leu Glu
    210                 215                 220 agt ctt gaa gat aca cac ata atc aag gga gaa gat gat gct ttg tca      720
Ser Leu Glu Asp Thr His Ile Ile Lys Gly Glu Asp Asp Ala Leu Ser
225                 230                 235                 240 gac aaa cac ggc tgc cca gcc tat gtg agc cct gag att ctg aac acc      768
Asp Lys His Gly Cys Pro Ala Tyr Val Ser Pro Glu Ile Leu Asn Thr
                245                 250                 255 acg ggg acc tac tcc gga aag gca gcg gac gtt tgg agc ctt ggg gtg      816
Thr Gly Thr Tyr Ser Gly Lys Ala Ala Asp Val Trp Ser Leu Gly Val
            260                 265                 270 atg ctc tac acc ctt ttg gtg ggg cgc tac ccc ttc cat gac tca gac      864
Met Leu Tyr Thr Leu Leu Val Gly Arg Tyr Pro Phe His Asp Ser Asp
        275                 280                 285 ccc agt gcc ctt ttc tcc aaa atc cga cgt gga cag ttc tgc att cct      912
Pro Ser Ala Leu Phe Ser Lys Ile Arg Arg Gly Gln Phe Cys Ile Pro
    290                 295                 300 gac cac att tct ccc aaa gcc agg tgc ctc att cgc agc ctc ctg aga      960
Asp His Ile Ser Pro Lys Ala Arg Cys Leu Ile Arg Ser Leu Leu Arg
305                 310                 315                 320 cgg gag ccg tca gag aga ctc act gcc cca gag atc tta ctc cat ccc     1008
Arg Glu Pro Ser Glu Arg Leu Thr Ala Pro Glu Ile Leu Leu His Pro
                325                 330                 335 tgg ttt gag tct gtc ttg gaa cct ggg tac atc gac tca gaa gta gga     1056
Trp Phe Glu Ser Val Leu Glu Pro Gly Tyr Ile Asp Ser Glu Val Gly
            340                 345                 350 act tcc gac cag att gtt cca gag tac cag gag gac agt gac atc agt     1104
Thr Ser Asp Gln Ile Val Pro Glu Tyr Gln Glu Asp Ser Asp Ile Ser
        355                 360                 365 tcc ttc ttc tgc taa                                                 1119
Ser Phe Phe Cys
    370
```

<210> SEQ ID NO 8
<211> LENGTH: 372
<212> TYPE: PRT
<213> ORGANISM: Bos taurus

<400> SEQUENCE: 8

Met Arg Val Gly Pro Val Arg Ser Ala Met Asn Gly Val Ser Gln Pro

```
                1               5                  10                 15
        Arg Thr Pro Ala Leu Leu Ala Ala Gly Arg Gly Thr Pro Ala Lys
                        20                  25                  30

Arg Leu Leu Asp Ala Asp Ala Ala Val Ala Ala Lys Cys Pro
                        35                  40                  45

Arg Leu Ser Glu Cys Ser Ser Pro Asp Tyr Leu Ser Pro Gly
                50                  55                  60

Ser Pro Cys Ser Pro Gln Pro Pro Ala Ala Pro Gly Ala Gly Gly
        65                  70                  75                  80

Gly Ser Gly Ser Ala Pro Gly Pro Ser Arg Ile Ala Asp Tyr Leu Leu
                        85                  90                  95

Leu Pro Leu Ala Glu Arg Glu His Val Ser Arg Ala Leu Cys Ile His
                        100                 105                 110

Thr Gly Arg Glu Leu Arg Cys Lys Val Phe Pro Ile Lys His Tyr Gln
                        115                 120                 125

Asp Lys Ile Arg Pro Tyr Ile Gln Leu Pro Ser His Arg Asn Ile Thr
                        130                 135                 140

Gly Ile Val Glu Val Ile Leu Gly Glu Thr Lys Ala Tyr Val Phe Phe
        145                 150                 155                 160

Glu Arg Asp Phe Gly Asp Met His Ser Tyr Val Arg Ser Arg Lys Arg
                        165                 170                 175

Leu Arg Glu Glu Ala Ala Arg Leu Phe Lys Gln Ile Val Ser Ala
                        180                 185                 190

Val Ala His Cys His Gln Ser Ala Ile Val Leu Gly Asp Leu Lys Leu
                        195                 200                 205

Arg Lys Phe Val Phe Ser Thr Glu Glu Arg Thr Gln Leu Arg Leu Glu
                        210                 215                 220

Ser Leu Glu Asp Thr His Ile Ile Lys Gly Glu Asp Asp Ala Leu Ser
        225                 230                 235                 240

Asp Lys His Gly Cys Pro Ala Tyr Val Ser Pro Glu Ile Leu Asn Thr
                        245                 250                 255

Thr Gly Thr Tyr Ser Gly Lys Ala Ala Asp Val Trp Ser Leu Gly Val
                        260                 265                 270

Met Leu Tyr Thr Leu Leu Val Gly Arg Tyr Pro Phe His Asp Ser Asp
                        275                 280                 285

Pro Ser Ala Leu Phe Ser Lys Ile Arg Arg Gly Gln Phe Cys Ile Pro
                        290                 295                 300

Asp His Ile Ser Pro Lys Ala Arg Cys Leu Ile Arg Ser Leu Leu Arg
        305                 310                 315                 320

Arg Glu Pro Ser Glu Arg Leu Thr Ala Pro Glu Ile Leu Leu His Pro
                        325                 330                 335

Trp Phe Glu Ser Val Leu Glu Pro Gly Tyr Ile Asp Ser Glu Val Gly
                        340                 345                 350

Thr Ser Asp Gln Ile Val Pro Glu Tyr Gln Glu Asp Ser Asp Ile Ser
                        355                 360                 365

Ser Phe Phe Cys
              370

<210> SEQ ID NO 9
<211> LENGTH: 1401
<212> TYPE: DNA
<213> ORGANISM: Gallus gallus
<220> FEATURE:
<221> NAME/KEY: CDS
<222> LOCATION: (1)..(1401)
```

<400> SEQUENCE: 9

```
atg gat ccg agg tgc agc gtg gcc cat cgg cct ggc acc aat gac agt      48
Met Asp Pro Arg Cys Ser Val Ala His Arg Pro Gly Thr Asn Asp Ser
1               5                   10                  15 gct ctg tta cat agt aaa gat gca cct ggg aaa cat gtt tcc tgg aat      96
Ala Leu Leu His Ser Lys Asp Ala Pro Gly Lys His Val Ser Trp Asn
            20                  25                  30 gga aaa ttc ctc ctt tct ctt gct gca gcc aaa gca ttg aac caa ggg     144
Gly Lys Phe Leu Leu Ser Leu Ala Ala Ala Lys Ala Leu Asn Gln Gly
        35                  40                  45 cac ctc atc aca act aca gca aaa ctg tcg gtc atc cag gag ctt ttt     192
His Leu Ile Thr Thr Thr Ala Lys Leu Ser Val Ile Gln Glu Leu Phe
    50                  55                  60 aac aca gaa agt tct gac tcg agc agc cag ttt att tat aac tgg ccc     240
Asn Thr Glu Ser Ser Asp Ser Ser Ser Gln Phe Ile Tyr Asn Trp Pro
65                  70                  75                  80 aat cca aca gag tca ctc tgc gta tcc cac gag aca cac tgt cag agt     288
Asn Pro Thr Glu Ser Leu Cys Val Ser His Glu Thr His Cys Gln Ser
                85                  90                  95 aac cag acc tgt ccc aag cac cgg gga agt ggg gag atg gtt aca caa     336
Asn Gln Thr Cys Pro Lys His Arg Gly Ser Gly Glu Met Val Thr Gln
            100                 105                 110 ttc cca ttg ccg ctg gct gct cca gtt aca gag ata aag ggt cag aga     384
Phe Pro Leu Pro Leu Ala Ala Pro Val Thr Glu Ile Lys Gly Gln Arg
        115                 120                 125 agt gga gca gtg gag aca gat aac tct gtg agc atc atg ggg cga gca     432
Ser Gly Ala Val Glu Thr Asp Asn Ser Val Ser Ile Met Gly Arg Ala
    130                 135                 140 gcc gag ctc gca gtg ctg gac ttt cgc tcc ccg tcg tcc gtg cgg agc     480
Ala Glu Leu Ala Val Leu Asp Phe Arg Ser Pro Ser Ser Val Arg Ser
145                 150                 155                 160 gag cgg cgg agc cgc ggg gga ggg tct cgg tcc cgc tcc gag cgg agc     528
Glu Arg Arg Ser Arg Gly Gly Gly Ser Arg Ser Arg Ser Glu Arg Ser
                165                 170                 175 acg gag ccc cgg cgc tcc tcc atc ccc ggc gtt gtt tgg aaa gag tct     576
Thr Glu Pro Arg Arg Ser Ser Ile Pro Gly Val Val Trp Lys Glu Ser
            180                 185                 190 ctg gac gcg att ccg ctt cca acg ccc tcg aga acg aac gtt gcg ctc     624
Leu Asp Ala Ile Pro Leu Pro Thr Pro Ser Arg Thr Asn Val Ala Leu
        195                 200                 205 ttt tcc tcc gca cag gtg ttc cct ctc aaa cac tac cag gac aag atc     672
Phe Ser Ser Ala Gln Val Phe Pro Leu Lys His Tyr Gln Asp Lys Ile
    210                 215                 220 cgg ccc tac gtc cag ctg ccc tcg cac cgc aac atc acc ggc gtg gtg     720
Arg Pro Tyr Val Gln Leu Pro Ser His Arg Asn Ile Thr Gly Val Val
225                 230                 235                 240 gag gtg atc ctc gga gac acc aag gcc tac gtg ttc ttc gag aag gac     768
Glu Val Ile Leu Gly Asp Thr Lys Ala Tyr Val Phe Phe Glu Lys Asp
                245                 250                 255 ttt ggg gac atg cac tcc tac gtg cgg agc tgt aag agg ctg agg gag     816
Phe Gly Asp Met His Ser Tyr Val Arg Ser Cys Lys Arg Leu Arg Glu
            260                 265                 270 gag gag gcc gcc cgg ctt ttc cgg cag att gtg gcg gcc gtc gct cac     864
Glu Glu Ala Ala Arg Leu Phe Arg Gln Ile Val Ala Ala Val Ala His
        275                 280                 285 tgc cac cag tcg gcc atc gtg ctc gga gac ctc aag ctc agg aaa ttt     912
Cys His Gln Ser Ala Ile Val Leu Gly Asp Leu Lys Leu Arg Lys Phe
    290                 295                 300 gtc ttc tcc aac gaa gag agg acg cag ctg agg ctg gag agc ctg gag     960
Val Phe Ser Asn Glu Glu Arg Thr Gln Leu Arg Leu Glu Ser Leu Glu
```

```
                305                 310                 315                 320
gac acg cac atc atc aag ggc gag gac gat gcg ctg tcg gat aag cac        1008
Asp Thr His Ile Ile Lys Gly Glu Asp Asp Ala Leu Ser Asp Lys His
                    325                 330                 335 ggc tgt ccc gct tac gtc agc ccc gag atc ctc aac acg acg ggg acg        1056
Gly Cys Pro Ala Tyr Val Ser Pro Glu Ile Leu Asn Thr Thr Gly Thr
                340                 345                 350 tac tcg ggg aag tcg gcc gac gtg tgg agt ttg gga gtg atg ctc tac        1104
Tyr Ser Gly Lys Ser Ala Asp Val Trp Ser Leu Gly Val Met Leu Tyr
            355                 360                 365 acc ctg ctc gtg gga cgc tat ccc ttc cac gac tcg gac cct agc act        1152
Thr Leu Leu Val Gly Arg Tyr Pro Phe His Asp Ser Asp Pro Ser Thr
        370                 375                 380 ctg ttt tcc aaa atc cgc cgc gga cag ttc tgt att ccc gac cac gtc        1200
Leu Phe Ser Lys Ile Arg Arg Gly Gln Phe Cys Ile Pro Asp His Val
385                 390                 395                 400 tcc ccc aaa gcc cga tgc ctc atc cgc agc ctc ctg cga cgg gag ccc        1248
Ser Pro Lys Ala Arg Cys Leu Ile Arg Ser Leu Leu Arg Arg Glu Pro
                    405                 410                 415 tct gaa aga ctc aca gcc ccg gag atc ctg ctc cat ccc tgg ttc gag        1296
Ser Glu Arg Leu Thr Ala Pro Glu Ile Leu Leu His Pro Trp Phe Glu
                420                 425                 430 gcg gtc ctg gag ccg gga tat tca gac cag gag acg gga act tcc gat        1344
Ala Val Leu Glu Pro Gly Tyr Ser Asp Gln Glu Thr Gly Thr Ser Asp
            435                 440                 445 caa atc gtt cca gaa tac cat gga gac aat gac gat atc agt tcc ttc        1392
Gln Ile Val Pro Glu Tyr His Gly Asp Asn Asp Asp Ile Ser Ser Phe
        450                 455                 460 ttc tgc taa                                                             1401
Phe Cys
465

<210> SEQ ID NO 10
<211> LENGTH: 466
<212> TYPE: PRT
<213> ORGANISM: Gallus gallus

<400> SEQUENCE: 10

Met Asp Pro Arg Cys Ser Val Ala His Arg Pro Gly Thr Asn Asp Ser
1               5                   10                  15

Ala Leu Leu His Ser Lys Asp Ala Pro Gly Lys His Val Ser Trp Asn
            20                  25                  30

Gly Lys Phe Leu Leu Ser Leu Ala Ala Lys Ala Leu Asn Gln Gly
        35                  40                  45

His Leu Ile Thr Thr Thr Ala Lys Leu Ser Val Ile Gln Glu Leu Phe
    50                  55                  60

Asn Thr Glu Ser Ser Asp Ser Ser Gln Phe Ile Tyr Asn Trp Pro
65                  70                  75                  80

Asn Pro Thr Glu Ser Leu Cys Val Ser His Thr His Cys Gln Ser
            85                  90                  95

Asn Gln Thr Cys Pro Lys His Arg Gly Ser Gly Glu Met Val Thr Gln
        100                 105                 110

Phe Pro Leu Pro Leu Ala Ala Pro Val Thr Glu Ile Lys Gly Gln Arg
    115                 120                 125

Ser Gly Ala Val Glu Thr Asp Asn Ser Val Ser Ile Met Gly Arg Ala
130                 135                 140

Ala Glu Leu Ala Val Leu Asp Phe Arg Ser Pro Ser Ser Val Arg Ser
145                 150                 155                 160
```

```
Glu Arg Arg Ser Arg Gly Gly Gly Ser Arg Ser Arg Ser Glu Arg Ser
                165                 170                 175

Thr Glu Pro Arg Arg Ser Ser Ile Pro Gly Val Val Trp Lys Glu Ser
            180                 185                 190

Leu Asp Ala Ile Pro Leu Pro Thr Pro Ser Arg Thr Asn Val Ala Leu
        195                 200                 205

Phe Ser Ser Ala Gln Val Phe Pro Leu Lys His Tyr Gln Asp Lys Ile
    210                 215                 220

Arg Pro Tyr Val Gln Leu Pro Ser His Arg Asn Ile Thr Gly Val Val
225                 230                 235                 240

Glu Val Ile Leu Gly Asp Thr Lys Ala Tyr Val Phe Phe Glu Lys Asp
                245                 250                 255

Phe Gly Asp Met His Ser Tyr Val Arg Ser Cys Lys Arg Leu Arg Glu
            260                 265                 270

Glu Glu Ala Ala Arg Leu Phe Arg Gln Ile Val Ala Ala Val Ala His
        275                 280                 285

Cys His Gln Ser Ala Ile Val Leu Gly Asp Leu Lys Leu Arg Lys Phe
    290                 295                 300

Val Phe Ser Asn Glu Glu Arg Thr Gln Leu Arg Leu Glu Ser Leu Glu
305                 310                 315                 320

Asp Thr His Ile Ile Lys Gly Glu Asp Ala Leu Ser Asp Lys His
                325                 330                 335

Gly Cys Pro Ala Tyr Val Ser Pro Glu Ile Leu Asn Thr Thr Gly Thr
            340                 345                 350

Tyr Ser Gly Lys Ser Ala Asp Val Trp Ser Leu Gly Val Met Leu Tyr
        355                 360                 365

Thr Leu Leu Val Gly Arg Tyr Pro Phe His Asp Ser Asp Pro Ser Thr
    370                 375                 380

Leu Phe Ser Lys Ile Arg Arg Gly Gln Phe Cys Ile Pro Asp His Val
385                 390                 395                 400

Ser Pro Lys Ala Arg Cys Leu Ile Arg Ser Leu Leu Arg Arg Glu Pro
                405                 410                 415

Ser Glu Arg Leu Thr Ala Pro Glu Ile Leu Leu His Pro Trp Phe Glu
            420                 425                 430

Ala Val Leu Glu Pro Gly Tyr Ser Asp Gln Glu Thr Gly Thr Ser Asp
        435                 440                 445

Gln Ile Val Pro Glu Tyr His Gly Asp Asn Asp Asp Ile Ser Ser Phe
    450                 455                 460

Phe Cys
465

<210> SEQ ID NO 11
<211> LENGTH: 1068
<212> TYPE: DNA
<213> ORGANISM: Xenopus laevis
<220> FEATURE:
<221> NAME/KEY: CDS
<222> LOCATION: (1)..(1068)

<400> SEQUENCE: 11 atg gtc gcc aac gtt ccg cgg cag agc cga ctg agt ccc ctc cgt ctg      48
Met Val Ala Asn Val Pro Arg Gln Ser Arg Leu Ser Pro Leu Arg Leu
1               5                   10                  15 gcc gtc tgt aga agc gcc tcc tcc aag cga ctg gag agc gac gaa ccc      96
Ala Val Cys Arg Ser Ala Ser Ser Lys Arg Leu Glu Ser Asp Glu Pro
            20                  25                  30 ccg gct aaa tgt ccc cgg ctc atc gac agc ccc acg gac aat ggc ttc     144
Pro Ala Lys Cys Pro Arg Leu Ile Asp Ser Pro Thr Asp Asn Gly Phe
```

```
              Pro Ala Lys Cys Pro Arg Leu Ile Asp Ser Pro Thr Asp Asn Gly Phe
                       35                  40                  45 ctg cct tcc ccc ggc tcc ccc cag ccc agc agc ccc cac gga acc aac       192
Leu Pro Ser Pro Gly Ser Pro Gln Pro Ser Ser Pro His Gly Thr Asn
 50                  55                  60 tgt cac ccg caa gga ccg acc tgt atc ggc aac tgc ctc ctg ctc ccc       240
Cys His Pro Gln Gly Pro Thr Cys Ile Gly Asn Cys Leu Leu Leu Pro
 65                  70                  75                  80 acc ggg ggc cga cag cac gtc tac cgg gct ctc cag ctg cat tcc ggg       288
Thr Gly Gly Arg Gln His Val Tyr Arg Ala Leu Gln Leu His Ser Gly
                     85                  90                  95 gcc gag ctg cag tgt aag gtt ttt cca tta aaa cac tac cag aag aaa       336
Ala Glu Leu Gln Cys Lys Val Phe Pro Leu Lys His Tyr Gln Lys Lys
                100                 105                 110 atc gag tct tac att cac ctg ccc tgg cac cgg aat atc acg ggg att       384
Ile Glu Ser Tyr Ile His Leu Pro Trp His Arg Asn Ile Thr Gly Ile
            115                 120                 125 gtg gaa gtc att cag ggg gac agc aag gcc tat gtg ttc ttt gag aag       432
Val Glu Val Ile Gln Gly Asp Ser Lys Ala Tyr Val Phe Phe Glu Lys
130                 135                 140 gat ttt ggg gac atg cac agt tac gtg cgc ggc tgt aag cgt ctc gga       480
Asp Phe Gly Asp Met His Ser Tyr Val Arg Gly Cys Lys Arg Leu Gly
145                 150                 155                 160 gaa gaa gaa gcc gcc aga ctg ttc cgc caa atc gtc agc gcc gtc tcc       528
Glu Glu Glu Ala Ala Arg Leu Phe Arg Gln Ile Val Ser Ala Val Ser
                165                 170                 175 cac tgc cat cga tct tca ata gtc ctc ggg gat ctt aaa ctc agg aag       576
His Cys His Arg Ser Ser Ile Val Leu Gly Asp Leu Lys Leu Arg Lys
            180                 185                 190 ttt gtg ttt gca gat aag gaa agg acg cag cta aga ctt gaa agc ttg       624
Phe Val Phe Ala Asp Lys Glu Arg Thr Gln Leu Arg Leu Glu Ser Leu
        195                 200                 205 gaa gac gcc cac atc atg aag gag aat gat gac tct ttg tcg gat aaa       672
Glu Asp Ala His Ile Met Lys Glu Asn Asp Asp Ser Leu Ser Asp Lys
210                 215                 220 cat ggc tgc ccg gct tac gtc agc cca gag att tta aac acc act ggg       720
His Gly Cys Pro Ala Tyr Val Ser Pro Glu Ile Leu Asn Thr Thr Gly
225                 230                 235                 240 act tac tct ggc aaa tcg gct gac gtg tgg agt cta ggg gtg atg ctg       768
Thr Tyr Ser Gly Lys Ser Ala Asp Val Trp Ser Leu Gly Val Met Leu
                245                 250                 255 tat act ctt tta gtg gga cgt tat cct ttt cat gac tct gac ccc agt       816
Tyr Thr Leu Leu Val Gly Arg Tyr Pro Phe His Asp Ser Asp Pro Ser
            260                 265                 270 gcc ctt ttt tcc aaa atc cgg cga ggg cag tac tgt att cct gac cat       864
Ala Leu Phe Ser Lys Ile Arg Arg Gly Gln Tyr Cys Ile Pro Asp His
        275                 280                 285 gta tcc ccc aaa gca agg tgc tta ata cgt agc ctg agg aag gag           912
Val Ser Pro Lys Ala Arg Cys Leu Ile Arg Ser Leu Leu Arg Lys Glu
290                 295                 300 ccc tct gag cga cta acg gcg gac gag att ttg ttg cac cct tgg ttt       960
Pro Ser Glu Arg Leu Thr Ala Asp Glu Ile Leu Leu His Pro Trp Phe
305                 310                 315                 320 gaa gct gct tct aat cca gga ttt gca gat cag gac aca agt agc agt      1008
Glu Ala Ala Ser Asn Pro Gly Phe Ala Asp Gln Asp Thr Ser Ser Ser
                325                 330                 335 gac caa ctt gtc ccg gac gtt ccc cag aac tgt gac aat ata gac tcc      1056
Asp Gln Leu Val Pro Asp Val Pro Gln Asn Cys Asp Asn Ile Asp Ser
            340                 345                 350 ttc ttc tgc taa                                                      1068
```

```
<210> SEQ ID NO 12
<211> LENGTH: 355
<212> TYPE: PRT
<213> ORGANISM: Xenopus laevis

<400> SEQUENCE: 12

Met Val Ala Asn Val Pro Arg Gln Ser Arg Leu Ser Pro Leu Arg Leu
1               5                   10                  15

Ala Val Cys Arg Ser Ala Ser Ser Lys Arg Leu Glu Ser Asp Glu Pro
            20                  25                  30

Pro Ala Lys Cys Pro Arg Leu Ile Asp Ser Pro Thr Asp Asn Gly Phe
        35                  40                  45

Leu Pro Ser Pro Gly Ser Pro Gln Pro Ser Ser Pro His Gly Thr Asn
    50                  55                  60

Cys His Pro Gln Gly Pro Thr Cys Ile Gly Asn Cys Leu Leu Leu Pro
65                  70                  75                  80

Thr Gly Gly Arg Gln His Val Tyr Arg Ala Leu Gln Leu His Ser Gly
                85                  90                  95

Ala Glu Leu Gln Cys Lys Val Phe Pro Leu Lys His Tyr Gln Lys Lys
            100                 105                 110

Ile Glu Ser Tyr Ile His Leu Pro Trp His Arg Asn Ile Thr Gly Ile
        115                 120                 125

Val Glu Val Ile Gln Gly Asp Ser Lys Ala Tyr Val Phe Phe Glu Lys
    130                 135                 140

Asp Phe Gly Asp Met His Ser Tyr Val Arg Gly Cys Lys Arg Leu Gly
145                 150                 155                 160

Glu Glu Glu Ala Ala Arg Leu Phe Arg Gln Ile Val Ser Ala Val Ser
                165                 170                 175

His Cys His Arg Ser Ser Ile Val Leu Gly Asp Leu Lys Leu Arg Lys
            180                 185                 190

Phe Val Phe Ala Asp Lys Glu Arg Thr Gln Leu Arg Leu Glu Ser Leu
        195                 200                 205

Glu Asp Ala His Ile Met Lys Glu Asn Asp Asp Ser Leu Ser Asp Lys
    210                 215                 220

His Gly Cys Pro Ala Tyr Val Ser Pro Glu Ile Leu Asn Thr Thr Gly
225                 230                 235                 240

Thr Tyr Ser Gly Lys Ser Ala Asp Val Trp Ser Leu Gly Val Met Leu
                245                 250                 255

Tyr Thr Leu Leu Val Gly Arg Tyr Pro Phe His Asp Ser Asp Pro Ser
            260                 265                 270

Ala Leu Phe Ser Lys Ile Arg Arg Gly Gln Tyr Cys Ile Pro Asp His
        275                 280                 285

Val Ser Pro Lys Ala Arg Cys Leu Ile Arg Ser Leu Leu Arg Lys Glu
    290                 295                 300

Pro Ser Glu Arg Leu Thr Ala Asp Glu Ile Leu Leu His Pro Trp Phe
305                 310                 315                 320

Glu Ala Ala Ser Asn Pro Gly Phe Ala Asp Gln Asp Thr Ser Ser Ser
                325                 330                 335

Asp Gln Leu Val Pro Asp Val Pro Gln Asn Cys Asp Asn Ile Asp Ser
            340                 345                 350

Phe Phe Cys
        355
```

-continued

<210> SEQ ID NO 13
<211> LENGTH: 1044
<212> TYPE: DNA
<213> ORGANISM: Apis mellifera
<220> FEATURE:
<221> NAME/KEY: CDS
<222> LOCATION: (1)..(1044)

<400> SEQUENCE: 13

```
atg aga gtg aca gcc gct gtc aga cag cat tct att cat cta caa gtg      48
Met Arg Val Thr Ala Ala Val Arg Gln His Ser Ile His Leu Gln Val
1               5                   10                  15 gct cga acc aac aat gga aag ttc ctg gtc tgc ccg aac aat aat cag      96
Ala Arg Thr Asn Asn Gly Lys Phe Leu Val Cys Pro Asn Asn Asn Gln
            20                  25                  30 gac atc agt caa cag cca acg aat gac gag acg aac tcg gtg cca gca     144
Asp Ile Ser Gln Gln Pro Thr Asn Asp Glu Thr Asn Ser Val Pro Ala
        35                  40                  45 gtt gtc ttc cct agt tat gaa cca ttg cct acc gat cat cat gga cct     192
Val Val Phe Pro Ser Tyr Glu Pro Leu Pro Thr Asp His His Gly Pro
    50                  55                  60 acc ata ctt ggc gat cgg tat cta ctt ctt gga cca gcc gag ggg agc     240
Thr Ile Leu Gly Asp Arg Tyr Leu Leu Leu Gly Pro Ala Glu Gly Ser
65                  70                  75                  80 gct cta tac cga tgc gtc gat gta cat tct ggt caa caa ctc gtc gca     288
Ala Leu Tyr Arg Cys Val Asp Val His Ser Gly Gln Gln Leu Val Ala
                85                  90                  95 aag gcg ctg acc gta ggc gat aaa ggt tgc gaa gca cta cta caa gct     336
Lys Ala Leu Thr Val Gly Asp Lys Gly Cys Glu Ala Leu Leu Gln Ala
            100                 105                 110 cac ctt cga tta gaa ggt act gga gcg gcg agc ggt gtc gca ggt gtg     384
His Leu Arg Leu Glu Gly Thr Gly Ala Ala Ser Gly Val Ala Gly Val
        115                 120                 125 gtg gaa gca cct gga ggt cga cgc tat ctc ctg ttg gag ggt cac cac     432
Val Glu Ala Pro Gly Gly Arg Arg Tyr Leu Leu Leu Glu Gly His His
    130                 135                 140 ggt gac ctg cac gcc tac gta agg gcg cgc agg aga ctg cgg gaa cca     480
Gly Asp Leu His Ala Tyr Val Arg Ala Arg Arg Arg Leu Arg Glu Pro
145                 150                 155                 160 gaa gcg agg cgg ctt ttc cgg caa gcg gcc aga gcc gtg gct acg tgt     528
Glu Ala Arg Arg Leu Phe Arg Gln Ala Ala Arg Ala Val Ala Thr Cys
                165                 170                 175 cac gag tat ggg gtc gtg ctt aga gac ctg aaa ctc agg aaa ttt gtt     576
His Glu Tyr Gly Val Val Leu Arg Asp Leu Lys Leu Arg Lys Phe Val
            180                 185                 190 ttc gcc gat gaa gca aga aca cga ctt cgt tta gaa agc ctg gaa gat     624
Phe Ala Asp Glu Ala Arg Thr Arg Leu Arg Leu Glu Ser Leu Glu Asp
        195                 200                 205 gca gta atc gtt gaa ggt gac aat gac aaa ctg act gat cga cgg ggt     672
Ala Val Ile Val Glu Gly Asp Asn Asp Lys Leu Thr Asp Arg Arg Gly
    210                 215                 220 tgc cca gcc tat gtg gca ccg gaa gta tta cgt tca gga cga gcc tat     720
Cys Pro Ala Tyr Val Ala Pro Glu Val Leu Arg Ser Gly Arg Ala Tyr
225                 230                 235                 240 tct ggc aaa gca gct gac atc tgg tca ctt ggt gta tta ctt tat aca     768
Ser Gly Lys Ala Ala Asp Ile Trp Ser Leu Gly Val Leu Leu Tyr Thr
                245                 250                 255 atg ttg gtc ggc cgt tat cca ttt aac gat gct gag cat gca tct ctg     816
Met Leu Val Gly Arg Tyr Pro Phe Asn Asp Ala Glu His Ala Ser Leu
            260                 265                 270 ttc gcg aaa atc tca cgt ggc caa ttc gca gta cca gaa ggt ctg agt     864
Phe Ala Lys Ile Ser Arg Gly Gln Phe Ala Val Pro Glu Gly Leu Ser
```

```
                Phe Ala Lys Ile Ser Arg Gly Gln Phe Ala Val Pro Glu Gly Leu Ser
                        275                 280                 285 cca cgt gct cga tgt ctg atc cgt tca ttg ctg aga aaa gaa ccg tcc         912
Pro Arg Ala Arg Cys Leu Ile Arg Ser Leu Leu Arg Lys Glu Pro Ser
        290                 295                 300 gag agg cca tac gcg gag gac gta ccg agg cat cca tgg ctt gca aaa         960
Glu Arg Pro Tyr Ala Glu Asp Val Pro Arg His Pro Trp Leu Ala Lys
305                 310                 315                 320 cca tta cga gtc tgt act aca tct agc agg tcc tca tgt cag gat caa        1008
Pro Leu Arg Val Cys Thr Thr Ser Ser Arg Ser Ser Cys Gln Asp Gln
                325                 330                 335 att gta cca gaa cta cct aat aat tct caa gac tga                        1044
Ile Val Pro Glu Leu Pro Asn Asn Ser Gln Asp
                340                 345

<210> SEQ ID NO 14
<211> LENGTH: 347
<212> TYPE: PRT
<213> ORGANISM: Apis mellifera

<400> SEQUENCE: 14

Met Arg Val Thr Ala Ala Val Arg Gln His Ser Ile His Leu Gln Val
1               5                   10                  15

Ala Arg Thr Asn Asn Gly Lys Phe Leu Val Cys Pro Asn Asn Asn Gln
            20                  25                  30

Asp Ile Ser Gln Gln Pro Thr Asn Asp Glu Thr Asn Ser Val Pro Ala
        35                  40                  45

Val Val Phe Pro Ser Tyr Glu Pro Leu Pro Thr Asp His His Gly Pro
    50                  55                  60

Thr Ile Leu Gly Asp Arg Tyr Leu Leu Gly Pro Ala Glu Gly Ser
65                  70                  75                  80

Ala Leu Tyr Arg Cys Val Asp Val His Ser Gly Gln Gln Leu Val Ala
                85                  90                  95

Lys Ala Leu Thr Val Gly Asp Lys Gly Cys Glu Ala Leu Leu Gln Ala
            100                 105                 110

His Leu Arg Leu Glu Gly Thr Gly Ala Ala Ser Gly Val Ala Gly Val
        115                 120                 125

Val Glu Ala Pro Gly Gly Arg Arg Tyr Leu Leu Glu Gly His His
    130                 135                 140

Gly Asp Leu His Ala Tyr Val Arg Ala Arg Arg Leu Arg Glu Pro
145                 150                 155                 160

Glu Ala Arg Arg Leu Phe Arg Gln Ala Ala Arg Ala Val Ala Thr Cys
                165                 170                 175

His Glu Tyr Gly Val Val Leu Arg Asp Leu Lys Leu Arg Lys Phe Val
            180                 185                 190

Phe Ala Asp Glu Ala Arg Thr Arg Leu Arg Leu Glu Ser Leu Glu Asp
        195                 200                 205

Ala Val Ile Val Glu Gly Asp Asn Asp Lys Leu Thr Asp Arg Arg Gly
    210                 215                 220

Cys Pro Ala Tyr Val Ala Pro Glu Val Leu Arg Ser Gly Arg Ala Tyr
225                 230                 235                 240

Ser Gly Lys Ala Ala Asp Ile Trp Ser Leu Gly Val Leu Leu Tyr Thr
                245                 250                 255

Met Leu Val Gly Arg Tyr Pro Phe Asn Asp Ala Glu His Ala Ser Leu
            260                 265                 270

Phe Ala Lys Ile Ser Arg Gly Gln Phe Ala Val Pro Glu Gly Leu Ser
        275                 280                 285
```

```
Pro Arg Ala Arg Cys Leu Ile Arg Ser Leu Leu Arg Lys Glu Pro Ser
    290                 295                 300

Glu Arg Pro Tyr Ala Glu Asp Val Pro Arg His Pro Trp Leu Ala Lys
305                 310                 315                 320

Pro Leu Arg Val Cys Thr Thr Ser Ser Arg Ser Ser Cys Gln Asp Gln
                325                 330                 335

Ile Val Pro Glu Leu Pro Asn Asn Ser Gln Asp
            340                 345

<210> SEQ ID NO 15
<211> LENGTH: 2345
<212> TYPE: PRT
<213> ORGANISM: Mus musculus

<400> SEQUENCE: 15

Met Asp Glu Pro Ser Pro Leu Ala Lys Thr Leu Glu Leu Asn Gln His
1               5                   10                  15

Ser Arg Phe Ile Ile Gly Ser Val Ser Glu Asp Asn Ser Glu Asp Glu
            20                  25                  30

Ile Ser Asn Leu Val Lys Leu Asp Leu Glu Glu Lys Glu Gly Ser Leu
        35                  40                  45

Ser Pro Ala Ser Val Ser Ser Asp Thr Leu Ser Asp Leu Gly Ile Ser
    50                  55                  60

Gly Leu Gln Asp Gly Leu Ala Phe His Met Arg Ser Ser Met Ser Gly
65              70                  75                  80

Leu His Leu Val Lys Gln Gly Arg Asp Arg Lys Lys Ile Asp Ser Gln
            85                  90                  95

Arg Asp Phe Thr Val Ala Ser Pro Ala Glu Phe Val Thr Arg Phe Gly
            100                 105                 110

Gly Asn Lys Val Ile Glu Lys Val Leu Ile Ala Asn Asn Gly Ile Ala
        115                 120                 125

Ala Val Lys Cys Met Arg Ser Ile Arg Arg Trp Ser Tyr Glu Met Phe
    130                 135                 140

Arg Asn Glu Arg Ala Ile Arg Phe Val Val Met Val Thr Pro Glu Asp
145                 150                 155                 160

Leu Lys Ala Asn Ala Glu Tyr Ile Lys Met Ala Asp His Tyr Val Pro
                165                 170                 175

Val Pro Gly Gly Pro Asn Asn Asn Asn Tyr Ala Asn Val Glu Leu Ile
            180                 185                 190

Leu Asp Ile Ala Lys Arg Ile Pro Val Gln Ala Val Trp Ala Gly Trp
        195                 200                 205

Gly His Ala Ser Glu Asn Pro Lys Leu Pro Glu Leu Leu Leu Lys Asn
    210                 215                 220

Gly Ile Ala Phe Met Gly Pro Pro Ser Gln Ala Met Trp Ala Leu Gly
225                 230                 235                 240

Asp Lys Ile Ala Ser Ser Ile Val Ala Gln Thr Ala Gly Ile Pro Thr
                245                 250                 255

Leu Pro Trp Ser Gly Ser Gly Leu Arg Val Asp Trp Gln Glu Asn Asp
            260                 265                 270

Phe Ser Lys Arg Ile Leu Asn Val Pro Gln Asp Leu Tyr Glu Lys Gly
        275                 280                 285

Tyr Val Lys Asp Val Asp Asp Gly Leu Lys Ala Ala Glu Glu Val Gly
    290                 295                 300

Tyr Pro Val Met Ile Lys Ala Ser Glu Gly Gly Gly Gly Lys Gly Ile
305                 310                 315                 320
```

```
Arg Lys Val Asn Asn Ala Asp Asp Phe Pro Asn Leu Phe Arg Gln Val
                325                 330                 335
Gln Ala Glu Val Pro Gly Ser Pro Ile Phe Val Met Arg Leu Ala Lys
            340                 345                 350
Gln Ser Arg His Leu Glu Val Gln Ile Leu Ala Asp Gln Tyr Gly Asn
        355                 360                 365
Ala Ile Ser Leu Phe Gly Arg Asp Cys Ser Val Gln Arg Arg His Gln
370                 375                 380
Lys Ile Ile Glu Glu Ala Pro Ala Ala Ile Ala Thr Pro Ala Val Phe
385                 390                 395                 400
Glu His Met Glu Gln Cys Ala Val Lys Leu Ala Lys Met Val Gly Tyr
                405                 410                 415
Val Ser Ala Gly Thr Val Glu Tyr Leu Tyr Ser Gln Asp Gly Ser Phe
            420                 425                 430
Tyr Phe Leu Glu Leu Asn Pro Arg Leu Gln Val Glu His Pro Cys Thr
        435                 440                 445
Glu Met Val Ala Asp Val Asn Leu Pro Ala Ala Gln Leu Gln Ile Ala
        450                 455                 460
Met Gly Ile Pro Leu Phe Arg Ile Lys Asp Ile Arg Met Met Tyr Gly
465                 470                 475                 480
Val Ser Pro Trp Gly Asp Ala Pro Ile Asp Phe Glu Asn Ser Ala His
                485                 490                 495
Val Pro Cys Pro Arg Gly His Val Ile Ala Ala Arg Ile Thr Ser Glu
            500                 505                 510
Asn Pro Asp Glu Gly Phe Lys Pro Ser Ser Gly Thr Val Gln Glu Leu
        515                 520                 525
Asn Phe Arg Ser Asn Lys Asn Val Trp Gly Tyr Phe Ser Val Ala Ala
        530                 535                 540
Ala Gly Gly Leu His Glu Phe Ala Asp Ser Gln Phe Gly His Cys Phe
545                 550                 555                 560
Ser Trp Gly Glu Asn Arg Glu Glu Ala Ile Ser Asn Met Val Val Ala
                565                 570                 575
Leu Lys Glu Leu Ser Ile Arg Gly Asp Phe Arg Thr Thr Val Glu Tyr
            580                 585                 590
Leu Ile Lys Leu Leu Glu Thr Glu Ser Phe Gln Leu Asn Arg Ile Asp
        595                 600                 605
Thr Gly Trp Leu Asp Arg Leu Ile Ala Glu Lys Val Gln Ala Gly Arg
        610                 615                 620
Pro Asp Thr Met Leu Gly Val Val Cys Gly Ala Leu His Val Ala Asp
625                 630                 635                 640
Val Ser Leu Arg Asn Ser Ile Ser Asn Phe Leu His Ser Leu Glu Arg
                645                 650                 655
Gly Gln Val Leu Pro Ala His Thr Leu Leu Asn Thr Val Asp Val Glu
            660                 665                 670
Leu Ile Tyr Glu Gly Ile Lys Tyr Val Leu Lys Val Thr Arg Gln Ser
        675                 680                 685
Pro Asn Ser Tyr Val Val Ile Met Asn Gly Ser Cys Val Glu Val Asp
        690                 695                 700
Val His Arg Leu Ser Asp Gly Gly Leu Leu Leu Ser Tyr Asp Gly Ser
705                 710                 715                 720
Ser Tyr Thr Thr Tyr Met Lys Glu Glu Val Asp Arg Tyr Arg Ile Thr
                725                 730                 735
Ile Gly Asn Lys Thr Cys Val Phe Glu Lys Glu Asn Asp Pro Ser Val
```

-continued

```
                    740                 745                 750
Met Arg Ser Pro Ser Ala Gly Lys Leu Ile Gln Tyr Ile Val Glu Asp
                755                 760                 765
Gly Gly His Val Phe Ala Gly Gln Cys Tyr Ala Glu Ile Glu Val Met
                770                 775                 780
Lys Met Val Met Thr Leu Thr Ala Val Glu Ser Gly Cys Ile His Tyr
785                 790                 795                 800
Val Lys Arg Pro Gly Ala Ala Leu Asp Pro Gly Cys Val Ile Ala Lys
                805                 810                 815
Met Gln Leu Asp Asn Pro Ser Lys Val Gln Gln Ala Glu Leu His Thr
                820                 825                 830
Gly Ser Leu Pro Gln Ile Gln Ser Thr Ala Leu Arg Gly Glu Lys Leu
                835                 840                 845
His Arg Val Phe His Tyr Val Leu Asp Asn Leu Val Asn Val Met Asn
                850                 855                 860
Gly Tyr Cys Leu Pro Asp Pro Phe Phe Ser Ser Arg Val Lys Asp Trp
865                 870                 875                 880
Val Glu Arg Leu Met Lys Thr Leu Arg Asp Pro Ser Leu Pro Leu Leu
                885                 890                 895
Glu Leu Gln Asp Ile Met Thr Ser Val Pro Gly Arg Ile Pro Leu Asn
                900                 905                 910
Val Glu Lys Ser Ile Lys Lys Glu Met Ala Gln Tyr Ala Ser Asn Ile
                915                 920                 925
Thr Ser Val Leu Tyr Gln Phe Pro Ser Gln Gln Ile Ala Asn Ile Leu
                930                 935                 940
Asp Ser His Ala Ala Thr Leu Asn Arg Lys Ser Glu Arg Glu Val Phe
945                 950                 955                 960
Phe Met Asn Thr Gln Ser Ile Val Gln Leu Val Gln Arg Tyr Arg Ser
                965                 970                 975
Gly Ile Arg Gly His Met Lys Ala Val Val Met Asp Leu Leu Arg Gln
                980                 985                 990
Tyr Leu Arg Val Glu Thr Gln Phe  Gln Asn Gly His Tyr  Asp Lys Cys
                995                 1000                1005
Val Phe Ala Leu Arg Glu Glu  Asn Lys Ser Asp Met  Asn Thr Val
    1010                1015                1020
Leu Asn Tyr Ile Phe Ser His  Ala Gln Val Thr Lys  Lys Asn Leu
    1025                1030                1035
Leu Val Thr Met Leu Ile Asp  Gln Leu Cys Gly Arg  Asp Pro Thr
    1040                1045                1050
Leu Thr Asp Glu Leu Leu Asn  Ile Leu Thr Glu Leu  Thr Gln Leu
    1055                1060                1065
Ser Lys Thr Thr Asn Ala Lys  Val Ala Leu Arg Ala  Arg Gln Val
    1070                1075                1080
Leu Ile Ala Ser His Leu Pro  Ser Tyr Glu Leu Arg  His Asn Gln
    1085                1090                1095
Val Glu Ser Ile Phe Leu Ser  Ala Ile Asp Met Tyr  Gly His Gln
    1100                1105                1110
Phe Cys Ile Glu Asn Leu Gln  Lys Leu Ile Leu Ser  Glu Thr Ser
    1115                1120                1125
Ile Phe Asp Val Leu Pro Asn  Phe Phe Tyr His Ser  Asn Gln Val
    1130                1135                1140
Val Arg Met Ala Ala Leu Glu  Val Tyr Val Arg Arg  Ala Tyr Ile
    1145                1150                1155
```

-continued

Ala Tyr Glu Leu Asn Ser Val Gln His Arg Gln Leu Lys Asp Asn
1160                1165                1170

Thr Cys Val Val Glu Phe Gln Phe Met Leu Pro Thr Ser His Pro
1175                1180                1185

Asn Arg Gly Asn Ile Pro Thr Leu Asn Arg Met Ser Phe Ala Ser
1190                1195                1200

Asn Leu Asn His Tyr Gly Met Thr His Val Ala Ser Val Ser Asp
1205                1210                1215

Val Leu Leu Asp Asn Ala Phe Thr Pro Pro Cys Gln Arg Met Gly
1220                1225                1230

Gly Met Val Ser Phe Arg Thr Phe Glu Asp Phe Val Arg Ile Phe
1235                1240                1245

Asp Glu Ile Met Gly Cys Phe Cys Asp Ser Pro Pro Gln Ser Pro
1250                1255                1260

Thr Phe Pro Glu Ser Gly His Thr Ser Leu Tyr Asp Glu Asp Lys
1265                1270                1275

Val Pro Arg Asp Glu Pro Ile His Ile Leu Asn Val Ala Ile Lys
1280                1285                1290

Thr Asp Gly Asp Ile Glu Asp Asp Arg Leu Ala Ala Met Phe Arg
1295                1300                1305

Glu Phe Thr Gln Gln Asn Lys Ala Thr Leu Val Glu His Gly Ile
1310                1315                1320

Arg Arg Leu Thr Phe Leu Val Ala Gln Lys Asp Phe Arg Lys Gln
1325                1330                1335

Val Asn Cys Glu Val Asp Gln Arg Phe His Arg Glu Phe Pro Lys
1340                1345                1350

Phe Phe Thr Phe Arg Ala Arg Asp Lys Phe Glu Glu Asp Arg Ile
1355                1360                1365

Tyr Arg His Leu Glu Pro Ala Leu Ala Phe Gln Leu Glu Leu Asn
1370                1375                1380

Arg Met Arg Asn Phe Asp Leu Thr Ala Ile Pro Cys Ala Asn His
1385                1390                1395

Lys Met His Leu Tyr Leu Gly Ala Ala Lys Val Glu Val Gly Thr
1400                1405                1410

Glu Val Thr Asp Tyr Arg Phe Phe Val Arg Ala Ile Ile Arg His
1415                1420                1425

Ser Asp Leu Val Thr Lys Glu Ala Ser Phe Glu Tyr Leu Gln Asn
1430                1435                1440

Glu Gly Glu Arg Leu Leu Leu Glu Ala Met Asp Glu Ser Glu Val
1445                1450                1455

Ala Phe Asn Asn Thr Asn Val Arg Thr Asp Cys Asn His Ile Phe
1460                1465                1470

Leu Asn Phe Val Pro Thr Val Ile Met Asp Pro Ser Lys Ile Glu
1475                1480                1485

Glu Ser Val Arg Ser Met Val Met Arg Tyr Gly Ser Arg Leu Trp
1490                1495                1500

Lys Leu Arg Val Leu Gln Ala Glu Leu Lys Ile Asn Ile Arg Leu
1505                1510                1515

Thr Thr Thr Gly Lys Ala Ile Pro Ile Arg Leu Phe Leu Thr Asn
1520                1525                1530

Glu Ser Gly Tyr Tyr Leu Asp Ile Ser Leu Tyr Lys Glu Val Thr
1535                1540                1545

Asp Ser Arg Thr Ala Gln Ile Met Phe Gln Ala Tyr Gly Asp Lys
1550                1555                1560

-continued

```
Gln Gly Pro Leu His Gly Met Leu Ile Asn Thr Pro Tyr Val Thr
    1565            1570            1575

Lys Asp Leu Leu Gln Ser Lys Arg Phe Gln Ala Gln Ser Leu Gly
    1580            1585            1590

Thr Thr Tyr Ile Tyr Asp Ile Pro Glu Met Phe Arg Gln Ser Leu
    1595            1600            1605

Ile Lys Leu Trp Glu Ser Met Ser Thr Gln Ala Phe Leu Pro Ser
    1610            1615            1620

Pro Pro Leu Pro Ser Asp Ile Leu Thr Tyr Thr Glu Leu Val Leu
    1625            1630            1635

Asp Asp Gln Gly Gln Leu Val His Met Asn Arg Leu Pro Gly Gly
    1640            1645            1650

Asn Glu Ile Gly Met Val Ala Trp Lys Met Ser Leu Lys Ser Pro
    1655            1660            1665

Glu Tyr Pro Asp Gly Arg Asp Ile Ile Val Ile Gly Asn Asp Ile
    1670            1675            1680

Thr Tyr Arg Ile Gly Ser Phe Gly Pro Gln Glu Asp Leu Leu Phe
    1685            1690            1695

Leu Arg Ala Ser Glu Leu Ala Arg Ala Glu Gly Ile Pro Arg Ile
    1700            1705            1710

Tyr Val Ala Ala Asn Ser Gly Ala Arg Ile Gly Leu Ala Glu Glu
    1715            1720            1725

Ile Arg His Met Phe His Val Ala Trp Val Asp Pro Glu Asp Pro
    1730            1735            1740

Tyr Lys Gly Tyr Lys Tyr Leu Tyr Leu Thr Pro Gln Asp Tyr Lys
    1745            1750            1755

Arg Val Ser Ala Leu Asn Ser Val His Cys Glu His Val Glu Asp
    1760            1765            1770

Glu Gly Glu Ser Arg Tyr Lys Ile Thr Asp Ile Ile Gly Lys Glu
    1775            1780            1785

Glu Gly Leu Gly Ala Glu Asn Leu Arg Gly Ser Gly Met Ile Ala
    1790            1795            1800

Gly Glu Ser Ser Leu Ala Tyr Asp Glu Val Ile Thr Ile Ser Leu
    1805            1810            1815

Val Thr Cys Arg Ala Ile Gly Ile Gly Ala Tyr Leu Val Arg Leu
    1820            1825            1830

Gly Gln Arg Thr Ile Gln Val Glu Asn Ser His Leu Ile Leu Thr
    1835            1840            1845

Gly Ala Gly Ala Leu Asn Lys Val Leu Gly Arg Glu Val Tyr Thr
    1850            1855            1860

Ser Asn Asn Gln Leu Gly Gly Ile Gln Ile Met His Asn Asn Gly
    1865            1870            1875

Val Thr His Ser Thr Val Cys Asp Asp Phe Glu Gly Val Phe Thr
    1880            1885            1890

Val Leu His Trp Leu Ser Tyr Met Pro Lys Ser Val His Ser Ser
    1895            1900            1905

Val Pro Leu Leu Asn Ser Lys Asp Pro Ile Asp Arg Ile Ile Glu
    1910            1915            1920

Phe Val Pro Thr Lys Ala Pro Tyr Asp Pro Arg Trp Met Leu Ala
    1925            1930            1935

Gly Arg Pro His Pro Thr Gln Lys Gly Gln Trp Leu Ser Gly Phe
    1940            1945            1950

Phe Asp Tyr Gly Ser Phe Ser Glu Ile Met Gln Pro Trp Ala Gln
```

```
                1955                1960                1965
Thr Val Val Val Gly Arg Ala Arg Leu Gly Gly Ile Pro Val Gly
    1970                1975                1980

Val Val Ala Val Glu Thr Arg Thr Val Glu Leu Gly Ile Pro Ala
    1985                1990                1995

Asp Pro Ala Asn Leu Asp Ser Glu Ala Lys Ile Ile Gln Gln Ala
    2000                2005                2010

Gly Gln Val Trp Phe Pro Asp Ser Ala Phe Lys Thr Tyr Gln Ala
    2015                2020                2025

Ile Lys Asp Phe Asn Arg Glu Gly Leu Pro Leu Met Val Phe Ala
    2030                2035                2040

Asn Trp Arg Gly Phe Ser Gly Gly Met Lys Asp Met Tyr Asp Gln
    2045                2050                2055

Val Leu Lys Phe Gly Ala Tyr Ile Val Asp Gly Leu Arg Glu Cys
    2060                2065                2070

Ser Gln Pro Ile Met Val Tyr Ile Pro Pro Gln Ala Glu Leu Arg
    2075                2080                2085

Gly Gly Ser Trp Val Val Ile Asp Pro Thr Ile Asn Pro Arg His
    2090                2095                2100

Met Glu Met Tyr Ala Asp Arg Glu Ser Arg Gly Ser Val Leu Glu
    2105                2110                2115

Pro Glu Gly Thr Val Glu Ile Lys Phe Arg Lys Lys Asp Leu Val
    2120                2125                2130

Lys Thr Met Arg Arg Val Asp Pro Val Tyr Ile Arg Leu Ala Glu
    2135                2140                2145

Arg Leu Gly Thr Pro Glu Leu Ser Pro Thr Glu Arg Lys Glu Leu
    2150                2155                2160

Glu Ser Lys Leu Lys Lys Arg Glu Glu Phe Leu Ile Pro Ile Tyr
    2165                2170                2175

His Gln Val Ala Val Gln Phe Ala Asp Leu His Asp Thr Pro Gly
    2180                2185                2190

Arg Met Gln Glu Lys Gly Val Ile Asn Asp Ile Leu Asp Trp Lys
    2195                2200                2205

Thr Ser Arg Thr Phe Phe Tyr Trp Arg Leu Arg Arg Leu Leu Leu
    2210                2215                2220

Glu Asp Leu Val Lys Lys Lys Ile His Asn Ala Asn Pro Glu Leu
    2225                2230                2235

Thr Asp Gly Gln Ile Gln Ala Met Leu Arg Arg Trp Ser Val Glu
    2240                2245                2250

Val Glu Gly Ala Val Lys Ala Tyr Val Trp Asp Asn Asn Lys Asp
    2255                2260                2265

Leu Val Glu Trp Leu Glu Lys Gln Leu Thr Glu Glu Asp Gly Val
    2270                2275                2280

Arg Ser Val Ile Glu Glu Asn Ile Lys Tyr Ile Ser Arg Asp Tyr
    2285                2290                2295

Val Leu Lys Gln Ile Arg Ser Leu Val Gln Ala Asn Pro Glu Val
    2300                2305                2310

Ala Met Asp Ser Ile Val His Met Thr Gln His Ile Ser Pro Thr
    2315                2320                2325

Gln Arg Ala Glu Val Val Arg Ile Leu Ser Thr Met Asp Ser Pro
    2330                2335                2340

Ser Thr
    2345
```

<210> SEQ ID NO 16
<211> LENGTH: 2448
<212> TYPE: PRT
<213> ORGANISM: Mus musculus

<400> SEQUENCE: 16

Met Val Leu Leu Leu Phe Leu Thr Cys Leu Val Phe Ser Cys Leu Thr
1               5                   10                  15

Phe Ser Trp Leu Lys Ile Trp Gly Lys Met Thr Asp Ser Lys Pro Leu
            20                  25                  30

Thr Asn Ser Lys Val Glu Ala Asn Leu Leu Ser Ser Glu Glu Ser Leu
        35                  40                  45

Ser Ala Ser Glu Leu Ser Gly Glu Gln Leu Gln Glu His Gly Asp His
    50                  55                  60

Ser Cys Leu Ser Tyr Arg Gly Pro Arg Asp Ala Ser Gln Gln Arg Asn
65                  70                  75                  80

Ser Leu Pro Ser Ser Cys Gln Arg Pro Pro Arg Asn Pro Leu Ser Ser
                85                  90                  95

Asn Asp Thr Trp Pro Ser Pro Glu Leu Gln Thr Asn Trp Thr Ala Ala
            100                 105                 110

Pro Gly Pro Glu Val Pro Asp Ala Asn Gly Leu Pro Phe Pro Ala Arg
        115                 120                 125

Pro Pro Ser Gln Arg Thr Val Ser Pro Ser Arg Glu Asp Arg Lys Gln
    130                 135                 140

Ala His Ile Lys Arg Gln Leu Met Thr Ser Phe Ile Leu Gly Ser Leu
145                 150                 155                 160

Asp Asp Asn Ser Ser Asp Glu Asp Pro Ser Ala Gly Ser Phe Gln Asn
                165                 170                 175

Ser Ser Arg Lys Ser Ser Arg Ala Ser Leu Gly Thr Leu Ser Gln Glu
            180                 185                 190

Ala Ala Leu Asn Thr Ser Asp Pro Glu Ser His Ala Pro Thr Met Arg
        195                 200                 205

Pro Ser Met Ser Gly Leu His Leu Val Lys Arg Gly Arg Glu His Lys
    210                 215                 220

Lys Leu Asp Leu His Arg Asp Phe Thr Val Ala Ser Pro Ala Glu Phe
225                 230                 235                 240

Val Thr Arg Phe Gly Gly Asn Arg Val Ile Glu Lys Val Leu Ile Ala
                245                 250                 255

Asn Asn Gly Ile Ala Ala Val Lys Cys Met Arg Ser Ile Arg Arg Trp
            260                 265                 270

Ala Tyr Glu Met Phe Arg Asn Glu Arg Ala Ile Arg Phe Val Val Met
        275                 280                 285

Val Thr Pro Glu Asp Leu Lys Ala Asn Ala Glu Tyr Ile Lys Met Ala
    290                 295                 300

Asp Gln Tyr Val Pro Val Pro Gly Gly Pro Asn Asn Asn Asn Tyr Ala
305                 310                 315                 320

Asn Val Glu Leu Ile Ile Asp Ile Ala Lys Arg Ile Pro Val Gln Ala
                325                 330                 335

Val Trp Ala Gly Trp Gly His Ala Ser Glu Asn Pro Lys Leu Pro Glu
            340                 345                 350

Leu Leu Cys Lys His Glu Ile Ala Phe Leu Gly Pro Pro Ser Glu Ala
        355                 360                 365

Met Trp Ala Leu Gly Asp Lys Ile Ala Ser Thr Ile Val Ala Gln Thr
    370                 375                 380

```
Leu Gln Ile Pro Thr Leu Pro Trp Ser Gly Ser Gly Leu Thr Val Glu
385                 390                 395                 400

Trp Thr Glu Asp Ser Arg His Gln Gly Lys Cys Ile Ser Val Pro Glu
                405                 410                 415

Asp Val Tyr Glu Gln Gly Cys Val Lys Asp Val Asp Glu Gly Leu Gln
            420                 425                 430

Ala Ala Glu Lys Ile Gly Phe Pro Leu Met Ile Lys Ala Ser Glu Gly
        435                 440                 445

Gly Gly Gly Lys Gly Ile Arg Lys Ala Glu Ser Ala Glu Asp Phe Pro
    450                 455                 460

Met Leu Phe Arg Gln Val Gln Ser Glu Ile Pro Gly Ser Pro Ile Phe
465                 470                 475                 480

Leu Met Lys Leu Ala Gln Asn Ala Arg His Leu Glu Val Gln Val Leu
                485                 490                 495

Ala Asp Gln Tyr Gly Asn Ala Val Ser Leu Phe Gly Arg Asp Cys Ser
            500                 505                 510

Ile Gln Arg Arg His Gln Lys Ile Ile Glu Glu Ala Pro Ala Thr Ile
        515                 520                 525

Ala Ala Pro Ala Val Ser Glu Phe Met Glu Gln Cys Ala Val Leu Leu
530                 535                 540

Ala Lys Met Val Gly Tyr Val Ser Ala Gly Thr Val Glu Tyr Leu Tyr
545                 550                 555                 560

Ser Arg Asp Gly Ser Phe His Phe Leu Glu Leu Asn Pro Arg Leu Gln
                565                 570                 575

Val Glu His Pro Cys Thr Glu Met Ile Ala Asp Val Asn Leu Pro Ala
            580                 585                 590

Ala Gln Leu Gln Ile Ala Met Gly Val Pro Leu His Arg Leu Lys Asp
        595                 600                 605

Ile Arg Leu Leu Tyr Gly Glu Ser Pro Trp Gly Val Thr Pro Ile Pro
610                 615                 620

Phe Glu Thr Pro Leu Ser Pro Pro Ile Ala Arg Gly His Val Ile Ala
625                 630                 635                 640

Ala Arg Ile Thr Ser Glu Asn Pro Asp Glu Gly Phe Lys Pro Ser Ser
                645                 650                 655

Gly Thr Val Gln Glu Leu Asn Phe Arg Ser Asn Lys Asn Val Trp Gly
            660                 665                 670

Tyr Phe Ser Val Ala Ala Ala Gly Gly Leu His Glu Phe Ala Asp Ser
        675                 680                 685

Gln Phe Gly His Cys Phe Ser Trp Gly Glu Asn Arg Glu Glu Ala Ile
690                 695                 700

Ser Asn Met Val Val Ala Leu Lys Glu Leu Ser Ile Arg Gly Asp Phe
705                 710                 715                 720

Arg Thr Thr Val Glu Tyr Leu Val Asn Leu Leu Glu Thr Glu Ser Phe
                725                 730                 735

Gln Asn Asn Asp Ile Asp Thr Gly Trp Leu Asp His Leu Ile Ala Gln
            740                 745                 750

Arg Val Gln Ala Glu Lys Pro Asp Ile Met Leu Gly Val Val Cys Gly
        755                 760                 765

Ala Leu Asn Val Ala Asp Ala Met Phe Arg Thr Cys Met Thr Glu Phe
770                 775                 780

Leu His Ser Leu Glu Arg Gly Gln Val Leu Pro Ala Asp Ser Leu Leu
785                 790                 795                 800

Asn Ile Val Asp Val Glu Leu Ile Tyr Gly Gly Ile Lys Tyr Ala Leu
                805                 810                 815
```

```
Lys Val Ala Arg Gln Ser Leu Thr Met Phe Val Leu Ile Met Asn Gly
            820                 825                 830

Cys His Ile Glu Ile Asp Ala His Arg Leu Asn Asp Gly Gly Leu Leu
            835                 840                 845

Leu Ser Tyr Asn Gly Ser Ser Tyr Thr Thr Tyr Met Lys Glu Val
            850                 855                 860

Asp Ser Tyr Arg Ile Thr Ile Gly Asn Lys Thr Cys Val Phe Glu Lys
865                 870                 875                 880

Glu Asn Asp Pro Thr Val Leu Arg Ser Pro Ser Ala Gly Lys Leu Met
                885                 890                 895

Gln Tyr Thr Val Glu Asp Gly Asp His Val Glu Ala Gly Ser Ser Tyr
                900                 905                 910

Ala Glu Met Glu Val Met Lys Met Ile Met Thr Leu Asn Val Gln Glu
            915                 920                 925

Ser Gly Arg Val Lys Tyr Ile Lys Arg Pro Gly Val Ile Leu Glu Ala
            930                 935                 940

Gly Cys Val Val Ala Arg Leu Glu Leu Asp Asp Pro Ser Lys Val His
945                 950                 955                 960

Ala Ala Gln Pro Phe Thr Gly Glu Leu Pro Ala Gln Thr Leu Pro
                965                 970                 975

Ile Leu Gly Glu Lys Leu His Gln Val Phe His Gly Val Leu Glu Asn
                980                 985                 990

Leu Thr Asn Val Met Ser Gly Tyr Cys Leu Pro Glu Pro Phe Phe Ser
            995                 1000                1005

Met Lys Leu Lys Asp Trp Val Gln Lys Leu Met Met Thr Leu Arg
    1010                1015                1020

His Pro Ser Leu Pro Leu Leu Glu Leu Gln Glu Ile Met Thr Ser
    1025                1030                1035

Val Ala Gly Arg Ile Pro Ala Pro Val Glu Lys Ala Val Arg Arg
    1040                1045                1050

Val Met Ala Gln Tyr Ala Ser Asn Ile Thr Ser Val Leu Cys Gln
    1055                1060                1065

Phe Pro Ser Gln Gln Ile Ala Thr Ile Leu Asp Cys His Ala Ala
    1070                1075                1080

Thr Leu Gln Arg Lys Ala Asp Arg Glu Val Phe Phe Met Asn Thr
    1085                1090                1095

Gln Ser Ile Val Gln Leu Val Gln Arg Tyr Arg Ser Gly Thr Arg
    1100                1105                1110

Gly Tyr Met Lys Ala Val Val Leu Asp Leu Leu Arg Lys Tyr Leu
    1115                1120                1125

Asn Val Glu His His Phe Gln Gln Ala His Tyr Asp Lys Cys Val
    1130                1135                1140

Ile Asn Leu Arg Glu Gln Phe Lys Pro Asp Met Thr Gln Val Leu
    1145                1150                1155

Asp Cys Ile Phe Ser His Ser Gln Val Ala Lys Lys Asn Gln Leu
    1160                1165                1170

Val Thr Met Leu Ile Asp Glu Leu Cys Gly Pro Asp Pro Thr Leu
    1175                1180                1185

Ser Asp Glu Leu Thr Ser Ile Leu Cys Glu Leu Thr Gln Leu Ser
    1190                1195                1200

Arg Ser Glu His Cys Lys Val Ala Leu Arg Ala Arg Gln Val Leu
    1205                1210                1215

Ile Ala Ser His Leu Pro Ser Tyr Glu Leu Arg His Asn Gln Val
```

```
              1220             1225             1230
Glu Ser Ile Phe Leu Ser Ala Ile Asp Met Tyr Gly His Gln Phe
    1235             1240             1245
Cys Pro Glu Asn Leu Lys Lys Leu Ile Leu Ser Glu Thr Thr Ile
    1250             1255             1260
Phe Asp Val Leu Pro Thr Phe Phe Tyr His Glu Asn Lys Val Val
    1265             1270             1275
Cys Met Ala Ser Leu Glu Val Tyr Val Arg Arg Gly Tyr Ile Ala
    1280             1285             1290
Tyr Glu Leu Asn Ser Leu Gln His Arg Glu Leu Pro Asp Gly Thr
    1295             1300             1305
Cys Val Val Glu Phe Gln Ser Met Leu Pro Ser Ser His Pro Asn
    1310             1315             1320
Arg Met Ala Val Pro Ile Ser Val Ser Asn Pro Asp Leu Leu Arg
    1325             1330             1335
His Ser Thr Glu Leu Phe Met Asp Ser Gly Phe Ser Pro Leu Cys
    1340             1345             1350
Gln Arg Met Gly Ala Met Val Ala Phe Arg Arg Phe Glu Glu Phe
    1355             1360             1365
Thr Arg Asn Phe Asp Glu Val Ile Ser Cys Phe Ala Asn Val Gln
    1370             1375             1380
Thr Asp Thr Leu Leu Phe Ser Lys Ala Cys Thr Ser Leu Tyr Ser
    1385             1390             1395
Glu Glu Asp Asn Lys Ser Leu Arg Glu Glu Pro Ile His Ile Leu
    1400             1405             1410
Asn Val Ala Ile Gln Cys Ala Asp His Met Glu Asp Glu Ala Leu
    1415             1420             1425
Val Pro Val Phe Arg Ala Phe Val Gln Ser Lys Lys His Ile Leu
    1430             1435             1440
Val Asp Tyr Gly Leu Arg Arg Ile Thr Phe Leu Val Ala Gln Glu
    1445             1450             1455
Arg Glu Phe Pro Lys Phe Phe Thr Phe Arg Ala Arg Asp Glu Phe
    1460             1465             1470
Ala Glu Asp Arg Ile Tyr Arg His Leu Glu Pro Ala Leu Ala Phe
    1475             1480             1485
Gln Leu Glu Leu Ser Arg Met Arg Asn Phe Asp Leu Thr Ala Val
    1490             1495             1500
Pro Cys Ala Asn His Lys Met His Leu Tyr Leu Gly Ala Ala Lys
    1505             1510             1515
Val Lys Glu Gly Leu Glu Val Thr Asp His Arg Phe Phe Ile Arg
    1520             1525             1530
Ala Ile Ile Arg His Ser Asp Leu Ile Thr Lys Glu Ala Ser Phe
    1535             1540             1545
Glu Tyr Leu Gln Asn Glu Gly Glu Arg Leu Leu Leu Glu Ala Met
    1550             1555             1560
Asp Glu Leu Glu Val Ala Phe Asn Asn Thr Ser Val Arg Thr Asp
    1565             1570             1575
Cys Asn His Ile Phe Leu Asn Phe Val Pro Thr Val Ile Met Asp
    1580             1585             1590
Pro Leu Lys Ile Glu Glu Ser Val Arg Asp Met Val Met Arg Tyr
    1595             1600             1605
Gly Ser Arg Leu Trp Lys Leu Arg Val Leu Gln Ala Glu Val Lys
    1610             1615             1620
```

-continued

Ile Asn Ile Arg Gln Thr Thr Ser Asp Ser Ala Ile Pro Ile Arg
1625                1630                1635

Leu Phe Ile Thr Asn Glu Ser Gly Tyr Tyr Leu Asp Ile Ser Leu
1640                1645                1650

Tyr Arg Glu Val Thr Asp Ser Arg Ser Gly Asn Ile Met Phe His
1655                1660                1665

Ser Phe Gly Asn Lys Gln Gly Ser Leu His Gly Met Leu Ile Asn
1670                1675                1680

Thr Pro Tyr Val Thr Lys Asp Leu Leu Gln Ala Lys Arg Phe Gln
1685                1690                1695

Ala Gln Ser Leu Gly Thr Thr Tyr Val Tyr Asp Phe Pro Glu Met
1700                1705                1710

Phe Arg Gln Ala Leu Phe Lys Leu Trp Gly Ser Pro Glu Lys Tyr
1715                1720                1725

Pro Lys Asp Ile Leu Thr Tyr Thr Glu Leu Val Leu Asp Ser Gln
1730                1735                1740

Gly Gln Leu Val Glu Met Asn Arg Leu Pro Gly Cys Asn Glu Val
1745                1750                1755

Gly Met Val Ala Phe Lys Met Arg Phe Lys Thr Pro Glu Tyr Pro
1760                1765                1770

Glu Gly Arg Asp Ala Val Val Ile Gly Asn Asp Ile Thr Phe Gln
1775                1780                1785

Ile Gly Ser Phe Gly Ile Gly Glu Asp Phe Leu Tyr Leu Arg Ala
1790                1795                1800

Ser Glu Met Ala Arg Thr Glu Gly Ile Pro Gln Ile Tyr Leu Ala
1805                1810                1815

Ala Asn Ser Gly Ala Arg Met Gly Leu Ala Glu Glu Ile Lys Gln
1820                1825                1830

Ile Phe Gln Val Ala Trp Val Asp Pro Glu Asp Pro His Lys Gly
1835                1840                1845

Phe Arg Tyr Leu Tyr Leu Thr Pro Gln Asp Tyr Thr Gln Ile Ser
1850                1855                1860

Ser Gln Asn Ser Val His Cys Lys His Ile Glu Asp Glu Gly Glu
1865                1870                1875

Ser Arg Tyr Val Ile Val Asp Val Ile Gly Lys Asp Ala Asn Leu
1880                1885                1890

Gly Val Glu Asn Leu Arg Gly Ser Gly Met Ile Ala Gly Glu Ala
1895                1900                1905

Ser Leu Ala Tyr Glu Lys Thr Val Thr Ile Ser Met Val Thr Cys
1910                1915                1920

Arg Ala Leu Gly Ile Gly Ala Tyr Leu Val Arg Leu Gly Gln Arg
1925                1930                1935

Val Ile Gln Val Glu Asn Ser His Ile Ile Leu Thr Gly Ala Gly
1940                1945                1950

Ala Leu Asn Lys Val Leu Gly Arg Glu Val Tyr Thr Ser Asn Asn
1955                1960                1965

Gln Leu Gly Gly Val Gln Ile Met His Thr Asn Gly Val Ser His
1970                1975                1980

Val Thr Val Pro Asp Asp Phe Glu Gly Val Cys Thr Ile Leu Glu
1985                1990                1995

Trp Leu Ser Phe Ile Pro Lys Asp Asn Arg Ser Pro Val Pro Ile
2000                2005                2010

Thr Thr Pro Ser Asp Pro Ile Asp Arg Glu Ile Glu Phe Thr Pro
2015                2020                2025

```
Thr Lys Ala Pro Tyr Asp Pro Arg Trp Met Leu Ala Gly Arg Pro
    2030            2035                2040

His Pro Thr Leu Lys Gly Thr Trp Gln Ser Gly Phe Phe Asp His
    2045            2050                2055

Gly Ser Phe Lys Glu Ile Met Ala Pro Trp Ala Gln Thr Val Val
    2060            2065                2070

Thr Gly Arg Ala Arg Leu Gly Gly Ile Pro Val Gly Val Ile Ala
    2075            2080                2085

Val Glu Thr Arg Thr Val Glu Val Ala Val Pro Ala Asp Pro Ala
    2090            2095                2100

Asn Leu Asp Ser Glu Ala Lys Ile Ile Gln Gln Ala Gly Gln Val
    2105            2110                2115

Trp Phe Pro Asp Ser Ala Tyr Lys Thr Ala Gln Val Ile Arg Asp
    2120            2125                2130

Phe Asn Lys Glu Arg Leu Pro Leu Met Ile Phe Ala Asn Trp Arg
    2135            2140                2145

Gly Phe Ser Gly Gly Met Lys Asp Met Tyr Glu Gln Met Leu Lys
    2150            2155                2160

Phe Gly Ala Tyr Ile Val Asp Gly Leu Arg Leu Tyr Glu Gln Pro
    2165            2170                2175

Ile Leu Ile Tyr Ile Pro Pro Cys Ala Glu Leu Arg Gly Gly Ser
    2180            2185                2190

Trp Val Val Leu Asp Ser Thr Ile Asn Pro Leu Cys Ile Glu Met
    2195            2200                2205

Tyr Ala Asp Lys Glu Ser Arg Gly Gly Val Leu Glu Pro Glu Gly
    2210            2215                2220

Thr Val Glu Ile Lys Phe Arg Lys Lys Asp Leu Val Lys Thr Ile
    2225            2230                2235

Arg Arg Ile Asp Pro Val Cys Lys Lys Leu Val Gly Gln Leu Gly
    2240            2245                2250

Lys Ala Gln Leu Pro Asp Lys Asp Arg Lys Glu Leu Glu Gly Gln
    2255            2260                2265

Leu Lys Ala Arg Glu Glu Leu Leu Leu Pro Ile Tyr His Gln Val
    2270            2275                2280

Ala Val Gln Phe Ala Asp Leu His Asp Thr Pro Gly His Met Leu
    2285            2290                2295

Glu Lys Gly Ile Ile Ser Asp Val Leu Glu Trp Lys Thr Ala Arg
    2300            2305                2310

Thr Phe Phe Tyr Trp Arg Leu Arg Arg Leu Leu Leu Glu Ala Gln
    2315            2320                2325

Val Lys Gln Glu Ile Leu Arg Ala Ser Pro Glu Leu Ser His Glu
    2330            2335                2340

His Thr Gln Ser Met Leu Arg Arg Trp Phe Val Glu Thr Glu Gly
    2345            2350                2355

Ala Val Lys Ala Tyr Leu Trp Asp Ser Asn Gln Val Val Val Gln
    2360            2365                2370

Trp Leu Glu Gln His Trp Ser Ala Lys Asp Gly Leu Arg Ser Thr
    2375            2380                2385

Ile Arg Glu Asn Ile Asn Tyr Leu Lys Arg Asp Ser Val Leu Lys
    2390            2395                2400

Thr Ile Gln Ser Leu Val Gln Glu His Pro Glu Val Ile Met Asp
    2405            2410                2415

Cys Val Ala Tyr Leu Ser Gln His Leu Thr Pro Ala Glu Arg Ile
```

```
                2420                2425                2430
        Gln Val Ala Gln Leu Leu Ser Thr Thr Glu Ser Pro Ala Ser Ser
            2435                2440                2445

<210> SEQ ID NO 17
<211> LENGTH: 2383
<212> TYPE: PRT
<213> ORGANISM: Homo sapiens

<400> SEQUENCE: 17

Met Trp Trp Ser Thr Leu Met Ser Ile Leu Arg Ala Arg Ser Phe Trp
1               5                   10                  15

Lys Trp Ile Ser Thr Gln Thr Val Arg Ile Ile Arg Ala Val Arg Ala
            20                  25                  30

His Phe Gly Gly Ile Met Asp Glu Pro Ser Pro Leu Ala Gln Pro Leu
        35                  40                  45

Glu Leu Asn Gln His Ser Arg Phe Ile Ile Gly Ser Val Ser Glu Asp
    50                  55                  60

Asn Ser Glu Asp Glu Ile Ser Asn Leu Val Lys Leu Asp Leu Leu Glu
65                  70                  75                  80

Glu Lys Glu Gly Ser Leu Ser Pro Ala Ser Val Gly Ser Asp Thr Leu
                85                  90                  95

Ser Asp Leu Gly Ile Ser Ser Leu Gln Asp Gly Leu Ala Leu His Ile
            100                 105                 110

Arg Ser Ser Met Ser Gly Leu His Leu Val Lys Gln Gly Arg Asp Arg
        115                 120                 125

Lys Lys Ile Asp Ser Gln Arg Asp Phe Thr Val Ala Ser Pro Ala Glu
    130                 135                 140

Phe Val Thr Arg Phe Gly Gly Asn Lys Val Ile Glu Lys Val Leu Ile
145                 150                 155                 160

Ala Asn Asn Gly Ile Ala Ala Val Lys Cys Met Arg Ser Ile Arg Arg
                165                 170                 175

Trp Ser Tyr Glu Met Phe Arg Asn Glu Arg Ala Ile Arg Phe Val Val
            180                 185                 190

Met Val Thr Pro Glu Asp Leu Lys Ala Asn Ala Glu Tyr Ile Lys Met
        195                 200                 205

Ala Asp His Tyr Val Pro Val Pro Gly Gly Pro Asn Asn Asn Asn Tyr
    210                 215                 220

Ala Asn Val Glu Leu Ile Leu Asp Ile Ala Lys Arg Ile Pro Val Gln
225                 230                 235                 240

Ala Val Trp Ala Gly Trp Gly His Ala Ser Glu Asn Pro Lys Leu Pro
                245                 250                 255

Glu Leu Leu Leu Lys Asn Gly Ile Ala Phe Met Gly Pro Pro Ser Gln
            260                 265                 270

Ala Met Trp Ala Leu Gly Asp Lys Ile Ala Ser Ser Ile Val Ala Gln
        275                 280                 285

Thr Ala Gly Ile Pro Thr Leu Pro Trp Ser Gly Ser Gly Leu Arg Val
    290                 295                 300

Asp Trp Gln Glu Asn Asp Phe Ser Lys Arg Ile Leu Asn Val Pro Gln
305                 310                 315                 320

Glu Leu Tyr Glu Lys Gly Tyr Val Lys Asp Val Asp Asp Gly Leu Gln
                325                 330                 335

Ala Ala Glu Glu Val Gly Tyr Pro Val Met Ile Lys Ala Ser Glu Gly
            340                 345                 350

Gly Gly Gly Lys Gly Ile Arg Lys Val Asn Asn Ala Asp Asp Phe Pro
```

```
                    355                 360                 365
Asn Leu Phe Arg Gln Val Gln Ala Glu Val Pro Gly Ser Pro Ile Phe
    370                 375                 380

Val Met Arg Leu Ala Lys Gln Ser Arg His Leu Glu Val Gln Ile Leu
385                 390                 395                 400

Ala Asp Gln Tyr Gly Asn Ala Ile Ser Leu Phe Gly Arg Asp Cys Ser
            405                 410                 415

Val Gln Arg Arg His Gln Lys Ile Ile Glu Glu Ala Pro Ala Thr Ile
        420                 425                 430

Ala Thr Pro Ala Val Phe Glu His Met Glu Gln Cys Ala Val Lys Leu
    435                 440                 445

Ala Lys Met Val Gly Tyr Val Ser Ala Gly Thr Val Glu Tyr Leu Tyr
    450                 455                 460

Ser Gln Asp Gly Ser Phe Tyr Phe Leu Glu Leu Asn Pro Arg Leu Gln
465                 470                 475                 480

Val Glu His Pro Cys Thr Glu Met Val Ala Asp Val Asn Leu Pro Ala
            485                 490                 495

Ala Gln Leu Gln Ile Ala Met Gly Ile Pro Leu Tyr Arg Ile Lys Asp
        500                 505                 510

Ile Arg Met Met Tyr Gly Val Ser Pro Trp Gly Asp Ser Pro Ile Asp
    515                 520                 525

Phe Glu Asp Ser Ala His Val Pro Cys Pro Arg Gly His Val Ile Ala
    530                 535                 540

Ala Arg Ile Thr Ser Glu Asn Pro Asp Glu Gly Phe Lys Pro Ser Ser
545                 550                 555                 560

Gly Thr Val Gln Glu Leu Asn Phe Arg Ser Asn Lys Asn Val Trp Gly
            565                 570                 575

Tyr Phe Ser Val Ala Ala Ala Gly Gly Leu His Glu Phe Ala Asp Ser
        580                 585                 590

Gln Phe Gly His Cys Phe Ser Trp Gly Glu Asn Arg Glu Glu Ala Ile
    595                 600                 605

Ser Asn Met Val Val Ala Leu Lys Glu Leu Ser Ile Arg Gly Asp Phe
    610                 615                 620

Arg Thr Thr Val Glu Tyr Leu Ile Lys Leu Leu Glu Thr Glu Ser Phe
625                 630                 635                 640

Gln Met Asn Arg Ile Asp Thr Gly Trp Leu Asp Arg Leu Ile Ala Glu
            645                 650                 655

Lys Val Gln Ala Glu Arg Pro Asp Thr Met Leu Gly Val Val Cys Gly
        660                 665                 670

Ala Leu His Val Ala Asp Val Ser Leu Arg Asn Ser Val Ser Asn Phe
    675                 680                 685

Leu His Ser Leu Glu Arg Gly Gln Val Leu Pro Ala His Thr Leu Leu
    690                 695                 700

Asn Thr Val Asp Val Glu Leu Ile Tyr Glu Gly Val Lys Tyr Val Leu
705                 710                 715                 720

Lys Val Thr Arg Gln Ser Pro Asn Ser Tyr Val Val Ile Met Asn Gly
            725                 730                 735

Ser Cys Val Glu Val Asp Val His Arg Leu Ser Asp Gly Gly Leu Leu
        740                 745                 750

Leu Ser Tyr Asp Gly Ser Ser Tyr Thr Thr Tyr Met Lys Glu Glu Val
    755                 760                 765

Asp Arg Tyr Arg Ile Thr Ile Gly Asn Lys Thr Cys Val Phe Glu Lys
    770                 775                 780
```

-continued

```
Glu Asn Asp Pro Ser Val Met Arg Ser Pro Ser Ala Gly Lys Leu Ile
785                 790                 795                 800

Gln Tyr Ile Val Glu Asp Gly His Val Phe Ala Gly Gln Cys Tyr
            805                 810                 815

Ala Glu Ile Glu Val Met Lys Met Val Met Thr Leu Thr Ala Val Glu
        820                 825                 830

Ser Gly Cys Ile His Tyr Val Lys Arg Pro Gly Ala Ala Leu Asp Pro
            835                 840                 845

Gly Cys Val Leu Ala Lys Met Gln Leu Asp Asn Pro Ser Lys Val Gln
850                 855                 860

Gln Ala Glu Leu His Thr Gly Ser Leu Pro Arg Ile Gln Ser Thr Ala
865                 870                 875                 880

Leu Arg Gly Glu Lys Leu His Arg Val Phe His Tyr Val Leu Asp Asn
            885                 890                 895

Leu Val Asn Val Met Asn Gly Tyr Cys Leu Pro Asp Pro Phe Phe Ser
            900                 905                 910

Ser Lys Val Lys Asp Trp Val Glu Arg Leu Met Lys Thr Leu Arg Asp
            915                 920                 925

Pro Ser Leu Pro Leu Leu Glu Leu Gln Asp Ile Met Thr Ser Val Ser
930                 935                 940

Gly Arg Ile Pro Pro Asn Val Glu Lys Ser Ile Lys Lys Glu Met Ala
945                 950                 955                 960

Gln Tyr Ala Ser Asn Ile Thr Ser Val Leu Cys Gln Phe Pro Ser Gln
            965                 970                 975

Gln Ile Ala Asn Ile Leu Asp Ser His Ala Ala Thr Leu Asn Arg Lys
            980                 985                 990

Ser Glu Arg Glu Val Phe Phe Met Asn Thr Gln Ser Ile Val Gln Leu
            995                 1000                1005

Val Gln Arg Tyr Arg Ser Gly Ile Arg Gly His Met Lys Ala Val
    1010                1015                1020

Val Met Asp Leu Leu Arg Gln Tyr Leu Arg Val Glu Thr Gln Phe
    1025                1030                1035

Gln Asn Gly His Tyr Asp Lys Cys Val Phe Ala Leu Arg Glu Glu
    1040                1045                1050

Asn Lys Ser Asp Met Asn Thr Val Leu Asn Tyr Ile Phe Ser His
    1055                1060                1065

Ala Gln Val Thr Lys Lys Asn Leu Leu Val Thr Met Leu Ile Asp
    1070                1075                1080

Gln Leu Cys Gly Arg Asp Pro Thr Leu Thr Asp Glu Leu Leu Asn
    1085                1090                1095

Ile Leu Thr Glu Leu Thr Gln Leu Ser Lys Thr Thr Asn Ala Lys
    1100                1105                1110

Val Ala Leu Arg Ala Arg Gln Val Leu Ile Ala Ser His Leu Pro
    1115                1120                1125

Ser Tyr Glu Leu Arg His Asn Gln Val Glu Ser Ile Phe Leu Ser
    1130                1135                1140

Ala Ile Asp Met Tyr Gly His Gln Phe Cys Ile Glu Asn Leu Gln
    1145                1150                1155

Lys Leu Ile Leu Ser Glu Thr Ser Ile Phe Asp Val Leu Pro Asn
    1160                1165                1170

Phe Phe Tyr His Ser Asn Gln Val Val Arg Met Ala Ala Leu Glu
    1175                1180                1185

Val Tyr Val Arg Arg Ala Tyr Ile Ala Tyr Glu Leu Asn Ser Val
    1190                1195                1200
```

-continued

```
Gln His Arg Gln Leu Lys Asp Asn Thr Cys Val Val Glu Phe Gln
    1205                1210                1215
Phe Met Leu Pro Thr Ser His Pro Asn Arg Gly Asn Ile Pro Thr
    1220                1225                1230
Leu Asn Arg Met Ser Phe Ser Ser Asn Leu Asn His Tyr Gly Met
    1235                1240                1245
Thr His Val Ala Ser Val Ser Asp Val Leu Leu Asp Asn Ser Phe
    1250                1255                1260
Thr Pro Pro Cys Gln Arg Met Gly Gly Met Val Ser Phe Arg Thr
    1265                1270                1275
Phe Glu Asp Phe Val Arg Ile Phe Asp Glu Val Met Gly Cys Phe
    1280                1285                1290
Ser Asp Ser Pro Pro Gln Ser Pro Thr Phe Pro Glu Ala Gly His
    1295                1300                1305
Thr Ser Leu Tyr Asp Glu Asp Lys Val Pro Arg Asp Glu Pro Ile
    1310                1315                1320
His Ile Leu Asn Val Ala Ile Lys Thr Asp Cys Asp Ile Glu Asp
    1325                1330                1335
Asp Arg Leu Ala Ala Met Phe Arg Glu Phe Thr Gln Gln Asn Lys
    1340                1345                1350
Ala Thr Leu Val Asp His Gly Ile Arg Arg Leu Thr Phe Leu Val
    1355                1360                1365
Ala Gln Lys Asp Phe Arg Lys Gln Val Asn Tyr Glu Val Asp Arg
    1370                1375                1380
Arg Phe His Arg Glu Phe Pro Lys Phe Thr Phe Arg Ala Arg
    1385                1390                1395
Asp Lys Phe Glu Glu Asp Arg Ile Tyr Arg His Leu Glu Pro Ala
    1400                1405                1410
Leu Ala Phe Gln Leu Glu Leu Asn Arg Met Arg Asn Phe Asp Leu
    1415                1420                1425
Thr Ala Ile Pro Cys Ala Asn His Lys Met His Leu Tyr Leu Gly
    1430                1435                1440
Ala Ala Lys Val Glu Val Gly Thr Glu Val Thr Asp Tyr Arg Phe
    1445                1450                1455
Phe Val Arg Ala Ile Ile Arg His Ser Asp Leu Val Thr Lys Glu
    1460                1465                1470
Ala Ser Phe Glu Tyr Leu Gln Asn Glu Gly Glu Arg Leu Leu Leu
    1475                1480                1485
Glu Ala Met Asp Glu Leu Glu Val Ala Phe Asn Asn Thr Asn Val
    1490                1495                1500
Arg Thr Asp Cys Asn His Ile Phe Leu Asn Phe Val Pro Thr Val
    1505                1510                1515
Ile Met Asp Pro Ser Lys Ile Glu Glu Ser Val Arg Ser Met Val
    1520                1525                1530
Met Arg Tyr Gly Ser Arg Leu Trp Lys Leu Arg Val Leu Gln Ala
    1535                1540                1545
Glu Leu Lys Ile Asn Ile Arg Leu Thr Pro Thr Gly Lys Ala Ile
    1550                1555                1560
Pro Ile Arg Leu Phe Leu Thr Asn Glu Ser Gly Tyr Tyr Leu Asp
    1565                1570                1575
Ile Ser Leu Tyr Lys Glu Val Thr Asp Ser Arg Thr Ala Gln Ile
    1580                1585                1590
Met Phe Gln Ala Tyr Gly Asp Lys Gln Gly Pro Leu His Gly Met
```

```
                1595                1600                1605

Leu Ile Asn Thr Pro Tyr Val Thr Lys Asp Leu Leu Gln Ser Lys
    1610                1615                1620

Arg Phe Gln Ala Gln Ser Leu Gly Thr Thr Tyr Ile Tyr Asp Ile
    1625                1630                1635

Pro Glu Met Phe Arg Gln Ser Leu Ile Lys Leu Trp Glu Ser Met
    1640                1645                1650

Ser Thr Gln Ala Phe Leu Pro Ser Pro Pro Leu Pro Ser Asp Met
    1655                1660                1665

Leu Thr Tyr Thr Glu Leu Val Leu Asp Asp Gln Gly Gln Leu Val
    1670                1675                1680

His Met Asn Arg Leu Pro Gly Gly Asn Glu Ile Gly Met Val Ala
    1685                1690                1695

Trp Lys Met Thr Phe Lys Ser Pro Glu Tyr Pro Glu Gly Arg Asp
    1700                1705                1710

Ile Ile Val Ile Gly Asn Asp Ile Thr Tyr Arg Ile Gly Ser Phe
    1715                1720                1725

Gly Pro Gln Glu Asp Leu Leu Phe Leu Arg Ala Ser Glu Leu Ala
    1730                1735                1740

Arg Ala Glu Gly Ile Pro Arg Ile Tyr Val Ser Ala Asn Ser Gly
    1745                1750                1755

Ala Arg Ile Gly Leu Ala Glu Glu Ile Arg His Met Phe His Val
    1760                1765                1770

Ala Trp Val Asp Pro Glu Asp Pro Tyr Lys Gly Tyr Arg Tyr Leu
    1775                1780                1785

Tyr Leu Thr Pro Gln Asp Tyr Lys Arg Val Ser Ala Leu Asn Ser
    1790                1795                1800

Val His Cys Glu His Val Glu Asp Glu Gly Glu Ser Arg Tyr Lys
    1805                1810                1815

Ile Thr Asp Ile Ile Gly Lys Glu Glu Gly Ile Gly Pro Glu Asn
    1820                1825                1830

Leu Arg Gly Ser Gly Met Ile Ala Gly Glu Ser Ser Leu Ala Tyr
    1835                1840                1845

Asn Glu Ile Ile Thr Ile Ser Leu Val Thr Cys Arg Ala Ile Gly
    1850                1855                1860

Ile Gly Ala Tyr Leu Val Arg Leu Gly Gln Arg Thr Ile Gln Val
    1865                1870                1875

Glu Asn Ser His Leu Ile Leu Thr Gly Ala Gly Ala Leu Asn Lys
    1880                1885                1890

Val Leu Gly Arg Glu Val Tyr Thr Ser Asn Asn Gln Leu Gly Gly
    1895                1900                1905

Ile Gln Ile Met His Asn Asn Gly Val Thr His Cys Thr Val Cys
    1910                1915                1920

Asp Asp Phe Glu Gly Val Phe Thr Val Leu His Trp Leu Ser Tyr
    1925                1930                1935

Met Pro Lys Ser Val His Ser Ser Val Pro Leu Leu Asn Ser Lys
    1940                1945                1950

Asp Pro Ile Asp Arg Ile Ile Glu Phe Val Pro Thr Lys Thr Pro
    1955                1960                1965

Tyr Asp Pro Arg Trp Met Leu Ala Gly Arg Pro His Pro Thr Gln
    1970                1975                1980

Lys Gly Gln Trp Leu Ser Gly Phe Phe Asp Tyr Gly Ser Phe Ser
    1985                1990                1995
```

```
Glu Ile Met Gln Pro Trp Ala Gln Thr Val Val Gly Arg Ala
         2000                2005                2010

Arg Leu Gly Gly Ile Pro Val Gly Val Ala Val Glu Thr Arg
         2015                2020                2025

Thr Val Glu Leu Ser Ile Pro Ala Asp Pro Ala Asn Leu Asp Ser
         2030                2035                2040

Glu Ala Lys Ile Ile Gln Gln Ala Gly Gln Val Trp Phe Pro Asp
         2045                2050                2055

Ser Ala Phe Lys Thr Tyr Gln Ala Ile Lys Asp Phe Asn Arg Glu
         2060                2065                2070

Gly Leu Pro Leu Met Val Phe Ala Asn Trp Arg Gly Phe Ser Gly
         2075                2080                2085

Gly Met Lys Asp Met Tyr Asp Gln Val Leu Lys Phe Gly Ala Tyr
         2090                2095                2100

Ile Val Asp Gly Leu Arg Glu Cys Cys Gln Pro Val Leu Val Tyr
         2105                2110                2115

Ile Pro Pro Gln Ala Glu Leu Arg Gly Gly Ser Trp Val Val Ile
         2120                2125                2130

Asp Ser Ser Ile Asn Pro Arg His Met Glu Met Tyr Ala Asp Arg
         2135                2140                2145

Glu Ser Arg Gly Ser Val Leu Glu Pro Glu Gly Thr Val Glu Ile
         2150                2155                2160

Lys Phe Arg Arg Lys Asp Leu Val Lys Thr Met Arg Arg Val Asp
         2165                2170                2175

Pro Val Tyr Ile His Leu Ala Glu Arg Leu Gly Thr Pro Glu Leu
         2180                2185                2190

Ser Thr Ala Glu Arg Lys Glu Leu Glu Asn Lys Leu Lys Glu Arg
         2195                2200                2205

Glu Glu Phe Leu Ile Pro Ile Tyr His Gln Val Ala Val Gln Phe
         2210                2215                2220

Ala Asp Leu His Asp Thr Pro Gly Arg Met Gln Glu Lys Gly Val
         2225                2230                2235

Ile Ser Asp Ile Leu Asp Trp Lys Thr Ser Arg Thr Phe Phe Tyr
         2240                2245                2250

Trp Arg Leu Arg Arg Leu Leu Leu Glu Asp Leu Val Lys Lys Lys
         2255                2260                2265

Ile His Asn Ala Asn Pro Glu Leu Thr Asp Gly Gln Ile Gln Ala
         2270                2275                2280

Met Leu Arg Arg Trp Phe Val Glu Val Glu Gly Thr Val Lys Ala
         2285                2290                2295

Tyr Val Trp Asp Asn Asn Lys Asp Leu Ala Glu Trp Leu Glu Lys
         2300                2305                2310

Gln Leu Thr Glu Glu Asp Gly Val His Ser Val Ile Glu Glu Asn
         2315                2320                2325

Ile Lys Cys Ile Ser Arg Asp Tyr Val Leu Lys Gln Ile Arg Ser
         2330                2335                2340

Leu Val Gln Ala Asn Pro Glu Val Ala Met Asp Ser Ile Ile His
         2345                2350                2355

Met Thr Gln His Ile Ser Pro Thr Gln Arg Ala Glu Val Ile Arg
         2360                2365                2370

Ile Leu Ser Thr Met Asp Ser Pro Ser Thr
         2375                2380

<210> SEQ ID NO 18
```

<211> LENGTH: 2458
<212> TYPE: PRT
<213> ORGANISM: Homo sapiens

<400> SEQUENCE: 18

```
Met Val Leu Leu Leu Cys Leu Ser Cys Leu Ile Phe Ser Cys Leu Thr
1               5                   10                  15

Phe Ser Trp Leu Lys Ile Trp Gly Lys Met Thr Asp Ser Lys Pro Ile
            20                  25                  30

Thr Lys Ser Lys Ser Glu Ala Asn Leu Ile Pro Ser Gln Glu Pro Phe
        35                  40                  45

Pro Ala Ser Asp Asn Ser Gly Glu Thr Pro Gln Arg Asn Gly Glu Gly
    50                  55                  60

His Thr Leu Pro Lys Thr Pro Ser Gln Ala Glu Pro Ala Ser His Lys
65                  70                  75                  80

Gly Pro Lys Asp Ala Gly Arg Arg Asn Ser Leu Pro Pro Ser His
                85                  90                  95

Gln Lys Pro Pro Arg Asn Pro Leu Ser Ser Asp Ala Ala Pro Ser
                100                 105                 110

Pro Glu Leu Gln Ala Asn Gly Thr Gly Thr Gln Gly Leu Glu Ala Thr
                115                 120                 125

Asp Thr Asn Gly Leu Ser Ser Ser Ala Arg Pro Gln Gly Gln Gln Ala
    130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Asp Tyr Ser Ser Asp
                165                 170                 175

Glu Asp Ser Val Ala Gly Ser Ser Arg Glu Ser Thr Arg Lys Gly Ser
                180                 185                 190

Arg Ala Ser Leu Gly Ala Leu Ser Leu Glu Ala Tyr Leu Thr Thr Gly
                195                 200                 205

Glu Ala Glu Thr Arg Val Pro Thr Met Arg Pro Ser Met Ser Gly Leu
    210                 215                 220

His Leu Val Lys Arg Gly Arg Glu His Lys Lys Leu Asp Leu His Arg
225                 230                 235                 240

Asp Phe Thr Val Ala Ser Pro Ala Glu Phe Val Thr Arg Phe Gly Gly
                245                 250                 255

Asp Arg Val Ile Glu Lys Val Leu Ile Ala Asn Asn Gly Ile Ala Ala
                260                 265                 270

Val Lys Cys Met Arg Ser Ile Arg Arg Trp Ala Tyr Glu Met Phe Arg
                275                 280                 285

Asn Glu Arg Ala Ile Arg Phe Val Val Met Val Thr Pro Glu Asp Leu
    290                 295                 300

Lys Ala Asn Ala Glu Tyr Ile Lys Met Ala Asp His Tyr Val Pro Val
305                 310                 315                 320

Pro Gly Gly Pro Asn Asn Asn Tyr Ala Asn Val Glu Leu Ile Val
                325                 330                 335

Asp Ile Ala Lys Arg Ile Pro Val Gln Ala Val Trp Ala Gly Trp Gly
                340                 345                 350

His Ala Ser Glu Asn Pro Lys Leu Pro Glu Leu Leu Cys Lys Asn Gly
                355                 360                 365

Val Ala Phe Leu Gly Pro Pro Ser Glu Ala Met Trp Ala Leu Gly Asp
    370                 375                 380

Lys Ile Ala Ser Thr Val Val Ala Gln Thr Leu Gln Val Pro Thr Leu
385                 390                 395                 400
```

```
Pro Trp Ser Gly Ser Gly Leu Thr Val Glu Trp Thr Glu Asp Asp Leu
                405                 410                 415
Gln Gln Gly Lys Arg Ile Ser Val Pro Glu Asp Val Tyr Asp Lys Gly
            420                 425                 430
Cys Val Lys Asp Val Asp Glu Gly Leu Glu Ala Ala Glu Arg Ile Gly
            435                 440                 445
Phe Pro Leu Met Ile Lys Ala Ser Gly Gly Gly Gly Lys Gly Ile
450                 455                 460
Arg Lys Ala Glu Ser Ala Glu Asp Phe Pro Ile Leu Phe Arg Gln Val
465                 470                 475                 480
Gln Ser Glu Ile Pro Gly Ser Pro Ile Phe Leu Met Lys Leu Ala Gln
                485                 490                 495
His Ala Arg His Leu Glu Val Gln Ile Leu Ala Asp Gln Tyr Gly Asn
                500                 505                 510
Ala Val Ser Leu Phe Gly Arg Asp Cys Ser Ile Gln Arg Arg His Gln
            515                 520                 525
Lys Ile Val Glu Glu Ala Pro Ala Thr Ile Ala Pro Leu Ala Ile Phe
            530                 535                 540
Glu Phe Met Glu Gln Cys Ala Ile Arg Leu Ala Lys Thr Val Gly Tyr
545                 550                 555                 560
Val Ser Ala Gly Thr Val Glu Tyr Leu Tyr Ser Gln Asp Gly Ser Phe
                565                 570                 575
His Phe Leu Glu Leu Asn Pro Arg Leu Gln Val Glu His Pro Cys Thr
            580                 585                 590
Glu Met Ile Ala Asp Val Asn Leu Pro Ala Ala Gln Leu Gln Ile Ala
            595                 600                 605
Met Gly Val Pro Leu His Arg Leu Lys Asp Ile Arg Leu Leu Tyr Gly
610                 615                 620
Glu Ser Pro Trp Gly Val Thr Pro Ile Ser Phe Glu Thr Pro Ser Asn
625                 630                 635                 640
Pro Pro Leu Ala Arg Gly His Val Ile Ala Ala Arg Ile Thr Ser Glu
                645                 650                 655
Asn Pro Asp Glu Gly Phe Lys Pro Ser Ser Gly Thr Val Gln Glu Leu
            660                 665                 670
Asn Phe Arg Ser Ser Lys Asn Val Trp Gly Tyr Phe Ser Val Ala Ala
            675                 680                 685
Thr Gly Gly Leu His Glu Phe Ala Asp Ser Gln Phe Gly His Cys Phe
            690                 695                 700
Ser Trp Gly Glu Asn Arg Glu Glu Ala Ile Ser Asn Met Val Val Ala
705                 710                 715                 720
Leu Lys Glu Leu Ser Ile Arg Gly Asp Phe Arg Thr Thr Val Glu Tyr
                725                 730                 735
Leu Ile Asn Leu Leu Glu Thr Glu Ser Phe Gln Asn Asn Asp Ile Asp
                740                 745                 750
Thr Gly Trp Leu Asp Tyr Leu Ile Ala Glu Lys Val Gln Ala Glu Lys
            755                 760                 765
Pro Asp Ile Met Leu Gly Val Val Cys Gly Ala Leu Asn Val Ala Asp
            770                 775                 780
Ala Met Phe Arg Thr Cys Met Thr Asp Phe Leu His Ser Leu Glu Arg
785                 790                 795                 800
Gly Gln Val Leu Pro Ala Asp Ser Leu Leu Asn Leu Val Asp Val Glu
                805                 810                 815
Leu Ile Tyr Gly Gly Val Lys Tyr Ile Leu Lys Val Ala Arg Gln Ser
```

```
                820                 825                 830
Leu Thr Met Phe Val Leu Ile Met Asn Gly Cys His Ile Glu Ile Asp
        835                 840                 845
Ala His Arg Leu Asn Asp Gly Gly Leu Leu Ser Tyr Asn Gly Asn
        850                 855                 860
Ser Tyr Thr Thr Tyr Met Lys Glu Val Asp Ser Tyr Arg Ile Thr
865                 870                 875                 880
Ile Gly Asn Lys Thr Cys Val Phe Glu Lys Asn Asp Pro Thr Val
                885                 890                 895
Leu Arg Ser Pro Ser Ala Gly Lys Leu Thr Gln Tyr Thr Val Glu Asp
                900                 905                 910
Gly Gly His Val Glu Ala Gly Ser Ser Tyr Ala Glu Met Glu Val Met
                915                 920                 925
Lys Met Ile Met Thr Leu Asn Val Gln Glu Arg Gly Arg Val Lys Tyr
        930                 935                 940
Ile Lys Arg Pro Gly Ala Val Leu Glu Ala Gly Cys Val Val Ala Arg
945                 950                 955                 960
Leu Glu Leu Asp Asp Pro Ser Lys Val His Pro Ala Glu Pro Phe Thr
                965                 970                 975
Gly Glu Leu Pro Ala Gln Gln Thr Leu Pro Ile Leu Gly Glu Lys Leu
                980                 985                 990
His Gln Val Phe His Ser Val Leu Glu Asn Leu Thr Asn Val Met Ser
                995                 1000                1005
Gly Phe Cys Leu Pro Glu Pro Val Phe Ser Ile Lys Leu Lys Glu
        1010                1015                1020
Trp Val Gln Lys Leu Met Met Thr Leu Arg His Pro Ser Leu Pro
        1025                1030                1035
Leu Leu Glu Leu Gln Glu Ile Met Thr Ser Val Ala Gly Arg Ile
        1040                1045                1050
Pro Ala Pro Val Glu Lys Ser Val Arg Arg Val Met Ala Gln Tyr
        1055                1060                1065
Ala Ser Asn Ile Thr Ser Val Leu Cys Gln Phe Pro Ser Gln Gln
        1070                1075                1080
Ile Ala Thr Ile Leu Asp Cys His Ala Ala Thr Leu Gln Arg Lys
        1085                1090                1095
Ala Asp Arg Glu Val Phe Phe Ile Asn Thr Gln Ser Ile Val Gln
        1100                1105                1110
Leu Val Gln Arg Tyr Arg Ser Gly Ile Arg Gly Tyr Met Lys Thr
        1115                1120                1125
Val Val Leu Asp Leu Leu Arg Arg Tyr Leu Arg Val Glu His His
        1130                1135                1140
Phe Gln Gln Ala His Tyr Asp Lys Cys Val Ile Asn Leu Arg Glu
        1145                1150                1155
Gln Phe Lys Pro Asp Met Ser Gln Val Leu Asp Cys Ile Phe Ser
        1160                1165                1170
His Ala Gln Val Ala Lys Lys Asn Gln Leu Val Ile Met Leu Ile
        1175                1180                1185
Asp Glu Leu Cys Gly Pro Asp Pro Ser Leu Ser Asp Glu Leu Ile
        1190                1195                1200
Ser Ile Leu Asn Glu Leu Thr Gln Leu Ser Lys Ser Glu His Cys
        1205                1210                1215
Lys Val Ala Leu Arg Ala Arg Gln Ile Leu Ile Ala Ser His Leu
        1220                1225                1230
```

```
Pro Ser Tyr Glu Leu Arg His Asn Gln Val Glu Ser Ile Phe Leu
1235                1240                1245

Ser Ala Ile Asp Met Tyr Gly His Gln Phe Cys Pro Glu Asn Leu
1250                1255                1260

Lys Lys Leu Ile Leu Ser Glu Thr Thr Ile Phe Asp Val Leu Pro
1265                1270                1275

Thr Phe Phe Tyr His Ala Asn Lys Val Val Cys Met Ala Ser Leu
1280                1285                1290

Glu Val Tyr Val Arg Arg Gly Tyr Ile Ala Tyr Glu Leu Asn Ser
1295                1300                1305

Leu Gln His Arg Gln Leu Pro Asp Gly Thr Cys Val Val Glu Phe
1310                1315                1320

Gln Phe Met Leu Pro Ser Ser His Pro Asn Arg Met Thr Val Pro
1325                1330                1335

Ile Ser Ile Thr Asn Pro Asp Leu Leu Arg His Ser Thr Glu Leu
1340                1345                1350

Phe Met Asp Ser Gly Phe Ser Pro Leu Cys Gln Arg Met Gly Ala
1355                1360                1365

Met Val Ala Phe Arg Arg Phe Glu Asp Phe Thr Arg Asn Phe Asp
1370                1375                1380

Glu Val Ile Ser Cys Phe Ala Asn Val Pro Lys Asp Thr Pro Leu
1385                1390                1395

Phe Ser Glu Ala Arg Thr Ser Leu Tyr Ser Glu Asp Asp Cys Lys
1400                1405                1410

Ser Leu Arg Glu Glu Pro Ile His Ile Leu Asn Val Ser Ile Gln
1415                1420                1425

Cys Ala Asp His Leu Glu Asp Glu Ala Leu Val Pro Ile Leu Arg
1430                1435                1440

Thr Phe Val Gln Ser Lys Lys Asn Ile Leu Val Asp Tyr Gly Leu
1445                1450                1455

Arg Arg Ile Thr Phe Leu Ile Ala Gln Glu Lys Glu Phe Pro Lys
1460                1465                1470

Phe Phe Thr Phe Arg Ala Arg Asp Glu Phe Ala Glu Asp Arg Ile
1475                1480                1485

Tyr Arg His Leu Glu Pro Ala Leu Ala Phe Gln Leu Glu Leu Asn
1490                1495                1500

Arg Met Arg Asn Phe Asp Leu Thr Ala Val Pro Cys Ala Asn His
1505                1510                1515

Lys Met His Leu Tyr Leu Gly Ala Ala Lys Val Lys Glu Gly Val
1520                1525                1530

Glu Val Thr Asp His Arg Phe Phe Ile Arg Ala Ile Ile Arg His
1535                1540                1545

Ser Asp Leu Ile Thr Lys Glu Ala Ser Phe Glu Tyr Leu Gln Asn
1550                1555                1560

Glu Gly Glu Arg Leu Leu Leu Glu Ala Met Asp Glu Leu Glu Val
1565                1570                1575

Ala Phe Asn Asn Thr Ser Val Arg Thr Asp Cys Asn His Ile Phe
1580                1585                1590

Leu Asn Phe Val Pro Thr Val Ile Met Asp Pro Phe Lys Ile Glu
1595                1600                1605

Glu Ser Val Arg Tyr Met Val Met Arg Tyr Gly Ser Arg Leu Trp
1610                1615                1620

Lys Leu Arg Val Leu Gln Ala Glu Val Lys Ile Asn Ile Arg Gln
1625                1630                1635
```

-continued

Thr Thr Thr Gly Ser Ala Val Pro Ile Arg Leu Phe Ile Thr Asn
    1640             1645             1650

Glu Ser Gly Tyr Tyr Leu Asp Ile Ser Leu Tyr Lys Glu Val Thr
    1655             1660             1665

Asp Ser Arg Ser Gly Asn Ile Met Phe His Ser Phe Gly Asn Lys
    1670             1675             1680

Gln Gly Pro Gln His Gly Met Leu Ile Asn Thr Pro Tyr Val Thr
    1685             1690             1695

Lys Asp Leu Leu Gln Ala Lys Arg Phe Gln Ala Gln Thr Leu Gly
    1700             1705             1710

Thr Thr Tyr Ile Tyr Asp Phe Pro Glu Met Phe Arg Gln Ala Leu
    1715             1720             1725

Phe Lys Leu Trp Gly Ser Pro Asp Lys Tyr Pro Lys Asp Ile Leu
    1730             1735             1740

Thr Tyr Thr Glu Leu Val Leu Asp Ser Gln Gly Gln Leu Val Glu
    1745             1750             1755

Met Asn Arg Leu Pro Gly Gly Asn Glu Val Gly Met Val Ala Phe
    1760             1765             1770

Lys Met Arg Phe Lys Thr Gln Glu Tyr Pro Glu Gly Arg Asp Val
    1775             1780             1785

Ile Val Ile Gly Asn Asp Ile Thr Phe Arg Ile Gly Ser Phe Gly
    1790             1795             1800

Pro Gly Glu Asp Leu Leu Tyr Leu Arg Ala Ser Glu Met Ala Arg
    1805             1810             1815

Ala Glu Gly Ile Pro Lys Ile Tyr Val Ala Ala Asn Ser Gly Ala
    1820             1825             1830

Arg Ile Gly Met Ala Glu Glu Ile Lys His Met Phe His Val Ala
    1835             1840             1845

Trp Val Asp Pro Glu Asp Pro His Lys Gly Phe Lys Tyr Leu Tyr
    1850             1855             1860

Leu Thr Pro Gln Asp Tyr Thr Arg Ile Ser Ser Leu Asn Ser Val
    1865             1870             1875

His Cys Lys His Ile Glu Glu Gly Gly Glu Ser Arg Tyr Met Ile
    1880             1885             1890

Thr Asp Ile Ile Gly Lys Asp Asp Gly Leu Gly Val Glu Asn Leu
    1895             1900             1905

Arg Gly Ser Gly Met Ile Ala Gly Glu Ser Ser Leu Ala Tyr Glu
    1910             1915             1920

Glu Ile Val Thr Ile Ser Leu Val Thr Cys Arg Ala Ile Gly Ile
    1925             1930             1935

Gly Ala Tyr Leu Val Arg Leu Gly Gln Arg Val Ile Gln Val Glu
    1940             1945             1950

Asn Ser His Ile Ile Leu Thr Gly Ala Ser Ala Leu Asn Lys Val
    1955             1960             1965

Leu Gly Arg Glu Val Tyr Thr Ser Asn Asn Gln Leu Gly Gly Val
    1970             1975             1980

Gln Ile Met His Tyr Asn Gly Val Ser His Ile Thr Val Pro Asp
    1985             1990             1995

Asp Phe Glu Gly Val Tyr Thr Ile Leu Glu Trp Leu Ser Tyr Met
    2000             2005             2010

Pro Lys Asp Asn His Ser Pro Val Pro Ile Ile Thr Pro Thr Asp
    2015             2020             2025

Pro Ile Asp Arg Glu Ile Glu Phe Leu Pro Ser Arg Ala Pro Tyr

-continued

```
              2030                2035                2040

Asp Pro Arg Trp Met Leu Ala Gly Arg Pro His Pro Thr Leu Lys
    2045                2050                2055

Gly Thr Trp Gln Ser Gly Phe Phe Asp His Gly Ser Phe Lys Glu
    2060                2065                2070

Ile Met Ala Pro Trp Ala Gln Thr Val Val Thr Gly Arg Ala Arg
    2075                2080                2085

Leu Gly Gly Ile Pro Val Gly Val Ile Ala Val Glu Thr Arg Thr
    2090                2095                2100

Val Glu Val Ala Val Pro Ala Asp Pro Ala Asn Leu Asp Ser Glu
    2105                2110                2115

Ala Lys Ile Ile Gln Gln Ala Gly Gln Val Trp Phe Pro Asp Ser
    2120                2125                2130

Ala Tyr Lys Thr Ala Gln Ala Ile Lys Asp Phe Asn Arg Glu Lys
    2135                2140                2145

Leu Pro Leu Met Ile Phe Ala Asn Trp Arg Gly Phe Ser Gly Gly
    2150                2155                2160

Met Lys Asp Met Tyr Asp Gln Val Leu Lys Phe Gly Ala Tyr Ile
    2165                2170                2175

Val Asp Gly Leu Arg Gln Tyr Lys Gln Pro Ile Leu Ile Tyr Ile
    2180                2185                2190

Pro Pro Tyr Ala Glu Leu Arg Gly Gly Ser Trp Val Val Ile Asp
    2195                2200                2205

Ala Thr Ile Asn Pro Leu Cys Ile Glu Met Tyr Ala Asp Lys Glu
    2210                2215                2220

Ser Arg Gly Gly Val Leu Glu Pro Glu Gly Thr Val Glu Ile Lys
    2225                2230                2235

Phe Arg Lys Lys Asp Leu Ile Lys Ser Met Arg Arg Ile Asp Pro
    2240                2245                2250

Ala Tyr Lys Lys Leu Met Glu Gln Leu Gly Glu Pro Asp Leu Ser
    2255                2260                2265

Asp Lys Asp Arg Lys Asp Leu Glu Gly Arg Leu Lys Ala Arg Glu
    2270                2275                2280

Asp Leu Leu Leu Pro Ile Tyr His Gln Val Ala Val Gln Phe Ala
    2285                2290                2295

Asp Phe His Asp Thr Pro Gly Arg Met Leu Glu Lys Gly Val Ile
    2300                2305                2310

Ser Asp Ile Leu Glu Trp Lys Thr Ala Arg Thr Phe Leu Tyr Trp
    2315                2320                2325

Arg Leu Arg Arg Leu Leu Leu Glu Asp Gln Val Lys Gln Glu Ile
    2330                2335                2340

Leu Gln Ala Ser Gly Glu Leu Ser His Val His Ile Gln Ser Met
    2345                2350                2355

Leu Arg Arg Trp Phe Val Glu Thr Glu Gly Ala Val Lys Ala Tyr
    2360                2365                2370

Leu Trp Asp Asn Asn Gln Val Val Val Gln Trp Leu Glu Gln His
    2375                2380                2385

Trp Gln Ala Gly Asp Gly Pro Arg Ser Thr Ile Arg Glu Asn Ile
    2390                2395                2400

Thr Tyr Leu Lys His Asp Ser Val Leu Lys Thr Ile Arg Gly Leu
    2405                2410                2415

Val Glu Glu Asn Pro Glu Val Ala Val Asp Cys Val Ile Tyr Leu
    2420                2425                2430
```

Ser Gln His Ile Ser Pro Ala Glu Arg Ala Gln Val Val His Leu
    2435                2440                2445

Leu Ser Thr Met Asp Ser Pro Ala Ser Thr
    2450                2455

<210> SEQ ID NO 19
<211> LENGTH: 731
<212> TYPE: PRT
<213> ORGANISM: Homo sapiens

<400> SEQUENCE: 19

Met Ser Gly Ser Arg Gln Ala Gly Ser Gly Ala Gly Thr Ser Pro
1               5                   10                  15

Gly Ser Ser Ala Ala Ser Ser Val Thr Ser Ala Ser Ser Leu Ser
                20                  25                  30

Ser Ser Pro Ser Pro Ser Val Ala Val Ser Ala Ala Ala Leu Val
            35                  40                  45

Ser Gly Gly Val Ala Gln Ala Ala Gly Ser Gly Gly Leu Gly Gly Pro
        50                  55                  60

Val Arg Pro Val Leu Val Ala Pro Ala Val Ser Gly Ser Gly Gly
65              70                  75                  80

Ala Val Ser Thr Gly Leu Ser Arg His Ser Cys Ala Ala Arg Pro Ser
                85                  90                  95

Ala Gly Val Gly Gly Ser Ser Ser Leu Gly Ser Gly Ser Arg Lys
                100                 105                 110

Arg Pro Leu Leu Ala Pro Leu Cys Asn Gly Leu Ile Asn Ser Tyr Glu
            115                 120                 125

Asp Lys Ser Asn Asp Phe Val Cys Pro Ile Cys Phe Asp Met Ile Glu
    130                 135                 140

Glu Ala Tyr Met Thr Lys Cys Gly His Ser Phe Cys Tyr Lys Cys Ile
145                 150                 155                 160

His Gln Ser Leu Glu Asp Asn Asn Arg Cys Pro Lys Cys Asn Tyr Val
                165                 170                 175

Val Asp Asn Ile Asp His Leu Tyr Pro Asn Phe Leu Val Asn Glu Leu
            180                 185                 190

Ile Leu Lys Gln Lys Gln Arg Phe Glu Glu Lys Arg Phe Lys Leu Asp
        195                 200                 205

His Ser Val Ser Ser Thr Asn Gly His Arg Trp Gln Ile Phe Gln Asp
    210                 215                 220

Trp Leu Gly Thr Asp Gln Asp Asn Leu Asp Leu Ala Asn Val Asn Leu
225                 230                 235                 240

Met Leu Glu Leu Leu Val Gln Lys Lys Lys Gln Leu Glu Ala Glu Ser
                245                 250                 255

His Ala Ala Gln Leu Gln Ile Leu Met Glu Phe Leu Lys Val Ala Arg
            260                 265                 270

Arg Asn Lys Arg Glu Gln Leu Glu Gln Ile Gln Lys Glu Leu Ser Val
        275                 280                 285

Leu Glu Glu Asp Ile Lys Arg Val Glu Met Ser Gly Leu Tyr Ser
    290                 295                 300

Pro Val Ser Glu Asp Ser Thr Val Pro Gln Phe Glu Ala Pro Ser Pro
305                 310                 315                 320

Ser His Ser Ser Ile Ile Asp Ser Thr Glu Tyr Ser Gln Pro Pro Gly
                325                 330                 335

Phe Ser Gly Ser Ser Gln Thr Lys Lys Gln Pro Trp Tyr Asn Ser Thr
            340                 345                 350

```
Leu Ala Ser Arg Arg Lys Arg Leu Thr Ala His Phe Glu Asp Leu Glu
        355                 360                 365

Gln Cys Tyr Phe Ser Thr Arg Met Ser Arg Ile Ser Asp Asp Ser Arg
    370                 375                 380

Thr Ala Ser Gln Leu Asp Glu Phe Gln Glu Cys Leu Ser Lys Phe Thr
385                 390                 395                 400

Arg Tyr Asn Ser Val Arg Pro Leu Ala Thr Leu Ser Tyr Ala Ser Asp
                405                 410                 415

Leu Tyr Asn Gly Ser Ser Ile Val Ser Ser Ile Glu Phe Asp Arg Asp
            420                 425                 430

Cys Asp Tyr Phe Ala Ile Ala Gly Val Thr Lys Lys Ile Lys Val Tyr
        435                 440                 445

Glu Tyr Asp Thr Val Ile Gln Asp Ala Val Asp Ile His Tyr Pro Glu
    450                 455                 460

Asn Glu Met Thr Cys Asn Ser Lys Ile Ser Cys Ile Ser Trp Ser Ser
465                 470                 475                 480

Tyr His Lys Asn Leu Leu Ala Ser Ser Asp Tyr Glu Gly Thr Val Ile
                485                 490                 495

Leu Trp Asp Gly Phe Thr Gly Gln Arg Ser Lys Val Tyr Gln Glu His
            500                 505                 510

Glu Lys Arg Cys Trp Ser Val Asp Phe Asn Leu Met Asp Pro Lys Leu
        515                 520                 525

Leu Ala Ser Gly Ser Asp Asp Ala Lys Val Lys Leu Trp Ser Thr Asn
    530                 535                 540

Leu Asp Asn Ser Val Ala Ser Ile Glu Ala Lys Ala Asn Val Cys Cys
545                 550                 555                 560

Val Lys Phe Ser Pro Ser Ser Arg Tyr His Leu Ala Phe Gly Cys Ala
                565                 570                 575

Asp His Cys Val His Tyr Tyr Asp Leu Arg Asn Thr Lys Gln Pro Ile
            580                 585                 590

Met Val Phe Lys Gly His Arg Lys Ala Val Ser Tyr Ala Lys Phe Val
        595                 600                 605

Ser Gly Glu Glu Ile Val Ser Ala Ser Thr Asp Ser Gln Leu Lys Leu
    610                 615                 620

Trp Asn Val Gly Lys Pro Tyr Cys Leu Arg Ser Phe Lys Gly His Ile
625                 630                 635                 640

Asn Glu Lys Asn Phe Val Gly Leu Ala Ser Asn Gly Asp Tyr Ile Ala
                645                 650                 655

Cys Gly Ser Glu Asn Asn Ser Leu Tyr Leu Tyr Lys Gly Leu Ser
            660                 665                 670

Lys Thr Leu Leu Thr Phe Lys Phe Asp Thr Val Lys Ser Val Leu Asp
        675                 680                 685

Lys Asp Arg Lys Glu Asp Asp Thr Asn Glu Phe Val Ser Ala Val Cys
    690                 695                 700

Trp Arg Ala Leu Pro Asp Gly Glu Ser Asn Val Leu Ile Ala Ala Asn
705                 710                 715                 720

Ser Gln Gly Thr Ile Lys Val Leu Glu Leu Val
                725                 730

<210> SEQ ID NO 20
<211> LENGTH: 733
<212> TYPE: PRT
<213> ORGANISM: Mus musculus

<400> SEQUENCE: 20
```

```
Met Ser Gly Ser Arg Gln Ala Gly Ser Ala Gly Thr Ser Pro
1               5                   10                  15

Gly Ser Ser Ala Ala Ser Ser Val Thr Ser Ala Ser Ser Ser Leu Ser
            20              25              30

Ser Ser Pro Ser Pro Pro Ser Val Ala Ala Ser Ala Ala Thr Leu Val
        35          40                  45

Ser Gly Gly Val Ala Pro Ala Ala Gly Ser Gly Gly Leu Gly Gly Pro
50                  55                  60

Gly Arg Pro Val Leu Val Ala Ala Ala Val Ser Gly Ser Ala Ser Ala
65              70                  75                  80

Gly Gly Ala Val Ser Ala Gly Gln Ser Arg Leu Ser Cys Ala Ala Arg
                85                  90                  95

Pro Ser Ala Gly Val Gly Gly Ser Ser Ser Leu Gly Ser Ser Ser
            100                 105                 110

Arg Lys Arg Pro Leu Leu Val Pro Leu Cys Asn Gly Leu Leu Asn Ser
            115                 120                 125

Tyr Glu Asp Lys Ser Asn Asp Phe Val Cys Pro Ile Cys Phe Asp Met
        130                 135                 140

Ile Glu Glu Ala Tyr Met Thr Lys Cys Gly His Ser Phe Cys Tyr Lys
145                 150                 155                 160

Cys Ile His Gln Ser Leu Glu Asp Asn Arg Cys Pro Lys Cys Asn
                165                 170                 175

Tyr Val Val Asp Asn Ile Asp His Leu Tyr Pro Asn Phe Leu Val Asn
                180                 185                 190

Glu Leu Ile Leu Lys Gln Lys Gln Arg Phe Glu Lys Arg Phe Lys
            195                 200                 205

Leu Asp His Ser Val Ser Ser Thr Asn Gly His Arg Trp Gln Ile Phe
210                 215                 220

Gln Asp Leu Leu Gly Thr Asp Gln Asp Asn Leu Asp Leu Ala Asn Val
225                 230                 235                 240

Asn Leu Met Leu Glu Leu Leu Val Gln Lys Lys Gln Leu Glu Ala
                245                 250                 255

Glu Ser His Ala Ala Gln Leu Gln Ile Leu Met Glu Phe Leu Lys Val
            260                 265                 270

Ala Arg Arg Asn Lys Arg Glu Gln Leu Glu Gln Ile Gln Lys Glu Leu
            275                 280                 285

Ser Val Leu Glu Glu Asp Ile Lys Arg Val Glu Glu Met Ser Gly Leu
            290                 295                 300

Tyr Ser Pro Val Ser Glu Asp Ser Thr Val Pro Gln Phe Glu Ala Pro
305                 310                 315                 320

Ser Pro Ser His Ser Ser Ile Ile Asp Ser Thr Glu Tyr Ser Gln Pro
                325                 330                 335

Pro Gly Phe Ser Gly Thr Ser Gln Thr Lys Lys Gln Pro Trp Tyr Asn
            340                 345                 350

Ser Thr Leu Ala Ser Arg Arg Lys Arg Leu Thr Ala His Phe Glu Asp
        355                 360                 365

Leu Glu Gln Cys Tyr Phe Ser Thr Arg Met Ser Arg Ile Ser Asp Asp
        370                 375                 380

Ser Arg Thr Ala Ser Gln Leu Asp Glu Phe Gln Glu Cys Leu Ser Lys
385                 390                 395                 400

Phe Thr Arg Tyr Asn Ser Val Arg Pro Leu Ala Thr Leu Ser Tyr Ala
            405                 410                 415

Ser Asp Leu Tyr Asn Gly Ser Ser Ile Val Ser Ser Ile Glu Phe Asp
            420                 425                 430
```

-continued

```
Arg Asp Cys Asp Tyr Phe Ala Ile Ala Gly Val Thr Lys Lys Ile Lys
        435                 440                 445

Val Tyr Glu Tyr Gly Thr Val Ile Gln Asp Ala Val Asp Ile His Tyr
450                 455                 460

Pro Glu Asn Glu Met Thr Cys Asn Ser Lys Ile Ser Cys Ile Ser Trp
465                 470                 475                 480

Ser Ser Tyr His Lys Asn Leu Leu Ala Ser Ser Asp Tyr Glu Gly Thr
        485                 490                 495

Val Ile Leu Trp Asp Gly Phe Thr Gly Gln Arg Ser Lys Val Tyr Gln
        500                 505                 510

Glu His Glu Lys Arg Cys Trp Ser Val Asp Phe Asn Leu Met Asp Pro
        515                 520                 525

Lys Leu Leu Ala Ser Gly Ser Asp Asp Ala Lys Val Lys Leu Trp Ser
        530                 535                 540

Thr Asn Leu Asp Asn Ser Val Ala Ser Ile Glu Ala Lys Ala Asn Val
545                 550                 555                 560

Cys Cys Val Lys Phe Ser Pro Ser Ser Arg Tyr His Leu Ala Phe Gly
        565                 570                 575

Cys Ala Asp His Cys Val His Tyr Tyr Asp Leu Arg Asn Thr Lys Gln
        580                 585                 590

Pro Ile Met Val Phe Lys Gly His Arg Lys Ala Val Ser Tyr Ala Lys
        595                 600                 605

Phe Val Ser Gly Glu Glu Ile Val Ser Ala Ser Thr Asp Ser Gln Leu
        610                 615                 620

Lys Leu Trp Asn Val Gly Lys Pro Tyr Cys Leu Arg Ser Phe Lys Gly
625                 630                 635                 640

His Ile Asn Glu Lys Asn Phe Val Gly Leu Ala Ser Asn Gly Asp Tyr
        645                 650                 655

Ile Ala Cys Gly Ser Glu Asn Asn Ser Leu Tyr Leu Tyr Tyr Lys Gly
        660                 665                 670

Leu Ser Lys Thr Leu Leu Thr Phe Lys Phe Asp Thr Val Lys Ser Val
        675                 680                 685

Leu Asp Lys Asp Arg Lys Glu Asp Asp Thr Asn Glu Phe Val Ser Ala
        690                 695                 700

Val Cys Trp Arg Ala Leu Ser Asp Gly Glu Ser Asn Val Leu Ile Ala
705                 710                 715                 720

Ala Asn Ser Gln Gly Thr Ile Lys Val Leu Glu Leu Val
                725                 730

<210> SEQ ID NO 21
<211> LENGTH: 8
<212> TYPE: PRT
<213> ORGANISM: Artificial Sequence
<220> FEATURE:
<223> OTHER INFORMATION: Ser/Thr Kinase Catalytic Core Motif

<400> SEQUENCE: 21

His Arg Asp Leu Lys Pro Glu Asn
1               5

<210> SEQ ID NO 22
<211> LENGTH: 372
<212> TYPE: PRT
<213> ORGANISM: Mus musculus
<220> FEATURE:
<221> NAME/KEY: DOMAIN
<222> LOCATION: (342)..(360)
<223> OTHER INFORMATION: COP1 Binding Domain
```

<400> SEQUENCE: 22

| | | | | | | | | | | | | | | |
|---|---|---|---|---|---|---|---|---|---|---|---|---|---|---|
Met Arg Val Gly Pro Val Arg Phe Ala Leu Ser Gly Ala Ser Gln Pro
1               5                   10                  15

Arg Gly Pro Gly Leu Leu Phe Pro Ala Ala Arg Gly Thr Pro Ala Lys
            20                  25                  30

Arg Leu Leu Asp Thr Asp Asp Ala Gly Ala Val Ala Ala Lys Cys Pro
        35                  40                  45

Arg Leu Ser Glu Cys Ser Ser Pro Asp Tyr Leu Ser Pro Pro Gly
    50                  55                  60

Ser Pro Cys Ser Pro Gln Pro Pro Ser Thr Gln Gly Thr Gly Gly
65                  70                  75                  80

Ser Cys Val Ser Ser Pro Gly Pro Ser Arg Ile Ala Asp Tyr Leu Leu
                85                  90                  95

Leu Pro Leu Ala Glu Arg Glu His Val Ser Arg Ala Leu Cys Ile His
            100                 105                 110

Thr Gly Arg Glu Leu Arg Cys Lys Glu Phe Pro Ile Lys His Tyr Gln
            115                 120                 125

Asp Lys Ile Arg Pro Tyr Ile Gln Leu Pro Ser His Ser Asn Ile Thr
130                 135                 140

Gly Ile Val Glu Val Leu Leu Gly Ser Lys Ala Tyr Val Phe Phe
145                 150                 155                 160

Glu Lys Asp Phe Gly Asp Met His Ser Tyr Val Arg Ser Arg Lys Arg
                165                 170                 175

Leu Arg Glu Glu Glu Ala Ala Arg Leu Phe Lys Gln Ile Val Ser Ala
            180                 185                 190

Val Ala His Cys His Gln Ser Ala Ile Val Leu Gly Asp Leu Lys Leu
            195                 200                 205

Arg Lys Phe Val Phe Ser Thr Glu Glu Arg Thr Gln Leu Arg Leu Glu
210                 215                 220

Ser Leu Glu Asp Thr His Ile Ile Lys Gly Glu Asp Asp Ala Leu Ser
225                 230                 235                 240

Asp Lys His Gly Cys Pro Ala Tyr Val Ser Pro Glu Ile Leu Asn Thr
                245                 250                 255

Thr Gly Thr Tyr Ser Gly Lys Ala Ala Asp Val Trp Ser Leu Gly Val
            260                 265                 270

Met Leu Tyr Thr Leu Leu Val Gly Arg Tyr Pro Phe His Asp Ser Asp
            275                 280                 285

Pro Ser Ala Leu Phe Ser Lys Ile Arg Arg Gly Gln Phe Cys Ile Pro
290                 295                 300

Glu His Val Ser Pro Lys Ala Arg Cys Leu Ile Arg Ser Leu Leu Arg
305                 310                 315                 320

Arg Glu Pro Ser Glu Arg Leu Thr Ala Pro Gln Ile Leu Leu His Pro
            325                 330                 335

Trp Phe Glu Tyr Val Leu Glu Pro Gly Tyr Val Asp Ser Glu Ile Gly
            340                 345                 350

Thr Ser Asp Gln Ile Val Pro Glu Tyr Gln Glu Asp Ser Asp Ile Ser
            355                 360                 365

Ser Phe Phe Cys
        370

<210> SEQ ID NO 23
<211> LENGTH: 343
<212> TYPE: PRT
<213> ORGANISM: Mus musculus

```
<220> FEATURE:
<221> NAME/KEY: DOMAIN
<222> LOCATION: (312)..(331)
<223> OTHER INFORMATION: COP1 Binding Domain

<400> SEQUENCE: 23
```

| | | | | | | | | | | | | | | |
|---|---|---|---|---|---|---|---|---|---|---|---|---|---|---|
| Met | Asn | Ile | His | Arg | Ser | Thr | Pro | Ile | Thr | Ile | Ala | Arg | Tyr | Gly | Arg |
| 1 | | | | 5 | | | | | 10 | | | | | 15 | |
| Ser | Arg | Asn | Lys | Thr | Gln | Asp | Phe | Glu | Glu | Leu | Ser | Ser | Ile | Arg | Ser |
| | | | 20 | | | | | 25 | | | | | 30 | | |
| Ala | Glu | Pro | Ser | Gln | Ser | Phe | Ser | Pro | Asn | Leu | Gly | Ser | Pro | Ser | Pro |
| | | | 35 | | | | | 40 | | | | | 45 | | |
| Pro | Glu | Thr | Pro | Asn | Leu | Ser | His | Cys | Val | Ser | Cys | Ile | Gly | Lys | Tyr |
| | 50 | | | | | 55 | | | | | 60 | | | | |
| Leu | Leu | Leu | Glu | Pro | Leu | Glu | Gly | Asp | His | Val | Phe | Arg | Ala | Val | His |
| 65 | | | | | 70 | | | | | 75 | | | | | 80 |
| Leu | His | Ser | Gly | Glu | Glu | Leu | Val | Cys | Lys | Val | Phe | Glu | Ile | Ser | Cys |
| | | | | 85 | | | | | 90 | | | | | 95 | |
| Tyr | Gln | Glu | Ser | Leu | Ala | Pro | Cys | Phe | Cys | Leu | Ser | Ala | His | Ser | Asn |
| | | | 100 | | | | | 105 | | | | | 110 | | |
| Ile | Asn | Gln | Ile | Thr | Glu | Ile | Leu | Leu | Gly | Glu | Thr | Lys | Ala | Tyr | Val |
| | | | 115 | | | | | 120 | | | | | 125 | | |
| Phe | Phe | Glu | Arg | Ser | Tyr | Gly | Asp | Met | His | Ser | Phe | Val | Arg | Thr | Cys |
| 130 | | | | | 135 | | | | | 140 | | | | | |
| Lys | Lys | Leu | Arg | Glu | Glu | Ala | Ala | Arg | Leu | Phe | Tyr | Gln | Ile | Ala |
| 145 | | | | | 150 | | | | | 155 | | | | | 160 |
| Ser | Ala | Val | Ala | His | Cys | His | Asp | Gly | Gly | Leu | Val | Leu | Arg | Asp | Leu |
| | | | | 165 | | | | | 170 | | | | | 175 | |
| Lys | Leu | Arg | Lys | Phe | Ile | Phe | Lys | Asp | Glu | Arg | Thr | Arg | Val | Lys |
| | | | 180 | | | | | 185 | | | | | 190 | | |
| Leu | Glu | Ser | Leu | Glu | Asp | Ala | Tyr | Ile | Leu | Arg | Gly | Asp | Asp | Asp | Ser |
| | | | | 195 | | | | | 200 | | | | | 205 | |
| Leu | Ser | Asp | Lys | His | Gly | Cys | Pro | Ala | Tyr | Val | Ser | Pro | Glu | Ile | Leu |
| | 210 | | | | | 215 | | | | | 220 | | | | |
| Asn | Thr | Ser | Gly | Ser | Tyr | Ser | Gly | Lys | Ala | Ala | Asp | Val | Trp | Ser | Leu |
| 225 | | | | | 230 | | | | | 235 | | | | | 240 |
| Gly | Val | Met | Leu | Tyr | Thr | Met | Leu | Val | Gly | Arg | Tyr | Pro | Phe | His | Asp |
| | | | | 245 | | | | | 250 | | | | | 255 | |
| Ile | Glu | Pro | Ser | Ser | Leu | Phe | Ser | Lys | Ile | Arg | Arg | Gly | Gln | Phe | Asn |
| | | | 260 | | | | | 265 | | | | | 270 | | |
| Ile | Pro | Glu | Thr | Leu | Ser | Pro | Lys | Ala | Lys | Cys | Leu | Ile | Arg | Ser | Ile |
| | | | 275 | | | | | 280 | | | | | 285 | | |
| Leu | Arg | Arg | Glu | Pro | Ser | Glu | Arg | Leu | Thr | Ser | Gln | Glu | Ile | Leu | Asp |
| | 290 | | | | | 295 | | | | | 300 | | | | |
| His | Pro | Trp | Phe | Ser | Thr | Asp | Phe | Ser | Val | Ser | Asn | Ser | Gly | Phe | Gly |
| 305 | | | | | 310 | | | | | 315 | | | | | 320 |
| Ala | Lys | Glu | Ala | Cys | Asp | Gln | Leu | Val | Pro | Asp | Val | Asn | Met | Glu | Glu |
| | | | | 325 | | | | | 330 | | | | | 335 | |
| Asn | Leu | Asp | Pro | Phe | Phe | Asn |
| | | | 340 | | | |

```
<210> SEQ ID NO 24
<211> LENGTH: 484
<212> TYPE: PRT
<213> ORGANISM: Drosophila melanogaster
<220> FEATURE:
<221> NAME/KEY: DOMAIN
```

<222> LOCATION: (446)..(454)
<223> OTHER INFORMATION: COP1 Binding Domain

<400> SEQUENCE: 24

```
Met Asp Asn Ser Ser Gly Gln Asn Ser Arg Thr Ala Ser Ser Ala Ser
1               5                   10                  15

Thr Ser Lys Ile Val Asn Tyr Ser Ser Pro Val Ser Pro Gly Val Ala
            20                  25                  30

Ala Ala Thr Ser Ser Ser Ser Ser Ser Ser Gly Met Ser Ser
        35                  40                  45

Ser Gln Glu Asp Thr Val Leu Gly Leu Phe Thr Pro Lys Lys Glu Phe
    50                  55                  60

Pro Asn Ala Lys Met Leu Gln Thr Ile Arg Glu Lys Leu Met Thr Pro
65                  70                  75                  80

Gly Gly Ala Cys Asp Leu Leu Ala Leu Gly Ile Ala Ala Glu Pro Thr
                85                  90                  95

Asp Gln Gln Pro Val Lys Leu Ile Gln Gln Arg Tyr Leu Ile Ser Ala
                100                 105                 110

Gln Pro Ser His Ile Ser Ala Ala Val Ala Ala Lys Thr Pro Ala Ser
            115                 120                 125

Tyr Arg His Leu Val Asp Leu Thr Ala Ser Asn Leu Arg Cys Val Asp
        130                 135                 140

Ile Phe Thr Gly Glu Gln Phe Leu Cys Arg Ile Val Asn Glu Pro Leu
145                 150                 155                 160

His Lys Val Gln Arg Ala Tyr Phe Gln Leu Gln Gln His Asp Glu Glu
                165                 170                 175

Leu Arg Arg Ser Thr Ile Tyr Gly His Pro Leu Ile Arg Pro Val His
                180                 185                 190

Asp Ile Ile Pro Leu Thr Lys Asp Arg Thr Tyr Ile Leu Ile Ala Pro
            195                 200                 205

Val Pro Gln Glu Arg Asp Ser Thr Gly Val Thr Gly Val Tyr Glu
        210                 215                 220

Asn Leu His Thr Tyr Ile Arg His Ala Lys Arg Leu Cys Glu Thr Glu
225                 230                 235                 240

Ala Arg Ala Ile Phe His Gln Ile Cys Gln Thr Val Gln Val Cys His
                245                 250                 255

Arg Asn Gly Ile Ile Leu Arg Asp Leu Lys Leu Lys Arg Phe Tyr Phe
                260                 265                 270

Ile Asp Glu Ala Arg Thr Lys Leu Gln Tyr Glu Ser Leu Glu Gly Ser
            275                 280                 285

Met Ile Leu Asp Gly Glu Asp Asp Thr Leu Ser Asp Lys Ile Gly Cys
290                 295                 300

Pro Leu Tyr Thr Ala Pro Glu Leu Leu Cys Pro Gln Gln Thr Tyr Lys
305                 310                 315                 320

Gly Lys Pro Ala Asp Met Trp Ser Leu Gly Val Ile Leu Tyr Thr Met
                325                 330                 335

Leu Val Gly Gln Tyr Pro Phe Tyr Glu Lys Ala Asn Cys Asn Leu Ile
            340                 345                 350

Thr Val Ile Arg His Gly Asn Val Gln Ile Pro Leu Thr Leu Ser Lys
            355                 360                 365

Ser Val Arg Trp Leu Leu Ser Leu Leu Arg Lys Asp Tyr Thr Glu
        370                 375                 380

Arg Met Thr Ala Ser His Ile Phe Leu Thr Pro Trp Leu Arg Glu Gln
385                 390                 395                 400
```

```
Arg Pro Phe His Met Tyr Leu Pro Val Asp Val Glu Val Ala Glu Asp
                405                 410                 415
Trp Ser Asp Ala Glu Glu Asp Glu Gly Thr Ala Ala Asp Ala Met Asp
            420                 425                 430
Asp Asp Glu Glu Gly Leu Cys Pro Leu Gly Asp Lys His Glu Tyr Glu
        435                 440                 445
Asp Ile Gly Val Glu Pro Leu Asp Tyr Thr Arg Ser Thr Leu Gln Met
    450                 455                 460
Ala Gln Asn Ala Asn Gly Leu Ser Thr Glu Pro Glu Pro Asp Thr Asp
465                 470                 475                 480
Val Asp Met Gly

<210> SEQ ID NO 25
<211> LENGTH: 5
<212> TYPE: PRT
<213> ORGANISM: Artificial Sequence
<220> FEATURE:
<223> OTHER INFORMATION: COP1 binding motif concensus sequence
<220> FEATURE:
<221> NAME/KEY: MISC_FEATURE
<222> LOCATION: (2)..(2)
<223> OTHER INFORMATION: Xaa = Val (V) or Ile (I)
<220> FEATURE:
<221> NAME/KEY: MISC_FEATURE
<222> LOCATION: (5)..(5)
<223> OTHER INFORMATION: Xaa = Asp (D) or Glu (E)

<400> SEQUENCE: 25

Gln Xaa Val Pro Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: Mutated TRB3 COP1 Binding Motif (VPmt)

<400> SEQUENCE: 26

Ala Met Ala Gln Ala Ala Asp
1               5

<210> SEQ ID NO 27
<211> LENGTH: 20
<212> TYPE: DNA
<213> ORGANISM: Artificial Sequence
<220> FEATURE:
<223> OTHER INFORMATION: Forward Primer for Screening WT

<400> SEQUENCE: 27
gagctacacc tctggctgct                                          20

<210> SEQ ID NO 28
<211> LENGTH: 20
<212> TYPE: DNA
<213> ORGANISM: Artificial Sequence
<220> FEATURE:
<223> OTHER INFORMATION: Forward Primer for Screening Transgenics

<400> SEQUENCE: 28
catacagggt ctggtcatga                                          20

<210> SEQ ID NO 29
<211> LENGTH: 20
<212> TYPE: DNA
<213> ORGANISM: Artificial Sequence
```

```
<220> FEATURE:
<223> OTHER INFORMATION: Reverse Primer for Screening WT and Transgenics

<400> SEQUENCE: 29
ggtgtactct gtgcctgtgg                                                    20

<210> SEQ ID NO 30
<211> LENGTH: 19
<212> TYPE: DNA
<213> ORGANISM: Artificial Sequence
<220> FEATURE:
<223> OTHER INFORMATION: Mouse TRB3 RNAi oligonucleotide

<400> SEQUENCE: 30
acttgcactc cttagtacg                                                     19

<210> SEQ ID NO 31
<211> LENGTH: 19
<212> TYPE: DNA
<213> ORGANISM: Artificial Sequence
<220> FEATURE:
<223> OTHER INFORMATION: Mouse COP1 RNAi oligonucleotide

<400> SEQUENCE: 31
aactgaccaa gataacctt                                                     19

<210> SEQ ID NO 32
<211> LENGTH: 20
<212> TYPE: DNA
<213> ORGANISM: Artificial Sequence
<220> FEATURE:
<223> OTHER INFORMATION: Forward Primer for Lcad Amplification

<400> SEQUENCE: 32
acatgtggga gtacccgatt                                                    20

<210> SEQ ID NO 33
<211> LENGTH: 20
<212> TYPE: DNA
<213> ORGANISM: Artificial Sequence
<220> FEATURE:
<223> OTHER INFORMATION: Reverse Primer for Lcad Amplification

<400> SEQUENCE: 33
agaatccgca ttagctgcat                                                    20

<210> SEQ ID NO 34
<211> LENGTH: 20
<212> TYPE: DNA
<213> ORGANISM: Artificial Sequence
<220> FEATURE:
<223> OTHER INFORMATION: Forward Primer for Cpt1 Amplification

<400> SEQUENCE: 34
catgatcgca ggagaaaaca                                                    20

<210> SEQ ID NO 35
<211> LENGTH: 20
<212> TYPE: DNA
<213> ORGANISM: Artificial Sequence
<220> FEATURE:
<223> OTHER INFORMATION: Reverse Primer for Cpt1 Amplification

<400> SEQUENCE: 35
ggcagctggg gtatctcttt                                                    20
```

```
<210> SEQ ID NO 36
<211> LENGTH: 20
<212> TYPE: DNA
<213> ORGANISM: Artificial Sequence
<220> FEATURE:
<223> OTHER INFORMATION: Forward Primer for vlcad Amplification

<400> SEQUENCE: 36
acggcacagc atgagaaaat                                               20

<210> SEQ ID NO 37
<211> LENGTH: 20
<212> TYPE: DNA
<213> ORGANISM: Artificial Sequence
<220> FEATURE:
<223> OTHER INFORMATION: Reverse Primer for vlcad Amplification

<400> SEQUENCE: 37
gcatcagaga aggcacatga                                               20

<210> SEQ ID NO 38
<211> LENGTH: 20
<212> TYPE: DNA
<213> ORGANISM: Artificial Sequence
<220> FEATURE:
<223> OTHER INFORMATION: Forward Primer for ppara Amplification

<400> SEQUENCE: 38
tctgtgggct cactgttctg                                               20

<210> SEQ ID NO 39
<211> LENGTH: 20
<212> TYPE: DNA
<213> ORGANISM: Artificial Sequence
<220> FEATURE:
<223> OTHER INFORMATION: Reverse Primer for ppara Amplification

<400> SEQUENCE: 39
aactacctgc tcagggctca                                               20

<210> SEQ ID NO 40
<211> LENGTH: 20
<212> TYPE: DNA
<213> ORGANISM: Artificial Sequence
<220> FEATURE:
<223> OTHER INFORMATION: Forward Primer for Pgcla Amplification

<400> SEQUENCE: 40
caagtctaac tatgcagacc                                               20

<210> SEQ ID NO 41
<211> LENGTH: 20
<212> TYPE: DNA
<213> ORGANISM: Artificial Sequence
<220> FEATURE:
<223> OTHER INFORMATION: Reverse Primer for Pgcla Amplification

<400> SEQUENCE: 41
acttgctctt ggtggaagca                                               20

<210> SEQ ID NO 42
<211> LENGTH: 23
<212> TYPE: DNA
<213> ORGANISM: Artificial Sequence
<220> FEATURE:
<223> OTHER INFORMATION: Forward Primer for Ucp1 Amplification

<400> SEQUENCE: 42
```

```
ggcccttgta aacaacaaaa tac                                            23
```

<210> SEQ ID NO 43
<211> LENGTH: 23
<212> TYPE: DNA
<213> ORGANISM: Artificial Sequence
<220> FEATURE:
<223> OTHER INFORMATION: Reverse Primer for Ucp1 Amplification

<400> SEQUENCE: 43

```
ggcaacaaga gctgacagta aat                                            23
```

<210> SEQ ID NO 44
<211> LENGTH: 23
<212> TYPE: DNA
<213> ORGANISM: Artificial Sequence
<220> FEATURE:
<223> OTHER INFORMATION: Forward Primer for ppard Amplification

<400> SEQUENCE: 44

```
ctcttcatcg cggccatcat tct                                            23
```

<210> SEQ ID NO 45
<211> LENGTH: 23
<212> TYPE: DNA
<213> ORGANISM: Artificial Sequence
<220> FEATURE:
<223> OTHER INFORMATION: Reverse Primer for ppard Amplification

<400> SEQUENCE: 45

```
tctgccatct tctgcagcag ctt                                            23
```

<210> SEQ ID NO 46
<211> LENGTH: 20
<212> TYPE: DNA
<213> ORGANISM: Artificial Sequence
<220> FEATURE:
<223> OTHER INFORMATION: Forward Primer for Ucp2 Amplification

<400> SEQUENCE: 46

```
gatggcttgg cagtcaagaa                                                20
```

<210> SEQ ID NO 47
<211> LENGTH: 21
<212> TYPE: DNA
<213> ORGANISM: Artificial Sequence
<220> FEATURE:
<223> OTHER INFORMATION: Reverse Primer for Ucp2 Amplification

<400> SEQUENCE: 47

```
gaactcctgg aactcgagtt a                                              21
```

<210> SEQ ID NO 48
<211> LENGTH: 20
<212> TYPE: DNA
<213> ORGANISM: Artificial Sequence
<220> FEATURE:
<223> OTHER INFORMATION: Forward Primer for adpn Amplification

<400> SEQUENCE: 48

```
atctggaggt gggagaccaa                                                20
```

<210> SEQ ID NO 49
<211> LENGTH: 20
<212> TYPE: DNA
<213> ORGANISM: Artificial Sequence -continued

```
<220> FEATURE:
<223> OTHER INFORMATION: Reverse Primer for adpn Amplification

<400> SEQUENCE: 49
ccagtaaatg tagagtcgtt                                                    20
```

METHODS FOR IDENTIFYING CANDIDATE FAT-MOBILIZING AGENTS

CROSS-REFERENCE TO RELATED APPLICATION

This application claims the benefit of U.S. Provisional Application No. 60/804,275, filed Jun. 8, 2006.

ACKNOWLEDGEMENT OF GOVERNMENT SUPPORT

This invention was made with United States government support pursuant to grant no. RO1 DK064142, from The National Institutes of Health; the United States government has certain rights in the invention.

FIELD OF THE DISCLOSURE

Disclosed herein are methods for identifying agents capable of affecting the expression, posttranslational modification, and/or an activity of TRB3, for example, in adipose tissue and/or adipocytes. Such agents are useful, for example, to mobilize fat stores and as candidate obesity therapeutics.

BACKGROUND

TRB3 (also known as Nerve Growth Factor-induced Protein Kinase (NIPK); p65-interacting inhibitor of NFκB (SINK); or SKIP3) was first identified as a neuronal cell death-inducible putative protein kinase (NIPK) in the rat. TRB3 and its related family members TRB1 and TRB2 share 45% sequence identity overall and bear strong resemblances to Tribbles, a *Drosophila* protein that inhibits mitosis early in development by binding to the CDC25 homolog string and promoting its ubiquitination and proteasome-mediated degradation (Grosshans and Wieschaus, *Cell*, 101:523-31, 2000; Mata et al., *Cell*, 101:511-22, 2000; Rorth et al., *Mol. Cell.*, 6:23-30, 2000; Seher and Leptin, *Curr. Biol.*, 10:623-9, 2000). Like Tribbles, TRB family members have a truncated kinase domain that lacks an adenosine 5'-triphosphate binding site (GXGXXG) and contains a variant catalytic core motif within the Ser/Thr kinase domain (e.g., LRDLKLRR in mouse TRB3 (residues 180-187 of SEQ ID NO: 2) as compared to the catalytic core consensus sequence HRDLKPEN; SEQ ID NO: 21). Correspondingly, Tribbles and its mammalian counterparts lack detectable kinase activity by in vitro kinase assay, and are thought to have evolved instead as adaptor proteins (Du et al., *Science*, 300:1574-1577, 2003).

Using a yeast 2-hybrid assay, Du et al. identified TRB3 as a protein from a preadipocyte cDNA library that interacted with AKT1 (*Science*, 300:1574-1577, 2003). TRB3 disrupted insulin signaling in liver by binding directly to AKT and inhibiting activation of the kinase (Du et al., *Science*, 300: 1574-1577, 2003). Under fasting conditions, TRB3 expression was induced in liver. Amounts of TRB3 RNA and protein also were increased in livers of db/db diabetic mice compared with those of wild-type mice, and hepatic overexpression of TRB3 in amounts comparable to those in db/db mice promoted hyperglycemia and glucose intolerance. Du et al. (*Science*, 300:1574-1577, 2003) suggested that by interfering with AKT activation, TRB3 contributed to insulin resistance in individuals with susceptibility to type 2 diabetes. Indeed, humans with a gain of function mutation in TRB3 have a higher incidence of insulin resistance and diabetes-associated complications (Prudente et al., *Diabetes*, 54:2807-11, 2005).

Wu et al. cloned TRB3, which was designated SINK, from a human B-cell cDNA library (*J. Biol. Chem.*, 278:27072-27079, 2003). Northern blot analysis detected TRB3 mRNA in spleen, thymus, prostate, liver, and pancreas, but not in other tissues examined. Wu et al. found that overexpression of TRB3 in human embryonic kidney cells inhibited NFκB-dependent transcription induced by TNF or its downstream signaling proteins, but TRB3 did not inhibit NFκB translocation to the nucleus or binding of NFκB to DNA (*J. Biol. Chem.*, 278:27072-27079, 2003). Coimmunoprecipitation and in vitro kinase assays indicated that TRB3 specifically interacted with the NFκB transactivator p65 and inhibited p65 phosphorylation. Consistent with its role in inhibiting NFκB-dependent transcription, TRB3 also sensitized cells to apoptosis induced by TNF and TRAIL. Wu et al. concluded that TRB3 (SINK) was involved in a negative feedback control pathway of NFκB-induced gene expression (*J. Biol. Chem.*, 278:27072-27079, 2003).

Kiss-Toth et al. detected TRB3 expression in pancreas, peripheral blood leukocytes, and bone marrow, and found that overexpression of TRB3 in HeLa cells inhibited AP1 activity and blocked oncogenic Ras-driven AP1 activation (*J. Biol. Chem.*, 279:42703-42708, 2004). ERK activation was enhanced by TRB3, but only at low TRB3 doses. Coimmunoprecipitation and yeast 2-hybrid assays showed that MEK1 (MAP2K1) interacted with both TRB1 and TRB3, and MKK7 (MAP2K7) interacted specifically with TRB3. Cotransfection of MKK7 enhanced the level of TRB3, indicating that the TRIB-MAPKK interaction stabilized TRB3.

TRB3 and its related family members seem to be involved in important molecular, cellular and physiological processes; although, much remains to be discovered about these interesting psuedokinases and their uses, for example, in medicine, diagnostics, and/or the discovery of prospective and/or actual therapeutics. With particular regard to diseases of metabolic function (e.g., diabetes and obesity), new methods are needed for identifying useful candidate agents and therapeutics for the prevention and/or treatment of these increasingly common and serious disorders.

SUMMARY OF THE DISCLOSURE

During fasting adipose lipid stores are mobilized to provide fatty acids for use as a metabolic energy source. One known pathway for mobilization of lipid stores from adipose involves inactivating acetyl-CoA carboxylase (ACC), the rate-limiting enzyme in fatty acid synthesis, via a phosphorylation-dependence mechanism. This disclosure describes the unexpected discovery that TRB3 is a key component in a previously unknown parallel pathway for the mobilization of adipose lipids during fasting.

TRB3 is shown herein to promote fasting lipid metabolism via protein-protein interactions with E3 ubiquitin ligase Constitutive Photomorphogenic Protein 1 ((COP1) and ACC. TRB3 enhanced the COP1-dependent ubiquitination (and phosphorylation-independent) inactivation of ACC. In the process of stimulating lipid metabolism in adipose, TRB3 was itself phosphorylated and ubiquinated. Advantageously, activation of this TRB3 dependent pathway does not promote insulin resistance in vivo, results in free fatty acid profiles that resemble exercised humans and protects against diet-induced obesity.

This newly discovered TRB3-dependent pathway provides targets and markers for the identification of agents that enhance TRB3 activity in adipose, which agents, at least, are candidates or therapeutics for mobilizing adipose fat stores and in the treatment of disorders such as obesity.

The foregoing mad other features and advantages will become more apparent from the following detailed description of several embodiments, which proceeds with reference to the accompanying figures.

BRIEF DESCRIPTION OF THE FIGURES

Data are presented in the following figures as mean±s.e.m; n represents sample size for each cohort; and significant statistical differences are shown by *, $P<0.05$; and **, $P<0.01$.

FIG. 1A (top) shows the effect of fasting (F) on TRB3 mRNA and PGC-1α mRNA levels (fold-induction over refed (R)) in white (WAT) and brown (BAT) adipose tissue. FIG. 1A (bottom) shows by Western blot amounts of endogenous TRB3 protein in WAT from wild type mice tinder fasting or refed conditions. Amounts of HSP90 are shown for comparison. FIG. 1B shows immunofluorescence staining (top) and Western blot (bottom) analysis of WAT from transgenic mice expressing TRB3 (F-TRB3; tg) under control of the white and brown adipose specific aP2 promoter relative to control littermates (wt). Endogenous (endo) and Flag-tagged TRB3 proteins are indicated. FIG. 1C shows the effect of high fat diet on weight gain in F-TRB3 and control littermates over a 5-week period (n=8). FIG. 1D shows the relative mass of WAT (epididymal perineal) and BAT in control and F-TRB3 (Tg) mice, expressed as percent body weight (n=3). FIG. 1E shows the relative oxygen consumption (VO2) of high-fat diet challenged wild-type and F-TRB3 mice over a 24 hour period (n=4). FIG. 1F shows that F-TRB3 mice are protected from hepatic steatosis under high-fat diet (HFD) conditions. Representative sections from livers of 3 F-TRB3 trans genic and 3 wild-type mice on a HFD for 22 weeks are shown. Substantial accumulation of lipid droplets is seen in wt mice, but not in tg mice.

FIG. 2A shows levels of fatty acid oxidation in primary brown adipocytes from refed wildtype and F-TRB3 mice under normal chow and high fat diet conditions. BAT was isolated, and fatty acid oxidation was measured in adipocytes cultured for 12 hours in RPMI-1640 medium containing 0.6 mM oleate (2.5 µCi/mL, [9,10-$^3$H]). Data shown are the means±SEM of three experiments. FIG. 2B shows Q-PCR analysis of mRNAs for fatty acid oxidation and thermogenic genes in BAT (top) and WAT (bottom) from F-TRB3 and wild-type littermates maintained on a high fat diet for 22 weeks under fasting or refed conditions. FIG. 2C (left) shows by Western blot assay the recovery of Flag-tagged TRB3 from immunoprecipitates of HA-tagged ACC (top), and recovery of HA-tagged ACC1 from immunoprecipitations of Flag-tagged TRB3 (bottom) prepared from HEK293T cells. Input amounts for each protein are indicated. FIG. 2C (right) shows by Western blot assay recovery of endogenous ACC or fatty acid synthase (FASN) from immunoprecipitations with anti-TRB3 antiserum or control rabbit IgG prepared from WAT of fasted or refed wild-type mice. Input levels of ACC and FASN are shown. The TRB3 doublet in these studies corresponds to Ser51, Ser323 phosphorylated and de-phosphorylated forms of the protein (FIG. 12). FIG. 2D shows the fold-change in ACC activity (measured as cpm ($^{14}$C)/g tissue/min) in WAT from F-TRB3 transgenic mice relative to control littermates in the presence and absence of citrate, an allosteric activator of ACC.

FIG. 3A (left) shows by Western blot assay recovery of HA-tagged COP1 from immunoprecipitates of Flag-TRB3 prepared from HEK293T cells. Input levels of each protein are indicated. FIG. 3A (right) shows by Western blot assay recovery of endogenous COP1 protein by immunoprecipitation of WAT extracts from fasted or refed wild-type mice using anti-TRB3 or control IgG. FIG. 3B shows that TRB3 interacts directly with COP1 and ACC1. Far-western blot assay of HA-COP1 and HA-ACC1 immunoprecipitates prepared from HEK293T cells. Blots were probed with either wild-type or truncated (amino acids 1-315) recombinant GST-TRB3 proteins. Blots were then developed with anti-GST antiserum to detect binding of TRB3. Western blot assay on right of FIG. 3B shows immunoprecipitated COP1 and ACC1 proteins. FIG. 3C (top) shows by Western blot assay recovery of wild-type and COP1-interaction-defective VPmt mutant Flag-TRB3 from immunoprecipitates of HA-tagged COP1 prepared from HEK293T cells. FIG. 3C (bottom) shows an alignment of the conserved COP1 interaction motif in TRB3 homologs (from top to bottom: residues 342-360 of SEQ ID NO: 22, residues 312-331 of SEQ ID NO: 23, residues 319-338 of SEQ ID NO: 2, residues 446-454 of SEQ ID NO: 24, residues 327-340 of SEQ ID NO: 4, residues 327-340 of SEQ ID NO: 2, residues 349-362 of SEQ ID NO: 6, residues 349-362 of SEQ ID NO: 8, residues 442-455 of SEQ ID NO: 10, residues 331-344 of SEQ ID NO: 12, residues 303-316 of SEQ ID NO: 14). FIG. 3D shows the effect of TRB3 on association of COP1 with ACC1. Western blot assay showing recovery of HA-tagged TRB3 and HA-tagged COP1 from immunoprecipitates of Flag-tagged ACC1 prepared from HEK293T cells. Input levels of each protein are shown.

FIG. 4A (top) shows by Western blot of myc-ubiquitin recovered from immunoprecipitates of Flag-ACC1 the effect of wild-type and COP1-interaction-defective (VPmt) TRB3 on ubiquitination of ACC1 in HEK293T cells expressing COP1 as indicated. Amounts of ACC ubiquitination were determined by co-expressing myc-tagged ubiquitin. Total levels of ACC are shown for comparison. FIG. 4A (bottom) shows the effect of wild-type or COP1 interaction-defective (VPmt) TRB3 on ACC enzymatic activity in HEK293T expressing COP1 in the presence or absence of 2 mM citrate. Numbered sets of bars correspond to numbered lanes in Western blot assay, in FIG. 4A (top). FIG. 4B shows that TRB3 promotes ACC ubiquitination in adipose during fasting FIG. 4B (left) shows by Western blot assay recovery of endogenous ACC from, immunoprecipitations of anti-ubiquitin prepared from WAT of wild-type mice under fasting versus refed conditions. Input levels of ACC are shown. FIG. 4B (top right) shows the relative amounts of ubiquitinated ACC in BAT from wild-type and F-TRB3 transgenic mice. ACC was recovered from immunoprecipitations of BAT extracts using anti-ubiquitin antibody. FIG. 4B (bottom right) shows by Western blot amounts of endogenous COP1 recovered from immunoprecipitations of endogenous ACC prepared from BAT of wild-type and F-TRB3 mice as indicated. FIG. 4C shows that TRB3 promotes ACC degradation. FIG. 4C (top left) shows by Western blot amounts of ACC in WAT from control and transgenic littermates under HFD conditions. FIG. 4C (top right) shows by Western blot assay TRB3 and ACC protein amounts in control (USi) and Ad-TRB3 RNAi (T3i) expressing 3T3-L1 adipocytes. FIG. 4C (bottom left) shows the effect of control (USi) and lenti-TRB3 RNAi (T3i) on amounts of TRB3 and ACC protein in primary cultures of brown adipocytes. FIG. 4C (bottom right) shows by Western blot relative amounts of COP1 in BAT and liver extracts of wild-type mice. FIG. 4D is one non-binding model showing that fasting signals inhibit fatty acid synthesis via parallel pathways (AMPK, TRB3) that inactivate ACC via phosphorylation-dependent (AMPK) aid ubiquitin-dependent (TRB3) mechanisms, respectively.

FIG. 11 is a listing of mouse ACC1 peptides recovered from immunoprecipitates of Flag-tagged TRB3 in HEK293T cells. Residue number of SEQ ID NO: 15' corresponding to the second amino acid of each peptide is shown to the left of each peptide. The amino acid ranges of SEO ID NO: 15 for each peptide are listed to the right of each peptide.

FIG. 12 (top left, top right, and bottom left) show the results of two dimensional phospho-tryptic analysis of wild-type (WT), Ser51 Ala (S51A), and Ser323 Ala (S323A) mutant $^{32}$P-labeled TRB3 polypeptides from immunoprecipitates of transfected HEK293T cells. Arrows (1, 2) point to predominant phospho-tryptic spots. FIG. 12 (bottom) shows the results of western blot analysis of wild-type and phosphorylation defective mutant (Ser 51,323 Ala; S/A) TRB3 polypeptides in HEK293T cells. Note the disappearance of the slower-migrating TRB3 band in Ser/Ala mutant TRB3. Amounts of GFP from co-transfected GFP expression plasmid are shown for comparison.

These results show the association of TRB3 with ACC and COP1 in WAT was increased in F-TRB3 transgenic compared to control mice.

Figure 16:
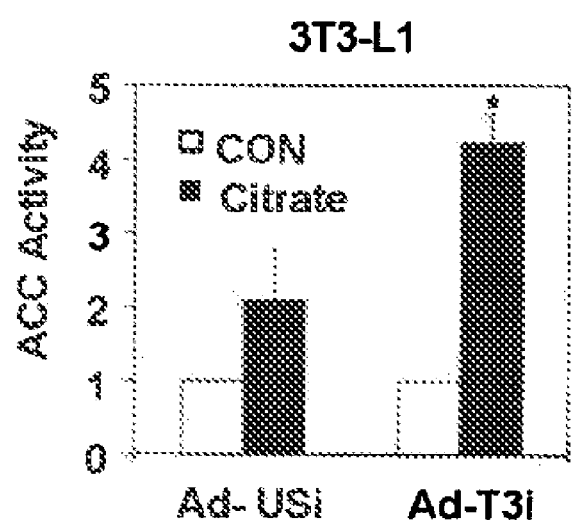

FIG. 16 is a bar graph showing ACC enzymatic activity in the presence (filled bars) or absence (open bars) of citrate in 3T3-L1 adipocytes transfected with Ad-TRB3 RNAi (Ad-T3i) or unspecific control Ad-RNAi (Ad-USi).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the filing date of this application. In the accompanying sequence listing:

SEQ ID NO: 1 shows a nucleic acid sequence of *Mus musculus* TRB3 (CDS residues 182-1246 of GenBank accession no. NM_175093 (gi28274687)).

SEQ ID NO. 2 shows an amino acid sequence of *Mus musculus* TRB3 (see also GenBank accession no, NP_780302 (gi28274688)), which amino acid sequence is encoded by SEQ ID NO: 1.

SEQ ID NO: 3 shows a nucleic acid sequence of *Homo sapiens* TRB3 (see also GenBank accession no. NM_021158 (gi41327717)).

SEQ ID NO: 4 shows an amino acid sequence of *Homo sapiens* TRB3 (see also GenBank accession no. NP_066981 (gi31542265)), which amino acid sequence is encoded by SEQ ID NO. 3.

SEQ ID NO. 5 shows a nucleic acid sequence of *Canis familiaris* TRB3 (CDS residues 1-1119 of GenBank accession no. XM_539160 (gi73974605)).

SEQ ID NO: 6 shows an amino acid sequence of *Canis familiaris* TRB3 (see also GenBank accession no, XP_539160 (gi73974606)), which amino acid sequence is encoded by SEQ ID NO: 5.

SEQ ID NO. 7 shows a nucleic acid sequence of *Bos taurus* TRB3 (see also CDS residues 458-1576 of GenBank accession no. XM_600128 (gi76660355)).

SEQ ID NO. 8 shows an amino acid sequence of *Bos taurus* TRB3 (see also GenBank accession no. XP_600128 (gi76660356)), which amino acid sequence is encoded by SEQ ID NO: 7.

SEQ ID NO. 9 shows a nucleic acid sequence of *Gallus gallus* TRB3 (see also GenBank accession no. XM_425946 (gi550732045)).

SEQ ID NO. 10 shows an amino acid sequence of *Gallus gallus* TRB3 (see also GenBank accession no. XP_425946 (gi50732046)), which amino acid sequence is encoded by SEQ ID NO: 9.

SEQ ID NO. 11 shows a nucleic acid sequence of *Xenopus laevis* TRB3 (see also CDS residues 173-1240 of Genbank accession no. B13073316 (gi49116791)).

SEQ ID NO. 12 shows an amino acid sequence of *Xenopus laevis* TRB3 (see also GenBank accession no. AAH73316 (gi49116792)), which amino acid sequence is encoded by SEQ ID NO: 11.

SEQ ID NO: 13 shows a nucleic acid sequence of *Apis mellifera* TRB3 (see also GenBank accession no. XM_392808 (gi66501272)).

SEQ ID NO: 14 shows an amino acid sequence of *Apis mellifera* TRB3 (see also GenBank accession no. XP_392808 (gi66501273)), which amino acid sequence is encoded by SEQ ID NO: 13.

SEQ ID NO: 15 shows an amino acid sequence of *Mus musculus* ACC1 (see also GenBank accession no. NP_579938 (gi60678241)).

SEQ ID NO: 16 shows an amino acid sequence of *Mus musculus* ACC2 (see also GenBank accession no. AAS13686 (gi42405898)).

SEQ ID NO. 17 shows an amino acid sequence of *Homo sapiens* ACC1 (see also GenBank accession no. NP_942131 (gi38679960)).

SEQ ID NO: 18 shows an amino acid sequence of *Homo sapiens* ACC2 (see also GenBank accession no. NP_001084 (gi61743950)).

SEQ ID NO. 19 shows an amino acid sequence of *Homo sapiens* COP1 (see also GenBank accession no. NP_071902 (gi21359963)).

SEQ ID NO. 20 shows an amino acid sequence of *Mus musculus* COP1 (see also GenBank accession no. NP_036061 (gi26024211)).

SEQ ID NO. 21 shows a consensus amino acid sequence of the catalytic core motif within the Ser/Thr kinase domain (HRDLKPEN).

SEQ ID NO: 22 shows an amino acid sequence of *Mus musculus* TRB1 (see also GenBank accession no. AAH06800 (gi13905034), which amino acid sequence is encoded, for instance, by nucleotides 94-1212 of GenBank accession no. BC006800 (gi133905033)).

SEQ ID NO: 23 shows an amino acid sequence of *Mus musculus* TRB2 (see also GenBank accession no. AAM45477 (gi21304716), which amino acid sequence is encoded, for instance, by nucleotides 151-1182 of GenBank accession no. AF358867 (gi21304715)).

SEQ ID NO: 24 shows an amino acid sequence of *Drosophila melanogaster* dTRB (see also GenBank accession no. NP_524672 (gi/7864238), which amino acid sequence is encoded, for instance, by nucleotides 354-1808 of GenBank accession no. NM_079933 (gi45549249)).

SEQ ID NO: 25 shows a COP1 binding motif consensus amino acid sequence (Q(V/I)VP(D/E)).

SEQ ID NO. 26 shows a mutated TRB3 COP1 binding motif (VPmt) (AMAQAAD)

SEQ ID NOs: 27-29 show the nucleic acid sequences of PCR primers used for screening wild type and transgenic animals.

SEQ ID NOs: 30 and 31 show an RNAi oligonucleotide sequence for mouse TRB3 or for mouse COP1, respectively.

SEQ ID NOs: 32-49 show the nucleic acid sequence of primers for Q-PCR analysis of mRNAs for fatty acid oxidation and thermogenic genes.

DETAILED DESCRIPTION

I. Introduction

Disclosed herein are methods of identifying an agent having potential to mobilize fat stores (and/or to treat or prevent obesity) in a subject. Such methods involve contacting with at least one test agent a test system that includes a TRB3 polypeptide (such as, a subject, an isolated cell or tissue, or an isolated TRB3 polypeptide); and detecting in the presence of the test agent(s) any one or more of the following: (a) increased expression of a nucleic acid encoding the TRB3 polypeptide (such as TRB3 mRNA); (b) increased expression of the TRB3 polypeptide; (c) a posttranslational modification of the TRB3 polypeptide (such as, phosphorylation and/or ubiquination (e.g., increased phosphorylation or increased ubiquination)); and/or (d) an enhanced activity of the TRB3 polypeptide (such as, increased formation of TRB3-COP1 complexes; increased formation of TRB3-ACC complexes; and/or increased TRB3-dependent ACC ubiquination). Detection of (a), (b), (c), and/or (d) identifies the at least one test agent as an agent having potential to mobilize fat stores (and/or to treat or prevent obesity) in the subject.

In particular methods, at least one test agent is administered to a subject having adipocytes including a TRB3 polypeptide. A further step of such particular methods involves detecting in the adipocytes in the presence of the test agent(s) any one of or more (a)-(d) above. In some of these methods, adipocytes are found in brown adipose tissue and/or white adipose tissue of the subject.

In other methods an isolated cell or tissue comprising a TRB3 polypeptide is contacted with at least one test agent; and any one or more of (a)-(d) described above are detecting in the isolated cell or tissue in the presence of the test agent(s). In some such methods, the isolated cell expresses endogenous TRB3 polypeptide. In other methods, the isolated cell expresses exogenous TRB3 polypeptide (and, optionally, may have substantially no endogenous TRB3 polypeptide); for example, the isolated cell can be stably or transiently transfected with an expression vector encoding the TRB3 polypeptide (and, optionally, one or both of a COP1 polypeptide aid/or an ACC polypeptide (such as, ACC1 or ACC2). In some cases, the isolated cell is an isolated adipocyte or an adipose cell line (such as 3T3-L1, PAZ6, T37i, 3T3-F442A, or HIB-1B).

Other exemplary methods involve contacting with at least one test agent an isolated TRB3 polypeptide and detecting in the presence of the at least one test agent an enhanced activity of the TRB3 polypeptide (such as, increased formation of TRB3-COP1 complexes; increased formation of TRB3-ACC complexes; and/or increased TRB3-dependent ACC ubiquination). Other such methods further involve contacting at least one test agent and an isolated TRB3 polypeptide with one or both of a COP-1 polypeptide and/or an ACC polypeptide, and detecting in the presence of the at least one test agent increased formation of TRB3-COP1 complexes, and/or increased formation of TRB3-ACC complexes.

Other methods of identifying an agent having potential to mobilize fat stores (and/or treat or prevent obesity) in a subject involve a cell that includes a nucleic acid sequence encoding a TRB3 polypeptide, or a reporter gene encoding a reporter polypeptide operably linked to a TRB3 transcription regulatory sequence. Such cell is contacting with at least one test agent and detected in the cell (in the presence of the test agent(s)) are an increase in the expression of the nucleic acid sequence encoding the TRB3 polypeptide or an increase in the expression of the reporter gene. A test agent having at least one of the foregoing effects is identified as an agent having potential to mobilize fat stores (and/or treat or prevent obesity) in a subject.

Still other methods are described for identifying an agent having potential to mobilize fat stores (and/or treat or prevent obesity) in a subject. Such methods involve: (a) providing a first component comprising a TRB3 polypeptide; (b) providing a second component comprising an ACC polypeptide (such as, an ACC1 and/or ACC2 polypeptide); (c) contacting the first component and the second component with at least one test agent under conditions that would permit the TRB3 polypeptide and the ACC polypeptide to specifically bind to each other in the absence of the at least one test agent; and (d) determining whether the at least one test agent affects (e.g., increases) the specific binding of the TRB3 polypeptide and the ACC polypeptide to each other. Those test agents having an effect on the specific binding of the TRB3 polypeptide and the ACC polypeptide to each other are identified as agents having potential to mobilize fat stores (and/or treat or prevent obesity) in a subject.

In some disclosed methods for identifying agent having potential to mobilize fat stores (and/or treat or prevent obesity) in a subject, at least three components are contacted with at least one test agent: A first component comprising a TRB3 polypeptide; a second component comprising an ACC polypeptide (such as, an ACC1 and/or ACC2 polypeptide), and a third component comprising a COP1 polypeptide. Such components are contacted with the test agent(s) under conditions that, in the absence of the test agent(s), would permit the TRB3 polypeptide, the ACC polypeptide, and the COP1 polypeptide to form a polypeptide complex, in which the TRB3 polypeptide specifically binds to the ACC polypeptide and the TRB3 polypeptide specifically binds to the COP1 polypeptide, and it is determined whether the at least one test agent affects (e.g., increases): (a) formation of the protein complex; (b) the specific binding of the TRB3 polypeptide and the ACC polypeptide; (c) the specific binding of the TRB3 polypeptide and the COP1 polypeptide; and/or (d) TRB3-dependent ubiquination of the ACC polypeptide.

Still other methods of identifying air agent having potential to mobilize fat stores (and/or treat or prevent obesity) in a subject are described. These methods involve: (a) contacting with a test agent a first test system comprising a first amount of a TRB3 polypeptide; (b) contacting with the test agent a second test system comprising substantially less of the TRB3 polypeptide than the first amount TRB3 polypeptide in the first test system; and (c) detecting in the presence of the test agent increased lipolysis and/or decreased fatty acid synthesis in the first test system as compared to the second test system. Detection of increased lipolysis and/or decreased fatty acid synthesis in the first test system as compared to the second test system identifies the test agent as ca agent having potential to mobilize fat stores in a subject, in some such methods, the first test system and the second test system are each isolated adipocytes, cells of the same adipose cell line, or cells of the same combination of adipocytes and/, or adipose cell lines. In other such methods, the first test system is a F-TRB3 transgenic mouse and the second test system is a wild-type mouse. In still other such methods, the first test system is a wild-type mouse and the second test system is a fat-specific TRB3 knock out mouse.

In any of the disclosed methods, a test agent is one or more of natural products, chemical compositions, biochemical compositions, polypeptides, peptides, or antibodies. Moreover, a test agent identified in any of the disclosed methods may be selected for further determination of its potential to treat or prevent obesity in a subject, and/or the adipose specificity of the effect that is detected in the presence of the agent (e.g., increased expression of a nucleic acid encoding the TRB3 polypeptide; increased expression of the TRB3 polypeptide; posttranslational modification of the TRB3 polypeptide; enhanced activity of the TRB3 polypeptide; increased lipolysis and/or decreased fatty acid synthesis; formation of a ACC:TRB3, ACC:TRB3:COP1 or TRB3:COP1 protein complex; specific binding of a TRB3 polypeptide and an ACC polypeptide; specific binding of a TRB3 polypeptide and a COP1 polypeptide; and/or TRB3-dependent ubiquination of the ACC polypeptide).

II. Abbreviations and Terms
  ACC acetyl-CoA carboxylase
  BAT brown adipose tissue
  FAO fatty acid oxidation
  FASN fatty acid synthase
  FFA free fatty acid(s)
  HFD high-fat diet
  Tg or tg transgenic
  WAT white adipose tissue
  WT or wt wild-type Unless otherwise rioted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8).

In order to facilitate review of the various embodiments of the invention, the following explanations of specific terms are provided:

Expression: The process by which the coded information of a nucleic acid transcriptional unit (including, for example, genomic DNA or cDNA) is converted into an operational, non-operational, or structural part of a cell, often including the synthesis of a polypeptide. Gene expression can be influenced by external signals; for instance, exposure of a cell, tissue or subject to an agent that enhances gene expression. Expression of a gene also may be regulated anywhere in the pathway from DNA to RNA to polypeptide. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof, Gene expression may be measured at the RNA level or the protein level and by any method known in the art, including, without limitation, Northern blot, RT-PCR, Western blot, or in vitro, in situ, or in vivo protein activity assay(s).

The expression of a nucleic acid may be modulated compared to a control state, such as at a control time (for example, prior to administration of a substance or agent that affects regulation of the nucleic acid under observation) or in a control cell or subject, or as compared to another nucleic acid. Such modulation includes but is not necessarily limited to overexpression, underexpression, or suppression of expression. In addition, it is understood that modulation of nucleic acid expression may be associated with, and in fact may result in, a modulation in the expression of an encoded polypeptide or even a polypeptide that at is not encoded by that nucleic acid (such as downstream regulated polypeptide(s)).

The expression of a polypeptide also may be modulated compared to a control state, such as at a control time (for example, prior to administration of a substance or agent that affects expression of a nucleic acid encoding or regulating the polypeptide) or in a control cell or subject, or as compared to another polypeptide. Modulation of polypeptide expression includes, but is not limited to, overexpression or decreased expression of the polypeptide, alteration of the subcellular localization or targeting of the polypeptide, alteration of the temporally regulated expression of the polypeptide (such that the polypeptide is expressed when it normally would not be, or alternatively is not expressed when it normally would be), alteration in the stability of the polypeptide, alteration in the spatial localization of the protein (such that the polypeptide is not expressed where it would normally be expressed or is expressed where it normally would not be expressed).

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a TRB3-encoding mRNA, or a TRB3-encoding dsDNA.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 989, chapters 9 and 11.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6×SSC, 5× Denhardt's solution, 0.5% SDS and 100 µg sheared salmon testes DNA, followed by 15-30 minute sequential washes at 65° C. in 2×SSC, 0.5% SDS, followed by 1×SSC, 0.5% SDS and finally 0.2×SSC, 0.5% SDS.

Isolated: An "isolated" biological component (such as a polynucleotide, polypeptide, or cell) has been purified away from other biological components in a mixed sample (such as a cell or tissue extract). For example, an "isolated" polypeptide or polynucleotide is a polypeptide or polynucleotide that has been separated from the other components of a cell in which the polypeptide or polynucleotide was present (such as an expression host cell for a recombinant polypeptide or polynucleotide).

The term "purified" refers to the removal of one or more extraneous components from a sample. For example, where recombinant polypeptides are expressed in host cells, the polypeptides are purified by, for example, the removal of host cell proteins thereby increasing the percent of recombinant polypeptides in the sample. Similarly, where a recombinant polynucleotide is present in host cells, the polynucleotide is purified by, for example, the removal of host cell polynucleotides thereby increasing the percent of recombinant polynucleotide in the sample. Isolated polypeptides or nucleic acid molecules, typically, comprise at least 50%, at least 60%, at least 70%, at least 80%, at least 90%, at least 95% or even over 99% (w/w or w/v) of a sample.

Polypeptides and nucleic acid molecules are isolated by methods commonly known in the art and as described herein. Purity of polypeptides or nucleic acid molecules may be determined by a number of well-known methods, such as polyacrylamide gel electrophoresis for polypeptides, or agarose gel electrophoresis for nucleic acid molecules.

Fat stores: Fatty acids, usually in the form of triglycerides, present in the cells of adipose tissue (such as brown adipose tissue or white adipose tissue). "Mobilizing (or mobilization of) fat stores" is a process whereby fatty acids stores (e.g., triglycerides) are converted to free fatty acids (e.g., by lipolysis) ultimately for metabolism in energy-producing pathways (such as via fatty acid oxidation).

Obesity: A state where a subject weighs more than a desirable standard or normal weight for a particular height, age and/or body structure (e.g., is at least overweight). Obesity can be determined by any of a variety of conventional measures. Body mass index (BMI), also called the Quetelet number, is one accepted calculation of excess body fat for sedentary, adult (but usually not elderly) bipeds (such as, human beings). BMI is calculated by dividing the subject's weight in kilograms by the square of his/her height in meters (BMI $kg/m^2$). Based on BMI, a subject may be categorized as normal weight (e.g., BMI=18.0-24.999), overweight (e.g., BMI=25.0-29.999), obese (e.g., BMI=30.0-34.999) or severely (or morbidly) obese (e.g., BMI of 35.0 or higher). An alternative way to determine obesity is to assess percent body fat. Generally, males with more than about 25% body fat and females with more than about 30% body fat are considered obese. An accepted method for measuring percentage body fat is to weigh a subject underwater. Simpler methods for measuring percentage body fat include the skinfold test or bioelectrical impedance analysis.

Operably linked: A first nucleic acid sequence is operably linked with a second nucleic acid sequence when the first nucleic acid sequence is in a functional relationship with the second nucleic acid sequence. For instance, a promoter is operably linked to a coding sequence if the promoter affects the transcription or expression of the coding sequence. When recombinantly produced, operably linked nucleic acid sequences are generally contiguous and, where necessary to join two protein-coding regions, in the same reading frame. However, nucleic acids need not be contiguous to be operably linked.

Regulatory region (or transcriptional regulatory sequence): A nucleic acid sequence comprising a plurality of cis-acting elements, including, without limitation, enhancers, silencers, promoters, transcription terminators, origins of replication, chromosomal integration sequences, 5' and 3', untranslated regions, exons and/or introns, which in combination form a functional unit that regulates the transcription of an operably linked second nucleic acid sequence. Typically, at least the predominant portion, of a regulatory region is found upstream (or 5') of the transcribable nucleic acid sequence (such as a gene) it regulates. In addition, a regulatory region, often, is contiguous (at least in part) with the transcribable sequence it controls. In a genome, some cis-acting elements regulating a particular transcribable nucleic acid sequence can be tens of kilobases away from the transcriptional start site. A "cis-acting regulatory element" or "cis-acting element" is a regulatory control element that is located on the same nucleic acid molecule as the gene (or other nucleic acid sequence) that it regulates. For example, an enhancer is a cis-acting element with respect to the gene whose transcription is increased by enhancer activation. Similarly, a silencer is a cis-acting element with respect to a gene (or other nucleic acid sequence) whose transcription is decreased by silencer activation.

Sequence identity: The similarity between two nucleic acid sequences or between two amino acid sequences is expressed in terms of the level of sequence identity shared between the sequences. Sequence identity is typically expressed in terms of percentage identity the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al. *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-2530, 1999. Altschul et al. present a detailed consideration of sequence-alignment methods and homology calculations (*J. Mol. Biol.* 215:403-4110, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda. MD) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater thin about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=-3]; reward for a match [default=1]; expectation value (E) [default=10.0]; word size [default=3]; number of one-line descriptions (V) [default=100]; number of alignments to show (B) [default=100]). When aligning short peptides (fewer than around 30 imino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 50%, at least 60%, at least 70%, at least 80%, at least 85%, at least 90%, at least 95%, or at least 98% sequence identity.

For comparisons of nucleic acid sequences, the "Blast 2 sequences" function of the BLAST™ (Blastn) program is employed using the default BLOSUM62 matrix set to default parameters (cost to open a gap, [default=11] cost to extend a gap [default=1]; expectation value (E) [default=10.0]3 word size [default=11] number of one-line descriptions (V) [default=100]; number of alignments to show (B) [default=100]) Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

Specific binding: Specific binding refers to the particular interaction between one binding partner (such as a binding agent) and another binding partner (such as a target). Such interaction is mediated by one or, typically, more noncovalent bonds between the binding partners (or, often, between a specific region or portion of each binding partner). In contrast to nonspecific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases wider these conditions, the amount of the first binding partner bound will saturate. In another contrast to non-specific binding sites, specific binding partners involved in a direct association with each other (e.g., a protein-protein interaction) can be competitively removed (or displaced) from such association (e.g., protein complex) by excess amounts of either specific binding partner. Such competition assays (or displacement assays) are very well known in the art.

Subject: Living multicellular vertebrate organisms, a category that includes both human and nonhuman animals (e.g., non-human mammals).

Preventing or treating a disease (or disorder): Preventing a disease (or disorder) refers to inhibiting the partial or full development or progression of the disease (or disorder), for example in a person who is known to have a predisposition to the disease (or disorder). With respect to a disease (or disorder) (such as obesity), "treating" or "treatment" includes (i) preventing the disease (or disorder), e.g., causing the clinical symptoms of the disease (or disorder) not to develop in a subject who does not yet experience or display symptoms of the disease (or disorder), (ii) inhibiting the disease (or disorder), e.g., arresting the development of the disease (or disorder) or its clinical symptoms, or (iii) relieving the disease (or disorder), e.g., causing regression of the disease (or disorder) or its clinical symptoms.

Vector: A nucleic acid molecule capable of transporting a non-vector nucleic acid sequence which has been introduced into the vector. One type of vector is a "plasmid," which refers to a circular double-stranded DNA into which non-plasmid DNA segments may be ligated. Other vectors include cosmids, bacterial artificial chromosomes (BAC) and yeast artificial chromosomes (YAC). Another type of vector is a viral vector, wherein additional DNA segments may be ligated into all or part of a viral genome. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as promoters) and are capable of directing the transcription of an expressible nucleic acid sequence that has been introduced into the vector. Such vectors are referred to as "expression vectors." A vector can also include one or more selectable marker genes and/or genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or", is intended to include "and" unless the context clearly indicates otherwise. "Comprising" means "including." Hence "comprising A or B" means "including A or B", or "including A and B." All publications, patent applications, patents, and other references mentioned herein are incorporated by reference in their entirety to the extent permitted by applicable laws and rules.

Materials, methods, and examples are illustrative only and not intended to be limiting. Methods and materials similar or equivalent to those described herein can be used in the practice or testing of the present invention (see, e.g., Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999).

III. Methods of Identifying Candidate Agents

This disclosure concerns the discovery of a pathway in adipose tissue that promotes mobilization of lipid stores. Activation of (or enhancing the activity of) this pathway in vivo produces lean subjects, who, at least, are resistant to high-fat diet-induced obesity, have free fatty acid profiles that resemble exercised humans, and have improved insulin sensitivity when fed a high-fat diet. It would be desirable to identity prospective agents that can activate or enhance the activity of this newly identified pathway in adipose, for example, to facilitate development of therapeutics, nutraceuticals or other agents that have one or more health-benefiting result(s), such as treatment and/or prevention of obesity.

A. Fat-Mobilizing Pathway in Adipose

A central component in the newly identified pathway is TRB3. Based on studies of TRB3 function in liver, this protein previously had been suggested to contribute to insulin resistance in individuals with susceptibility to type 2 diabetes. Concordantly, humans with a gain of function mutation in TRB3, which affects all cells of the body, have a higher incidence of insulin resistance and diabetes-associated complications (Prudente et al., *Diabetes*, 54:2807-11, 2005). Thus, the advantageous result of enhancing TRB3 function in adipose, as disclosed herein, was surprising and unexpected.

1. TRB3 Interacts with COP1

This disclosure demonstrates that TRB3 directly associates with COP1. A "direct association" between two or more polypeptides (such as, TRB3 and COP1, TRB3 and ACC (below) or ACC, TRB3 and COP1 (below)) is characterized by physical contact between at least a portion of the interacting polypeptides that is of sufficient affinity and specificity that, for example, immunoprecipitation of one of the polypeptides also will specifically precipitate the other polypeptide; provided that the immunoprecipitating, antibody does not also affect the site(s) involved in the interaction. A direct association between polypeptides also may be referred to as a "protein-protein interaction." Other exemplary methods of identifying protein-protein interactions include the yeast two-hybrid system (e.g., Fields and Song, *Nature*, 340:245-246, 1989: Fields and Sternglanz, *Trends Genet.*, 10(8):286-292, 1994) and the GST (or other epitope) pulldown assay.

COP1 was first identified in *Arabidopsis* as a repressor of light-regulated development (Deng et al., *Cell*, 71:791-801, 1992; Pepper et al., *Cell*, 78:109-16, 1994; von Arnim and Deng, *Cell*, 79:1035-45, 1994). Since then, COP1 homologs have been identified in several different species (including humans). COP1 is widely expressed in mammalian tissues and organs in both embryos and adults. COP1 proteins from all species identified to date have RING finger, coiled-coil, and WD40 domains. Mammalian COP1 proteins also have at least one nuclear localization signal (Yi et al. *BMC Cell Biol.*, 3:30, 2002).

COP1 is part of a multisubunit ubiquitin ligase, which also contains DNA damage-binding protein-1 (DDB1), cullin 4A (CUL4A), and regulator cullins-1 (ROC1) (Wertz et al., *Science*, 303:1371-1374, 2004). The COP1 RING finger domain exhibits ubiquitin ligase activity in vitro (Bianchi et al., *J. Biol. Chem.*, 278:19682-19690, 2003), and COP1 containing alanine substitutions at Cys136 and Cys139 in the RING domain is catalytically inactive (Wertz et al., *Science*, 303: 1371-4, 2004). A WD40 domain typically is 40 residues long and contains a GH dipeptide located 11-24 residues from its N-terminus and a WD dipeptide at its C-terminus. Between the GH and WD dipeptides is a conserved core that is believed to serve as a stable propeller-like platform to which proteins can bind either stably or reversibly. Consistent with this function, an interaction between COP1 and JUN is mediated by the COP1 WD40 repeats (Bianchi et al., *J. Biol. Chem.*, 278: 19682-19690, 2003). As shown in the Examples herein, the interaction between COP1 and TRB3 is mediated, in whole or in part, via the TRB3 C-terminal 40 amino acids, which contains a near-consensus COP1 binding motif.

2. TRB3 Interacts with ACC

Also newly disclosed herein is a direct interaction between TRB3 and ACC. ACC catalyzes the synthesis of malonyl-CoA from acetyl-CoA (Dowell et al., *Ann. Rev. Biochem.*, 74:515-34, 2005). At least two ACC isoforms (ACC1 and ACC2) have been characterized (Bianchi et al., *J. Biol. Chem.*, 65:1502-9, 1990; Thampy, *J. Biol. Chem.*, 264:17631-4, 1989). ACC1 is expressed primarily in lipogenic tissues including liver and adipose, whereas ACC2 primarily is targeted to oxidative tissues such as muscle and heart (Abu-Elheiga et al., *Proc. Natl. Acad. Sci. USA*, 92:4011-5, 1995; Ha et al., *Proc. Natl. Acad. Sci., USA* 93:11466-70, 1996; Lopaschuk et al., *J. Biol. Chem.*, 269: 25871-8, 1994). ACC1 (−/−) mice exhibit an embryonic lethal phenotype (Abu-Elheiga et al., *Proc. Natl. Acad. Sci. USA*, 102:12011-6, 2005). ACC2 (<mice are lean due to an increase in fatty acid and glucose oxidation in both muscle and adipose (Abu-Elheiga et al., *Proc. Natl. Acad. Sci. USA*, 100:10207-12, 2003; Oh et al., *Proc. Natl. Acad. Sci. USA*, 102: 1384-9, 2005).

3. One Non-Binding Model for TRB3-Dependent Fat Mobilization in Adipose

In one non-binding model (see FIG. 4D), fasting signals are believed to inhibit fatty acid synthesis via parallel pathways. One pathway, mediated by AMPK, inactivates ACC via a phosphorylation-dependent mechanism, and the other pathway, mediated by TRB3, inactivates ACC via a ubiquitin-dependent mechanism.

Although not bound by theory, TRB3 is believed to inhibit ACC activity by functioning as an adaptor for COP1 which ubiquinates ACC and leads to its degradation. The role of TRB3 in this context appears quite specific because no effect of TRB3 on ubiquitination or degradation of other COP1 substrates such as c-jun and p53 were observed. Indeed, fasting has previously been found to increase rates of ACC degradation 2-3 ibid in liver, although the underlying mechanism has not been addressed (Majerus and Kilburn, *J. Biol. Chem.*, 244:6254-62, 1969; Nakanishi and Numa, *Eur. J. Biochem.*, 16:161-73, 1970). Correspondingly, amounts of ACC protein in liver and adipose are reduced 6-8 fold in the fasted state, suggesting that changes in stability of ACC protein may contribute importantly to changes in lipid metabolism during this period (Iverson et al., *Biochem. J.*, 269:365-71, 1990)). Supporting this notion, Acc1p, the ACC homolog in budding yeast *S. cerevisiae*, also appears to be ubiquitinated and to associate with the 26S proteasome in large-scale proteomic studies (Peng et al., *Nat. Biotechnol.*, 21:921-6, 2003; Verma et al. *Mol. Biol. Cell*, 11:34245-39, 2000). As shown in the Examples (below), TRB3 and COP1 were capable of ubiquitinating and inhibiting ACC enzymatic activity in WAT and cultured adipocytes.

TRB3 accumulation in adipose appears to be blocked at least in part by its degradation via COP1-dependent ubiquination. As demonstrated in the Examples (below), TRB3 undergoes phosphorylation at (at least) two sites, Ser 51 and Ser 323. Ser323 is in close proximity to the COP1 binding site (amino acid residues 331-338) in TRB3, and may thereby modulate the TRB3:COP1 interaction. For example. COP1 appears to bind preferentially to phosphorylated relative to unphosphorylated TRB3 in co-immunoprecipitation studies; therefore, phosphorylated TRB3 may be a preferred target for COP1-dependent ubiquination.

As described in more detail below, the elucidation herein of the foregoing pathway provides numerous targets (e.g., TRB3-encoding nucleic acids, TRB3 polypeptides, TRB3:COP1 complexes, TRB3:ACC complexes, (COP1:TRB3:ACC complexes) and observable endpoints (e.g., ACC ubiquination, TRB3 ubiquination, TRB3 phosphorylation, increased lipolysis and/or fatty acid oxidation, TRB3 dependent decrease in ACC activity, increased interaction between components of any of the foregoing complexes, and/or increased TRB3 expression) that will be useful in the identification of agents with potential to mobilize adipose fat stores or treat or prevent obesity.

B. Representative Targets

Some disclosed methods generally involve one or more targets that may be affected in a particular manner by a test agent. In certain methods, a target is a TRB3 polypeptide and/or a nucleic acid encoding a TRB3 polypeptide. In other methods, a target is a protein complex including a TRB3 polypeptide, such as a TRB3:COP1 complex, TRB3:ACC complex, COP1:TRB3:ACC complex.

1. TRB3

A TRB3 polypeptide useful in a disclosed method is any known TRB3 polypeptide or homolog, functional fragment, or functional variant thereof. A TRB3 homolog, functional fragment, or functional variant retains at least one function described herein for a prototypical TRB3 polypeptide (e.g., mouse or human TRB3). In particular embodiments, a TRB3 polypeptide is any known TRB3 polypeptide or homolog, functional fragment, or functional variant thereof that can be substituted for the prototypical mouse TRB3 in any of the assays described in the Examples (below) and provide substantially the same result as described in the respective Example. For example, a TRB3 polypeptide is any known TRB3 polypeptide, or homolog, functional fragment, or functional variant thereof that, when overexpressed predominately (or substantially only) in adipose of a transgenic mouse, produces a subject that is lean, resistant to high fat diet-induced obesity, and has enhanced insulin sensitivity. In another example, a TRB3 polypeptide is any known TRB3 polypeptide, or homolog, functional fragment, or functional variant thereof that directly associates with an ACC poly peptide and/or a COP1 polypeptide.

The amino acid sequences of prototypical TRB3 polypeptides aid the nucleic acid sequences encoding the same are well known. Exemplary TRB3 sequences (nucleic acid sequence and amino acid sequence, respectively) from *Mus musculus* (SEQ ID NOs: 1 and 2), *Homo Sapien* (SEQ ID NOs: 3 and 4), *Canis familiaris* (SEQ ID NOs: 5 and 6), *Bos taurus* (SEQ ID NOs: 7 and 8), *Gallus gallus* (SEQ ID NOs: 9 and 10), *Xenopus laevis* (SEQ ID NOs: 11 and 12) and *Apis mellifera* (SEQ ID NOs: 13 and 14) have been provided. Routine comparison (e.g., using BLASTP software, for amino acid sequence, or BLASTN software, for nucleic acid sequences) of these (or other) prototypical TRB3 sequences against publicly available databases (such as GenBank non-redundant and/or patent databases) will reveal other TRB3 homologs. Any of these exemplary polypeptides are contemplated for use in some disclosed methods.

Exemplary TRB3 homologs or functional variants include polypeptides that share a particular degree of sequence identity with a prototypical TRB3 polypeptide (such as in SEQ ID NO, 2, 4, 6, 8, 10, 12, or 14) or that involve the substitution, insertion or deletion of one or several amino acids in a prototypical TRB3 polypeptide (including, e.g., splice variants).

In some method embodiments, a TRB3 polypeptide is a TRB3 homolog or functional variant having at least 60% amino acid sequence identity with a prototypical TRB3 polypeptide (such as in SEQ ID NO: 2, 4, 6, 8, 10, 12, or 14); for example, some TRB3 variants will share at least 75%, at least 80%, at least 85%, at least 90%, at least 95%, or at least 98% amino acid sequence identity with a sequence set forth in SEQ ID NO, 2, 4, 6, 8, 10, 12, or 14.

In other method embodiments, a TRB3 polypeptide is a FRB B3 functional variant having one or more conservative amino acid substitutions. Conservative substitutions are likely to have minimal impact on the activity of the resultant protein. Further information about conservative substitutions can be found, for instance, in Ben Bassat et al. (*J. Bacteriol.*, 169:751-757, 1987), O'Regan et al. (*Gene*, 777:237-251, 1989). Sahin-Toth et al., (*Protein Sci.*, 3:240-247, 1994), Hochuli et al. (*Bio/Technology*, 6:1321-1325, 1988) and in widely used textbooks of genetics and molecular biology. In some examples, a TRB3 homolog or functional variants can have no more than 3, 5, 10, 15, 20, 25, 30, 40, or 50 conservative amino acid changes compared to SEQ ID NO: 2, 4, 6, 8, 10, 12, or 14, as applicable. The following table shows exemplary conservative amino acid substitutions:

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

With known prototypical TRB3 amino acid sequences and corresponding nucleic acid sequences, TRB3 homologs aid variants are easily obtained by conventional molecular methods. For example, TRB3 homologs are naturally occurring and can be isolated by any of a myriad of protein purification techniques known in the art (for example, Scopes, *Protein Purification: Principles and Practice,* 3rd Edition, New York: Springer-Verlag, 1994; *Protein Purification Techniques,* 2nd Edition, ed. by Simon Roe, New York: Oxford University Press, 2001; *Membrane Protein Purification and Crystallization,* 2nd Edition, ed. by Hunte et al., San Diego: Academic Press, 2003). In other examples, a TRB3 variant can be produced by manipulation of a known TRB3-encoding nucleotide sequence (e.g., SEQ ID NO: 1, 3, 5, 7, 9, 11, or 13) using standard procedures, including without limitation the commonly known techniques of site-directed mutagenesis or PCR.

As demonstrated herein, fragments of TRB3 possess at least one substantially similar function as a full-length TRB3 protein (e.g., COP1 binding activity or ACC binding activity) or encompass known functional motifs (such as a COP1 binding motif) or posttranslationally modified residues (such as phosphorylated serine residues). Thus, some method embodiments involve the use of TRB3 functional fragments. A TRB3 functional fragment can be any portion of a full-length TRB3 polypeptide (such as SEQ ID NO: 2, 4, 6, 8, 10, 12, or 14), including, e.g., about 20, about 30, about 40, about 50, about 75, about 100, about 150 or about 200 contiguous amino acid residues of same.

Some embodiments involve a TRB3 functional fragment at least having COP1 binding activity, such as a C-terminal TRB3 fragment. More particular embodiments involve a TRB3 functional fragment including at least about or no more than about the 50 C-terminal residues (such as at least about or no more than about the 40 C-terminal residues, the 30 C-terminal residues, or the 25 C-terminal residues) of a prototypical TRB3 polypeptide (such as SEQ ID NO: 2, 4, 6, 8, 10, 12, or 14). Other method embodiments use a functional TRB3 fragment encompassing a COP1 binding motif, e.g., EMDQVVPD (residues 331-338 of SEQ ID NO: 2) or a COP1 binding motif consensus sequence, e.g., Q(V/I)VP(D/E) (SEQ ID NO: 25) or (Q/E)XVP (where X is selected from V, I, L, or D; see, e.g., FIG. 3C).

Other method embodiments involve a TRB3 functional fragment at least having ACC binding activity, such as an N-terminal TRB3 fragment. Particular embodiments involve a TRB3 N-terminal fragment having ACC binding activity that lacks no more than about or about the 40 C-terminal residues of a prototypical TRB3 polypeptide (such as SEQ ID NO: 2, 4, 6, 8, 10, 12, or 14). In some methods, a TRB3 N-terminal fragment having ACC binding activity is residues 1-315 of SEQ ID NO: 2, 4, 6, 8, 10, 12, or 14.

Still other method embodiments involve a TRB3 functional fragment encompassing at least one (such as one, two, three or four) Ser residues that are phosphorylated when the fat-mobilizing pathway disclosed herein is activated. For example, fragments of mouse TRB3 (SEQ ID NO: 2) encompassing phosphorylated residues Ser51 and/or Ser323 will be useful in some disclosed methods.

Some methods involve an endogenous TRB3 polypeptide while others involve exogenous TRB3 polypeptides. An endogenous TRB3 polypeptide is naturally expressed in a cell, tissue, or subject. An exogenous TRB3 polypeptide is not naturally expressed in a cell, tissue, or subject. An exogenous TRB3 polypeptide may be expressed in a cell, tissue or subject by any known method: for example, an expression vector including a TRB3-encoding nucleic acid sequence may be transfected (either stably or transiently) into a cell, tissue, or subject of interest.

Some method embodiments involve nucleic acid sequences encoding a TRB3 polypeptide (such as exemplary TRB3 polypeptides set forth in SEQ ID NO: 2, 4, 6, 8, 10, 12, or 14). Exemplary TRB3-encoding nucleic acid sequences are provided in SEQ ID NOs: 1, 3, 5, 7, 9, 11, and 13. It is common knowledge that a nucleic acid sequence can significantly differ from a prototype nucleic acid sequence and still encode the same, substantially the same, or a functionally equivalent polypeptide as the prototype sequence. Accordingly, other exemplary TRB3-encoding nucleic acid sequences for use in a disclosed method have at least about 60%, at least about 70%, at least about 80%, at least about 90%, at least about 95%, or at least about 98% sequence identity with a prototype TRB3 polynucleotide (such as SEQ ID NO: 1, 3, 5, 7, 9, 11, or 13).

Another conventional way to describe related nucleic acid sequences is by their tendency to specifically hybridize to each other under particular hybridization stringency conditions. Thus, other exemplar TRB3-encoding nucleic acid sequences for use in a disclosed method will hybridize to all or part of a prototypical TRB3 nucleic acid sequence (such as SEQ ID NO: 1, 3, 5, 7, 9, 11, or 13) under moderate stringency, medium stringency, high stringency or very high stringency conditions. In some instances, a hybridization probe will be at least about 30 contiguous nucleotides of a prototypical TRB3 nucleic acid sequence (such as at least about 50, at least about 100, at least about 200, at least about 300, at least about 500 or at least about 600 contiguous nucleotides).

2. TRB3 Complexes

A TRB3 polypeptide has been shown herein to associate both with a COP1 polypeptide or an ACC polypeptide: for example, to form a protein complex that can be immunoprecipitated with antibodies specific for TRB3 or, as applicable, COP1 or ACC. Although not bound by a particular mechanism, the association between TRB3 and COP1 and/or ACC is believed to have advantageous results, such as the inhibition of ACC activity thereby decreasing fatty acid synthesis and increasing fatty acid oxidation. Accordingly, agents that modify (e.g., enhance) a direct association between TRB3 and COP1 or TRB3 and ACC or among all three polypeptides, e.g., in adipose cells or tissue, may have a positive effect on fat metabolism and be useful in the treatment of disorders of fat metabolism, like obesity.

Modifying a protein-protein interaction means to alter or change such interaction from one state or condition to another; for example, to weaken, strengthen, disrupt, inhibit or enhance a TRB3:COP1, TRB3:ACC, or ACC:TRB3: COP1 interaction. In some examples, an interaction may be modified so as to completely disrupt the interaction, in which event the polypeptides involved in the interaction would not substantially interact under conditions that would normally permit the interaction. In other examples, an interaction may be weakened so that the polypeptides involved in the interaction do not interact as strongly as compared to an interaction between the polypeptides under control conditions. In still other examples, an interaction may be enhanced or strengthened, in which case the polypeptides involved in the interaction interact more strongly or to a greater extent than in an interaction between the polypeptides under control conditions.

In some methods, an interaction between a TRB3 polypeptide and a binding partner (such as a (COP1 polypeptide and/or an ACC polypeptide) is enhanced or strengthened. In at least some such methods, the level or activity of any direct or indirect indicator of the particular TRB3 binding partner(s) interaction is increased by at least about 2%, at least about 5%, at least about 10%, at least about 15%, at least about 25%, at least about 50%, or even more as compared to control measurements of the same indicator.

A COP1 polypeptide useful in a disclosed method is any known (COP1 polypeptide or homolog, functional fragment, or functional variant thereof. COP1 or COP1 homologs, functional fragments, or functional variants can be obtained using the same techniques as described in detail above for TRB3. A COP1 homolog, functional fragment, or functional variant retains at least one function described herein for a prototypical COP1 polypeptide (e.g., mouse or human COP1). In particular embodiments, a COP1 polypeptide is any known COP1 polypeptide or homolog, functional fragment, or functional variant thereof that can be substituted for the prototypical mouse COP1 polypeptide in any of the assays described in the Examples (below) and provide substantially the same result as described in the respective Example (e.g., binding to TRB3).

The amino acid sequences of prototypical (COP1 polypeptides (and COP1-encoding nucleic acid sequences) are well known. Exemplary COP1 amino acid sequences have been provided in SEQ ID NO. 19 (*Homo sapiens*) and SEQ ID NO: 20 (*Mus musculus*) and these exemplary polypeptides are contemplated for use in some disclosed methods. COP1 homologs, functional fragments, or functional variants useful in the disclosed methods are of the same scope as contemplated for TRB3 and described in detail above. Briefly, a COP1 polypeptide includes, in some method embodiments, a COP1 homolog or functional variant having at least 60% amino acid sequence identity with a prototypical COP1 polypeptide (such as in SEQ NO: 19 or 20); for example, some COP1 homologs or functional variants will share at least 75%, at least 80%, at least 85%, at least 90%, at least 95%, or at least 98% amino acid sequence identity with a sequence set forth in SEQ ID NO: 19 or 20. In other method embodiments, a COP1 polypeptide is a COP1 homolog or functional variant having one or more conservative amino acid substitutions as compared to SEQ ID NO, 19 or 20. In some examples, a COP1 homolog or functional variant can have no more than 3, 5, 10, 15, 20, 25, 30, 40, or 50 conservative amino acid changes compared to SEQ ID NO: 19 or 20, as applicable.

Some method embodiments involve a COP1 functional fragment, which can be any portion of a full-length described or otherwise known COP1 polypeptide (such as SEQ ID NO: 19 or 20), including, e.g., about 20, about 30, about 40, about 50, about 75, about 100, about 150 or about 200 contiguous amino acid residues of same. As described previously, COP1 encompasses known functional motifs (such as a RING finger domain and a WD40 domain). WD40 domains are believed to mediate, along other things, protein-protein interactions; thus, it is reasonable to expect that the (COP1 WD40 domain is involved in the COP1:TRB3 interaction described herein. Accordingly, in some method embodiments, a COP1 polypeptide includes a functional fragment encompassing the WD40 domain (such as, approximately residues 420 to 730 of SEQ ID NO: 19 or 20).

In some disclosed methods, a COP1-encoding polynucleotide may be useful, e.g., to express a COP1 polypeptide. In such methods, a COP1-encoding nucleic acid sequence can be any known nucleic acid sequence encoding COP1 (such as, Genbank accession no. gi50428922 (*Homo sapiens*) or gi52694683 (*Mus musculus*)) or nucleic acid sequences having at least about 60%, at least about 70%, at least about 80%, at least about 90%, at least about 95%, or at least about 98% sequence identity with any such known nucleic acid sequences.

An ACC polypeptide useful in a disclosed method is any known ACC polypeptide or isoform (such as ACC1 or ACC2), homolog, functional fragment, or functional variant thereof. ACC (such as ACC1 or ACC2) or ACC isoforms homologs, functional fragments, or functional variants can be obtained using the same techniques as described in detail above for TRB3. An ACC homolog, functional fragment, or functional variant retains at least one function described herein for a prototypical ACC polypeptide (e.g., mouse or human ACC1 or ACC2). In particular embodiments, an ACC polypeptide is any known ACC polypeptide or isoform, homology, functional fragment, or functional variant thereof that can be substituted for the prototypical mouse ACC1 or ACC2 polypeptide in any of the assays described in the Examples (below) and provide substantially the same result as described in the respective Example (e.g., binding to TRB3).

The amino acid sequences of prototypical ACC polypeptides (e.g., ACC1 or ACC2) (and ACC-encoding nucleic acid sequences) are well known. Exemplary ACC1 amino acid sequences have been provided in SEQ ID NO: 17 (*Homo sapiens*) and SEQ ID NO: 15 (*Mus musculus*). Exemplary ACC2 amino acid sequences have been provided in SEQ ID NO: 18 (Homo sapiens) and SEQ ID NO: 16 (*Mus musculus*). Any of these exemplary polypeptides is contemplated for use in some disclosed methods. ACC (such as ACC1 or ACC2) homologs, functional fragments, or functional variants useful in the disclosed methods are of the same scope as contemplated above for TRB3 and COP1. Briefly, an ACC polypeptide includes, in some method embodiments, an ACC isoform, homolog or functional variant having at least 60% amino acid sequence identity with a prototypical ACC polypeptide (such as in SEQ ID NO: 15, 16, 17 or 18); for example, some ACC isoforms, homologs or functional variants will share at least 75%, at least 80%, at least 85%, at least 90%, at least 95%, or at least 98% amino acid sequence identity with a sequence set forth in SEQ ID NO: 15, 16, 17, or 18. In other method embodiments, an ACC polypeptide is an isoform, homolog or functional variant having one or more conservative amino acid substitutions as compared to SEQ ID NO: 15, 16, 17, or 18. In some examples, an ACC isoform, homolog or functional variant can have no more than 3, 5, 10, 15, 20, 25, 30, 40, or 50 conservative amino acid changes compared to SEQ ID N)NO: 15, 16, 17, or 18.

An ACC functional fragment can be any portion of a full-length described or otherwise known ACC polypeptide (such as SEQ ID NO: 15, 16, 17, or 18), including, e.g., about 20, about 30, about 40, about 50, about 75, about 100, about 150 or about 200 contiguous amino) acid residues of same.

In some disclosed methods, an ACC-encoding polynucleotide may be useful, e.g., to express an ACC polypeptide (such as ACC1 or ACC2). In such methods, an ACC-encoding nucleic acid sequence can be any known nucleic acid sequence encoding ACC (such as, GenBank accession nos. gi38679959 (*Homo sapiens* ACC1) or gi60678240 (*Mus musculus* ACC1), gi61743949 (*Homo sapiens* ACC2) or gi42405897 (*Mus musculus* ACC2)) or nucleic acid sequences having at least about 60%, at least about 70%, at least about 80%, at least about 90%, at least about 95%, or at least about 98% sequence identity with any such known nucleic acid sequences.

C. Exemplary Agents

An "agent" is any substance or any combination of substances that is useful for achieving an end or result; for example, a substance or combination of substances useful for increasing gene expression or modulating a protein activity, or useful for modifying or affecting a protein-protein interaction. Any agent that has potential (whether or not ultimately realized) to modulate any feature of the TRB3 pathway disclosed herein is contemplated for use in the methods of this disclosure. For example, contemplated are agents that have potential to, in adipose tissue or cells, increase TRB3 mRNA or protein expression, affect an interaction (in vivo or in vitro) between TRB3 and either or both of COP1 or ACC (such as, ACC1 or ACC2), affect (e.g. increase or decrease) a post-translational modification of TRB3 (such as, phosphorylation or ubiquination) or enhance an activity of TRB3 (such as, increase ACC ubiquination, decrease ACC activity) or otherwise be a TRB3 mimetic.

Exemplary agents include, but are not limited to, peptides such as, for example, soluble peptides, including but not limited to members of random peptide libraries (see, e.g., Lam et al., *Nature*, 354:82-84, 1991, Houghten et al., *Nature*, 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyangy et al., *Cell*, 72:767-778, 1993), antibodies (including, but not limited to, polyclonal, monoclonal, humanized, anti-idiotypic, chimeric or single chain antibodies, and Fab, F-(ab')$_2$ and Fab expression library fragments, and epitope-binding fragments thereof), small organic or inorganic molecules (such as, so-called natural products or members of chemical combinatorial libraries), molecular complexes (such as protein complexes), or nucleic acids.

Libraries (such as combinatorial chemical libraries) useful in the disclosed methods include, but are not limited to, peptide libraries (see, e.g., U.S. Pat. No. 5,010,175; Furka, *Int. J. Pept. Prot. Res.*, 37:487-493, 1991; Houghton et al., *Nature*, 354:84-88, 1991; PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Natl. Acad. Sci. USA*, 90:6909-6913, 1993), vinylogous polypeptides (Hagihara et al., *J. Am. Chem. Soc.*, 114:6568, 1992), nonpeptidal peptidomimetics with glucose scaffolding (Hirschmann et al., *J. Am. Chem. Soc.*, 114:9217-9218, 1992), analogous organic syntheses of small compound libraries (Chen et al., *J. Am. Chem. Soc.*, 116:2661, 1994), oligocarbamates (Cho et al., *Science*, 261: 1303, 1003), and/or peptidyl phosphonates (Campbell et al., *J. Org. Chem.*, 59:658, 1994), nucleic acid libraries (see Sambrook et al. *Molecular Cloning, A Laboratory Manual*, Cold Springs Harbor Press, N.Y., 1989; Ausubel et al., *Current Protocols in Molecular Biology*, Green Publishing Associates and Wiley Interscience, N.Y., 1989), peptide nucleic acid libraries (see, e.g., U.S. Pat. No. 5,539,083), antibody libraries (see, e.g., Vaughn et al, *Nat. Biotechnol.*, 14:309-314, 1996; PCT App. No. PCT/US96/10287), carbohydrate libraries (see, e.g., Liang et al., *Science*, 274:1520-1522, 1996; U.S. Pat. No. 5,593,853), small organic molecule libraries (see, e.g., benzodiazepines, Baum, C&EN, Jan 18, page 33, 1993; isoprenoids, U.S. Pat. No. 5,569,588; thiazolidionones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514) and the like.

Libraries useful for the disclosed screening methods can be produce in a variety of manners including, but not limited to, spatially arrayed multipin peptide synthesis (Geysen, et al., *Proc. Natl. Acad. Sci.* 82(13):3998-4002, 1984), "tea bag" peptide synthesis (Houghten, *Proc. Natl. Acad. Sci.*, 82(15): 5131-5135, 1985), phage display (Scott and Smith, *Science*, 249:386-390, 1990), spot or disc synthesis (Dittrich et al., *Bioorg. Med. Chem. Lett.*, 8(17):2351-2356, 1998), or split and mix solid phase synthesis on beads (Furka et al., *Int. J. Pept. Protein Res.*, 37(6):487-493, 1991; Lam et al., *Chem. Rev.*, 97(2):411-448, 1997). Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one convenient embodiment, high throughput screening methods involve providing a combinatorial chemical or peptide library containing a large number of potential therapeutic compounds (e.g., potential fat-mobilizing agents, TRB3 mimetics, or affectors of TRB3 expression or function or TRB3 protein-protein interactions). Such combinatorial libraries are then screened in one or more assays as described herein to identify those library members (particularly chemical species or subclasses) that display a desired characteristic activity (such as, increasing TRB3 expression, enhancing TRB3 function, affecting a TRB3 posttranslational modification or affecting a TRB3 protein-protein interaction). The compounds thus identified can serve as conventional "lead compounds," or can themselves be used as potential or actual therapeutics. In some instances, pools of candidate agents may be identify and further screened to determine which individual or subpools of agents in the collective have a desired activity.

D. Assays

Screening methods may include, but are not limited to, methods employing solid phase, liquid phase, cell-based or virtual (in silico) screening assays. In one exemplary assay, compounds that affect (e.g., increase) at least one feature of the newly discovered TRB3 pathway are identified. For instance, certain assays may identify compounds that modulate (e.g., increase) the expression of a TRB3-encoding nucleic acid (e.g., DNA or mRNA) or TRB3 polypeptide, or that affect TRB3 gene regulatory sequences so as to modify (e.g., increase) TRB3 gene (and/or mRNA) expression. Other representative assays identify compounds that modify (e.g., enhance) a TRB3:COP1, TRB3: ACC, or ACC:TRB3:COP1 protein-protein interaction, or compounds that affect a TRB3 posttranslational modification (such as TRB3 phosphorylation or ubiquination) or TRB3-dependent ACC ubiquination. Still other exemplary assays identify compounds that affect lipid metabolism (such as increase lipolysis, decrease fatty acid synthesis or increase fatty acid oxidation) in a TRB3-dependent manner. Compounds identified via assays such as those described herein may be useful, for example, as fat mobilizing agents or for the treatment of disorders of fat metabolism, such as obesity.

TRB3 polypeptides, TRB3-encoding nucleic acid sequences, COP1 polypeptides, ACC polypeptides, and agents useful in any of the disclosed methods have been described in detail elsewhere herein. In addition, it is to be understood that disclosed methods involving the detection (or determination) of a change, modification, alteration, etc. (e.g., increase or decrease) in a particular composition or process, typically, are intended to be relative to a known or determined standard and/or control state, for example, as existed in the same test system prior to the addition of a test agent, or as existed in a comparable test system in the absence of a test agent.

1. Agents that Modulate One or More Features of the TRB3 Pathway

In one embodiment, a method of identifying an agent having potential to mobilize fat stores involves contacting a test system, which includes a TRB3 polypeptide (such as an endogenous TRB3 polypeptide), with at least one test agent (such as one test agent or a pool of test agents) and detecting in the presence of the test agent(s) a modified (e.g., increased) activity in any part of the newly discovered TRB3 pathway.

A test system useful in a disclosed method includes, for example, a subject (such as a F-TRB3 transgenic mouse), isolated adipose tissue (such as brown adipose tissue or white adipose tissue), isolated cells (such as primary adipocytes or adipocyte cell lines), or an isolated TRB3 polypeptide. In some methods involving a subject, isolated tissue, or isolated cell (such as an adipocyte), the newly discovered TRB3 pathway is intact. Accordingly, the effect (if any) of a test agent on any point in the pathway can be measured in such test system(s). In other methods, the TRB3 pathway discovered herein need not be intact in a test system (such as an isolated TRB3 polypeptide or an isolated cell expressing predominantly or only exogenous TRB3-, COP1, and/or ACC polypeptides) to identify agents having potential to mobilize fat stores.

In some methods involving isolated cells, such isolated cells (such as cell lines) express endogenous TRB3. Exemplary cells (or tissues from which cells can be obtained) that normally express TRB3 transcripts and/or polypeptides include adipocytes, (such as adipocytes isolated from brown adipose tissue or white adipose tissue), 3T3-L1 cells, PAZ6 cells, T37i cells, 3T3-F442A cells, and/or HIB-1B cells. Any of a variety of isolated cells (such as cell lines) can be used for methods involving isolated cells expressing exogenous TRB3, which cells sometimes have substantially no endogenous TRB3. Cells expressing exogenous TRB3 can be, for example, transiently or stably transfected with an expression vector encoding a TRB3 polypeptide. In other methods, an isolated cell can be stably or transiently transfected with one or more expression vectors encoding a TRB3 polypeptide and one or both of a COP1 polypeptide and/or an ACC polypeptide (such as, ACC1 or ACC2).

Test agents are screened in a test system for their effect on any relevant aspect of the newly discovered TRB3 pathway. In particular methods, the TRB3 pathway is activated or its activity is increased or enhanced. Such effects can be detected, for example, by increased expression of a TRB3-encoding nucleic acid, increased expression of a TRB3 polypeptide, a posttranslation modification of TRB3 (e.g., phosphorylation or ubiquination), or an increased activity of a TRB3 polypeptide in the pathway (such as increased binding affinity or amounts of TRB3:COP1, TRB3:ACC, or ACC:TRB3:COP1 complexes, increased TRB3-dependent inhibition of ACC activity, or TRB3-dependent ACC ubiquination).

A change in the expression of a TRB3-encoding nucleic acid (such as, a TRB3 gene or transcript) or polypeptide can be determined by any method known in the art. For example, the levels of a TRB3 transcript or polypeptide can be measured by standard techniques, such as, for RNA, Northern blot, PCR (including RT-PCR or q-PCR), in situ hybridization, or nucleic acid microarray, or, for protein, Western blot, antibody array, or immunohistochemistry. In some methods, the expression of a TRB3 mRNA can also be increased by increased stability of the mRNA. In particular methods, the expression of a TRB3-encoding nucleic acid (such as, a TRB3 gene or transcript) or polypeptide is increased when its level or activity is at least 10%, at least 20%, at least 30%, at least 50%, at least 100% or at least 250% higher than control measurements of the same indicator (e.g., in the same test system prior to addition of a test agent, or in a comparable test system in the absence of a test agent).

As disclosed herein, TRB3 and ACC are posttranslationally modified when the TRB3 fat-mobilizing pathway is activated. TRB3 is phosphorylated and ubiquinated and ACC is ubiquinated in a TRB3-dependent manner. Accordingly, disclosed are methods of screening test agents for those that increase TRB3 phosphorylation and ubiquination and that increase ACC ubiquination. Methods for detecting these common posttranslational protein modifications are conventional (see, e.g., Gloffke, *The Scientist*, 16(19):52, 2002; Screaton et al., *Cell*, 119:61-74, 2004) and detection kits are available from a variety of commercial sources (see, e.g., Upstate (Charlottesville, Va., USA), Bio-Rad (Hercules, (CA, USA), Marligen Biosciences, Inc. (Ijamsville, Md., USA), Calbiochem (San Diego, Calif., USA). Briefly, phosphorylated protein can be detected using stains specific for phosphorylated proteins in gels. Alternatively, antibodies specific phosphorylated proteins can be made or commercially obtained. Antibodies specific for phosphorylated proteins can be, among other things, tethered to the beads (including beads having a particular color signature) or used in ELISA or Western blot assays. Ubiquitinated polypeptide (e.g., ACC or TRB3) can be detected, for instance, by immunoprecipitating the polypeptide (e.g., ACC or TRB3) with anti-ubiquitin antiserum or antibodies followed by Western blot probed with antibody(ies) specific for the polypeptide of interest (e.g., ACC or TRB3). Alternatively, the ubiquinated polypeptide of interest (e.g., ACC or TRB3) can be immunoprecipitated with a polypeptide-specific antibody followed by Western blot probed with an anti-ubiquitin antibody (or antiserum). Antibodies specific for ubiquitin (and, therefore, ubiquinated polypeptides) are commercially available (see, e.g., Upstate (Charlottesville, Va., USA), Bethyl Laboratories, Inc. (Montgomery, Tex., USA), BIOMOL International, Inc. (Plymouth Meeting, Pa., USA) and many others).

In particular methods, the phosphorylation of TRB3 and/or the ubiquination of TRB3 or ACC is increased when such posttranslational modification is detectably measured or when such posttranslational modification is at least 20%, at least 30%, at least 50%, at least 100% or at least 250% higher than control measurements of the same indicator (e.g., in the same test system prior to addition of a test agent, or in a comparable test system in the absence of a test agent).

Also disclosed herein is the discovery that TRB3 interacts with both COP1 and ACC to form TRB3:COP1, TRB3:ACC, or ACC:TRB3:COP1 complexes. Without being bound by theory, the formation of a ACC:TRB3 COP1 complex in adipose tissue is believed to inhibit ACC and, consequently, inhibit fatty acid synthesis. Agents that facilitate the formation of, or enhance the interactions in, a TRB3:COP1, TRB3:ACC or ACC:TRB3:COP1 complex similarly have the potential to inhibit fatty acid synthesis in adipose and mobilize flat stores in a subject. In vitro methods of detecting an enhanced protein-protein interaction are discussed below. Test agents that modify (e.g., increase) the formation of TRB3:COP1, TRB3:ACC, or ACC:TRB3:COP1 complexes in a subject or isolated cell or tissue (such as adipocytes or adipose tissue) can be detected for instance, by determining (qualitatively or quantitative) the amounts of such complex(es) immunoprecipitated by an antibody specific for a component of the complex (or a tag present in such component, such as an HA tag, poly-His tag, myc tag, FLAG tag, or any other exogenous epitope tag), and/or by yeast two-hybrid assay where one or more test compounds are co-expressed with the target and prey constructs.

In particular methods, the formation of a TRB3:COP1, TRB3:ACC, or ACC:TRB3:COP1 complex is increased when the amount of such complex is at least 20%, at least 30%, at least 50%, at least 100% or at least 250% higher than a control measurement (e.g., in the same test system prior to addition of a test agent, or in a comparable test system in the absence of a test agent).

Alternatively, for each of the foregoing methods, subjects, isolated tissues, or isolated cells can be examined to determine whether one or more phenotypes have been altered in a manner consistent with modulation of expression of TRB3 polypeptides or polynucleotides, phosphorylation or ubiquination of TRB3, TRB3-dependent ubiquination of ACC, formation of TRB3:COP1, TRB3:ACC, or ACC:TRB3:COP1 complexes or, more generally, activation of the TRB3 pathway. Such phenotypes can include, without limitation, increased lipolysis, decreased fatty acid synthesis, or increased fatty acid oxidation (such as, at least 10%, at least 20%, at least 30%, at least 50%, at least 100% or at least 250% higher or lower, as applicable, than a control measurement).

2. Agents that Affect TRB3 Gene Expression

Also disclosed herein are methods of identifying agents that modulate the expression of a TRB3-encoding nucleic acid or a reporter gene operably linked to a TRB3 transcriptional regulatory sequence. Such agents have potential to mobilize fat stores in a subject and, or treat obesity. Generally, such methods involve contacting (directly or indirectly) with a test agent an expression system comprising a nucleic acid sequence encoding a TRB3 polypeptide, or a reporter gene operably linked to a TRB3 transcription regulatory sequence, and detecting a change (e.g., an increase) in the expression of the TRB3-encoding nucleic acid or reporter gene.

Modulation of the expression of a TRB3 gene or gene product (e.g., transcript or protein) can be determined using any expression system capable of expressing a TRB3 polypeptide or transcript (such as, a cell, tissue, or organism, or in vitro transcription or translation systems). In some embodiments, cell-based assays are performed. Non-limiting exemplary cell-based assays may involve test cells such as, cells (including cell lines) that normally express a TRB3 gene, its corresponding transcript(s) and/or TRB3 protein(s), or cells (including cell lines) that have been transiently transfected or stably transformed with a reporter construct driven by a regulatory sequence of a TRB3 gene.

As mentioned above, some disclosed methods involve cells (including cell lines) that have been transiently transfected or stably transformed with a reporter construct driven by a regulatory sequence of a TRB3 gene. A "regulatory sequence" as used herein can include some or all of the regulatory elements that regulate the expression of a particular nucleic acid sequence (such as, a TRB3 gene) under normal circumstances. In particular examples, a regulatory region includes the contiguous nucleotides located at least 100, at least 500, at least 1000, at least 2500, at least 5000, or at least 7500 nucleotides upstream of the transcriptional start site of the regulated, nucleic acid sequence (such as, a TRB3 gene). 4

TRB3 gene regulatory regions are provided for a variety of species (including non-primate, or non-primate, mammalian species) in publicly available genomic sequences. For example, human TRB3 is located on human chromosome 20 at location 20p13-p12.2 (GenBank Accession No. AC_0000637 (Build 36.1), current as of May 1, 2006). On human chromosome 20, the TRB3 gene (including exons and introns) is located from residue 309308 to residue 326203. Accordingly, a nucleic acid sequence of an upstream (i.e., 5') regulatory region of the human TRB3 gene includes at least 100, at least 500, at least 1000, at least 2500, at least 5000, at least 7500, or at least 10,000 nucleotides upstream of residue 309308 in GenBank AC_000063 (Build 36.1).

In method embodiments involving a cell transiently or stably transfected with a reporter construct operably linked to a TRB3 regulatory region, the level of the reporter gene product can be measured. Reporter genes are nucleic acid sequences that encode readily assayed proteins. Numerous reporter genes are commonly known and methods of their use are standard in the art. Non-limiting, representative reporter genes are luciferase, β-galactosidase, chloramphenicol acetyl transferase, alkaline phosphatase, green fluorescent protein, and others. In the applicable methods, the reporter gene product is detected using standard techniques for that particular reporter gene product (see, for example, manufacturer's directions for human placental alkaline phosphatase (SEAP), luciferase, or enhance green fluorescent protein (EGPF) available from BDBiosciences (Clontech); or galactosidase/ luciferase), luciferase, or galactosidase available from Applied Biosystems (Foster City, Calif., USA); or available from various other commercial manufacturers of reporter gene products). A difference in the level and/or activity of reporter gene measured in cells in the presence or absence of a test agent indicates that the test agent modulates the activity of the TRB3 regulatory region driving the reporter gene.

3. Agents that Affect an Interaction of TRB3 with COP1 and/or ACC

As disclosed herein, TRB3 form a protein-protein interaction with both COP1 and ACC, which protein complex is believed to lead to ubiquination of ACC inhibition of its enzymatic activity and, at least, decreased fatty acid synthesis. Agents that affect the TRB3:COP1, TRB3:ACC or ACC:TRB3:COP1 interaction (e.g, enhance the formation of a TRB3:COP1, TRB3:ACC or ACC:TRB3:COP1 complex, and/or increase the binding affinity of TRB3 to either COP1 or ACC) may also have the effect of inhibiting fatty acid synthesis and, therefore, are desirable to identify.

Agents that affect a TRB3:COP1, TRB3:ACC or ACC:TRB3:COP1 interaction can be identified by a variety of assays, including solid-phase or solution-based assays. In a solid-phase assay a TRB3 polypeptide (as described in detail elsewhere in this specification and which, in some embodiments, includes a COP1-binding fragment and/or an ACC-binding fragment of TRB3) and either or both of a COP1 polypeptide and/or an ACC polypeptide (each of which is described in detail elsewhere in this specification) are mixed under conditions in which TRB3 and COP1, TRB3 and ACC, or TRB3, ACC and COP1 normally interact (e.g., co-immunoprecipitate). One of the binding partners is labeled with a marker such as biotin, fluoroscein, EGFP, or enzymes to allow easy detection of the labeled component. The unlabeled binding partner(s) is (are) adsorbed to a support, such as a microtiter well or beads. Then, the labeled binding partner is added to the environment where the unlabeled binding partner(s) is (are) immobilized under conditions suitable for interaction between the two (or three) binding partners. One or more test compounds, such as compounds in one or more of the above-described libraries, are separately added to individual microenvironments containing the interacting binding partners. Agents capable of affecting the interaction between the binding partners are identified, for instance, as those that enhance retention or binding of the signal (i.e., labeled binding partner) in the reaction microenvironment, for example, in a microtiter well or on a bead for example. As discussed previously, combinations of agents can be evaluated in an initial screen to identify pools of agents to be tested individually, and this process is easily automated with currently available technology.

In still other methods, solution phase selection can be used to screen large complex libraries for agents that specifically affect protein-protein interactions (see, e.g., Boger et al., Bioorg. Med. Chem. Lett., 8(17):2339-2344, 1998); Berg et al., Proc. Natl. Acad. Sci., 99(6):3830-3835, 2002). In this example, each of two proteins that are capable of physical interaction (for example, TRB3 and COP1 or ACC polypeptides) are labeled with fluorescent dye molecule tags with different emission spectra and overlapping adsorption spectra. When these protein components are separate, the emission spectrum for each component is distinct and can be measured. When the protein components interact, fluorescence resonance energy transfer (FRET) occurs resulting in the transfer of energy from a donor dye molecule to an acceptor dye molecule without emission of a photon. The acceptor dye molecule alone emits photons (light) of a characteristic wavelength. Therefore, FRET allows one to determine the kinetics of two interacting molecules based on the emission spectra of the sample. Using this system, two labeled protein components are added under conditions where their interaction resulting in FRET emission spectra. Then, one or more test compounds, such as compounds in one or more of the above-described libraries, are added to the environment of the two labeled protein component mixture and emission spectra are measured. An increase in the FRET emission, with a concurrent decrease in the emission spectra of the separated components indicates that an agent (or pool of candidate agents) has affected (e.g., enhanced) the interaction between the protein components.

Because the formation of a ACC:TRB3:COP1 is believed to lead to TRB3-dependent ubiquination of ACC, the formation of an ACC:TRB3:COP1 complex in vitro can also be measured by the level of ACC ubiquination in the complex.

In certain method embodiments, one or more COP1 or ACC-binding fragments of TRB3 and/or one or more TRB3-binding fragments of COP1 or ACC are used. Polypeptide fragments having the desired binding activities have been previously discussed.

The disclosed methods contemplate the use of a TRB3, COP1 or ACC polypeptide contained, independently, in a cell or cellular extract, or as an isolated polypeptide.

In particular methods, the formation of a TRB3:COP1, TRB3:ACC, or ACC:TRB3:COP1 complex or the affinity of one or more subunits for the other(s) is increased when the amount of such complex or the binding affinity is at least 5%, at least 10%, at least 20%, at least 30%, at least 50%, at least 100%, or at least 250% higher than a control measurement (e.g., in the same test system prior to addition of a test agent, or in a comparable test system in the absence of a test agent).

Interactions between TRB3:COP1, TRB3:ACC, and/or ACC:TRB3:COP1 also can be quantified by co-immunoprecipitation of the relevant component polypeptides (e.g., from cellular extracts), by GST-pull down assay (e.g., using purified GST-tagged bacterial proteins), and/or by yeast two-hybrid assay, each of which methods is standard in the art. Conducting any one or more such assays in the presence and, optionally, absence of a test compound can be used to identity agents that improve or enhance the interaction between TRB3:COP1, TRB3:ACC, and/or ACC:TRB3:COP1 in the presence of the test compound as compared to in the absence of the test compound or as compared to some other standard or control.

4. Agents that Affect a TRB3 Functions

TRB3 overexpression in adipose of a living subject results in lean subjects, who are resistant to high-fat diet-induced obesity, at least in part, due to increased energy expenditure in such subjects. Advantageously, subjects overexpressing TRB3 in adipose did not exhibit insulin resistance, but rather demonstrated enhanced insulin sensitivity. It is desirable to identify agents having the potential to promote TRB3-dependent activity(ies) in adipose, at least, because such agents have the potential to mobilize fat stores and produce leaner subjects and are candidates for obesity therapeutics. Assays to identify such agents will generally involve detecting a TRB3-dependent functional (e.g., phenotypic) difference in an in vitro or in vivo assay system.

Representative assay systems that can be used to measure TRB3-dependent activity in the presence or absence of test agents include assays for decreased fatty acid synthesis (including, e.g., decreased ACC activity), increased fatty acid oxidation, or increased lipolysis. Exemplary assays for the measurement of lipolysis, fatty acid oxidation, in vivo metabolic activity and ACC enzymatic activity are provided in the Examples (e.g., Example 8). For example, triglyceride lipolysis produces glycerol, which can be detected (qualitatively or quantitatively) by, among other methods, incubation with glycerol kinase (to produce glycerol phosphate), glycerol phosphate oxidase (to produce $H_2O_2$), and horseradish peroxidase in the presence of a colorimetric substrate. One way to measure fatty acid oxidation is to provide cells with a radiolabeled ($^{14}C$ or $^3H$) fatty acid substrate and detect the release of a radiolabeled product formed by oxidation of the labeled fatty acid substrate; thus, for instance, $^{14}CO_2$ can be detected from cells provided a $^{14}C$-labeled fatty acid substrate (such as [$^{14}C$]-palmitic acid). Other methods for measuring the foregoing TRB3-dependent effects are commonly known (see, e.g., (Carpene et al., J. Lipid Res., 24(6):766, 1983; Steinberg et al., J. Biol. Chem., 236:1631-5, 1961; Boobis and Maughan, Clin. Chim. Acta., 132:173-9, 1983; Lynen, Meth. Enzymol., 5:443-451, 1962; Morita et al., Science, 288:140-1434, 2000; U.S. Pat. App. Pub. No. 20050221410, Wang et al., Assay Drug Dev. Technol., 2(1):63-9, 2004; Moon and Rhead, J. Clin. Invest., 79:59-64, 1987; Kudo et al., J. Biol. Chem., 270:17513-17520, 1995; Witters and Kemp, J. Biol. Chem., 267:2864-2867, 1992; Jarett et al., Endocrinol., 90:1277-84, 1972; Witters et al. J. Biol, Chem., 254:245-8, 1979; Blecher et al., J. Biol. Chem., 245:1867-70, 1970; Bray et al., J. Lipid Res., 9:714-9, 1968; Picard et al., Cell, 111: 931-41, 2002; Yin et al., J. Biol. Chem., 278:43074-80, 2003). Similarly kits are commercially available for the measure ment of lipolysis (e.g., Zen-Bio (Research Triangle Park, N.C., USA); Bio Cat (Heidelberg, Germany); tebu-bio) (Boechout, Belgium); Stratech Scientific (Cambridgshire, UK); Chemicon International (Temecula, Calif., USA).

In these method embodiments, the assay system is capable of carrying on the desired process, e.g., fatty acid synthesis (including, e.g., ACC activity), fatty acid oxidation, or lipolysis. For instance, certain cell-based systems (such as adipocytes, adipose cell lines (such as differentiated 3T3-L1 cells), or other cells expressing TRB3, ACC, and COP1), tissue-based systems (such as, brown and/or white adipose tissue) or living subjects are suitable for conducting such assays.

To ensure that an observed phenotype is attributable to a TRB3 polypeptide, a control assay system will express substantially no TRB3 (e.g., undetectable by Western blot) or substantially less TRB3 as compared to a non-control assay system. In this context, substantially less means at least 25% less, at least 50% less, at least 75%, or at least 90% less TRB3 in the control versus non-control assay system. A non-control assay (or test) system expresses or overexpresses TRB3 (or otherwise is treated to have more TRB3) as compared to control. In some examples, such expression or overexpression is achieved by transfecting one or more cells with an expression vector encoding the TRB3 polypeptide.

In particular method embodiments, a first test system and a second test system are each isolated adipocytes, cells of the sane adipose cell line, or cells of the same (or a substantially similar) combination of adipocytes and/or adipose cell lines. In other method embodiments, a first test system is a F-TRB3 transgenic mouse and a second test system is a wild-type mouse. In still other method embodiments, a first test system, is a wild-type mouse and a second test system is a fat-specific TRB3 knock out mouse.

One or more test agents are contacted to the control and non-control assay systems (e.g., cells of such assay systems), and a TRB3-dependent phenotype (such as, decreased fatty acid synthesis, decreased ACC activity, increased fatty acid oxidation, or increased lipolysis) is detected. An agent having potential to mobilize fat stores (or treat obesity) is one for which at least one TRB3-dependent functional phenotype differs in the non-control, TRB3 expressing or overexpressing system as compared to the control system.

In some cell-based method embodiments described here and throughout the specification, test cells or test agents can be presented in a manner suitable for high-throughput screening; for example, one or a plurality of test cells can be seeded into wells of a microtitre plate, and one or a plurality of test agents can be added to the wells of the microtitre plate. Alternatively, one or a plurality of test agents can be presented in a high-throughput format, such as in wells of microtitre plate (either in solution or adhered to the surface of the plate), and contacted with one or a plurality of test cells under conditions that, at least, sustain the test cells. Test agents can be added to test cells at any concentration that is not lethal to the cells. It is expected that different test agents will have different effective concentrations. Thus in some methods, it is advantageous to test a range of test agent concentrations.

5. Adipose Specificity

TRB3 overexpression, activation, or increased activity in adipose tissue in vivo has advantageous effects as described herein. Thus, it may be beneficial, in some instances, to further determine whether the effect(s) of an agent identified in some method embodiments is (are) adipose specific; that is, the effect(s) is (are) observed substantially only in adipose tissues or cells and is (are) substantially absent in non-adipose tissues or cells.

Alternatively, disclosed methods for identifying fat-mobilizing agents may have usefulness in the treatment of obesity. Thus, it further may be beneficial (although optional) to further screen agents identified in some method embodiments for their potential to treat or prevent, obesity in a subject; for example by administering a candidate agent to an obese subject (such as am animal model of obesity) and determining whether the obese phenotype is treated by the candidate agent (such as by weight loss in the subject). In another example, a candidate agent is administered to an obese or normal-weight subject, who is then fed a high-fat diet, and subsequent weight gain (if any) is detected. A candidate agent that prevents weight gain or induces weight loss in a subject fed a high-fait diet similarly may be considered as an agent having potential to treat or prevent obesity.

EXAMPLES

The following examples are provided to illustrate certain particular features and/or embodiments. These examples should not be construed to limit the invention to the particular features or embodiments described.

Example 1

Transgenic Mice Overexpressing TRB3 in Adipose are Lean and Resistant to High Fat Diet-Induced Obesity This Example illustrates that TRB3 overexpression in adipose mobilizes adipocyte fat stores resulting in leaner subjects with enhanced insulin sensitivity.

Figure 1:
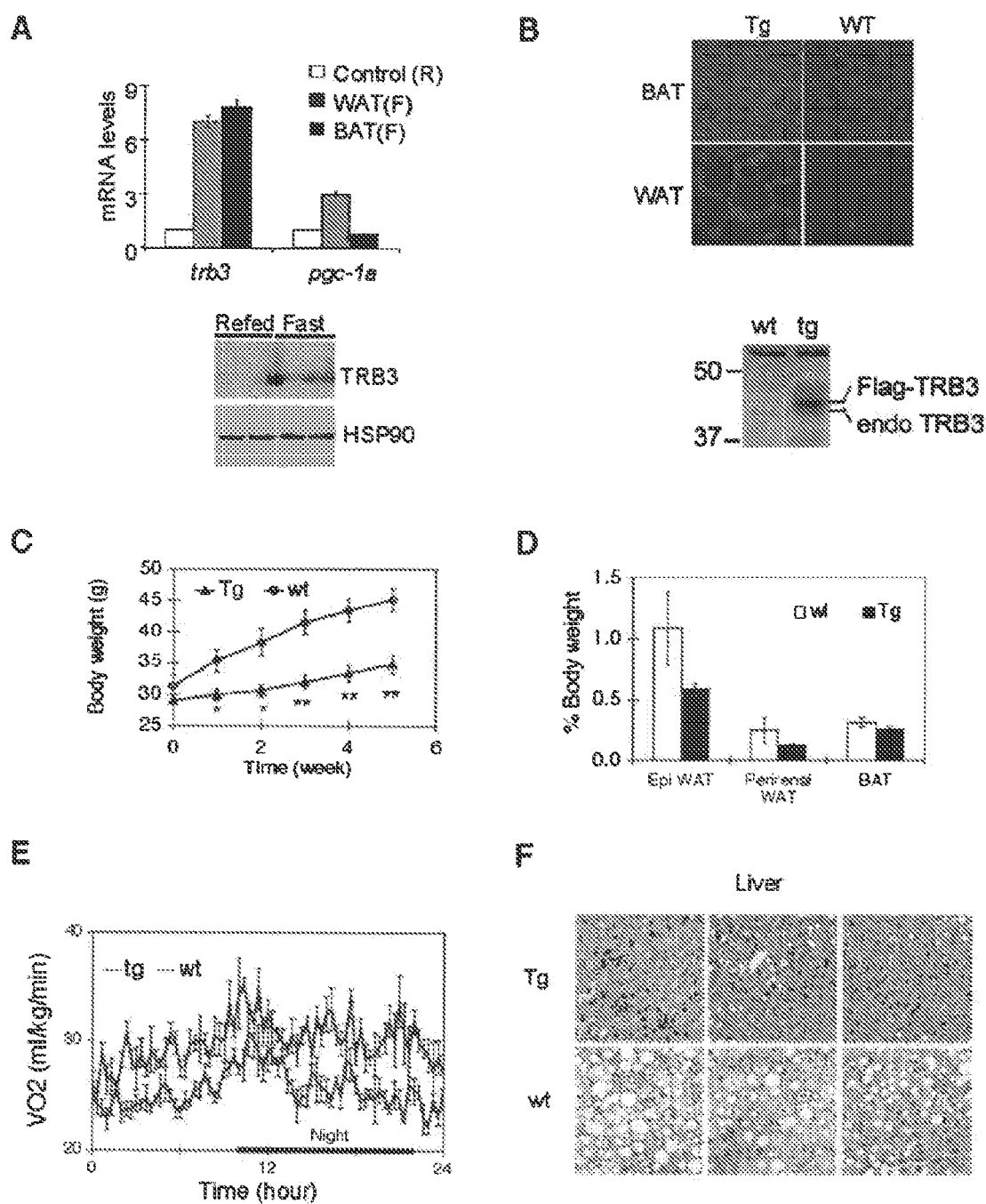
FIG. 1 includes several panels showing that transgenic mice expressing TRB3 in adipose are protected from diet-induced obesity.
Figure 5:
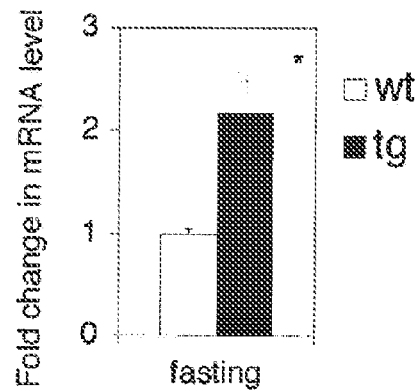
FIG. 5 is a bar graph comparing TRB3 mRNA levels in WAT of F-TRB3 transgenic versus wild-type littermates under fasting conditions.

To determine the metabolic effects of TRB3 in adipose tissue, two independent lines of transgenic mice expressing TRB3 from the adipose-specific aP2 promoter (F-TRB3 mice) were generated. In wild-type mice, amounts of TRB3 mRNA and protein in brown and white adipose tissue (BAT and WAT) were increased during fasting relative to refed conditions (FIG. 1A). In F-TRB3 mice, TRB3 mRNA and protein levels mice were 2 to 4 fold higher in WAT and BAT, and on a par with TRB3 levels in IRS1 (−/−) adipocytes (6-fold elevated) (Tseng et al., *Nat. Cell Biol.*, 7:601-11, 2005) (FIGS. 1B and 5).

Figure 6:
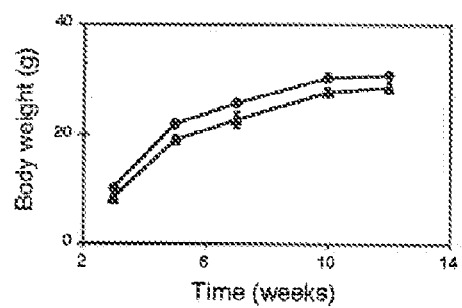
FIG. 6 shows growth curves for wild-type and F-TRB3 liters. F-TRB3 mice (triangles) exhibit lower body weights relative to control littermates (diamonds) on normal chow diet at each of the indicated time points.
Figure 7:
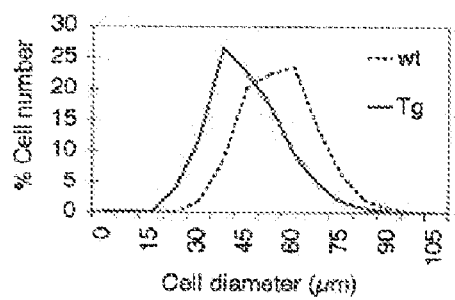
FIG. 7 is a line graph showing the relative numbers of cells of the indicated cell sizes (n=390) in WAT sections from wild-type (dotted line) and F-TRB3 mice (solid line) (n=4).
Figure 8:
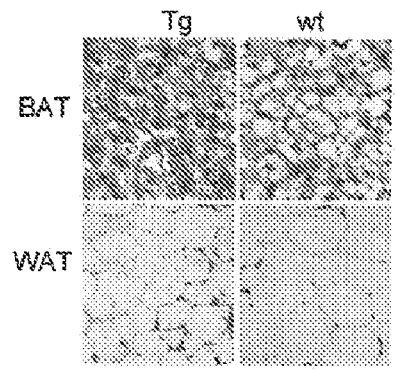
FIG. 8 are digital representations of H&E-stained sections from WAT and BAT of F-TRB3 (Tg) and control (wt) littermates showing decreased cell size and lipid content in F-TRB3 cells.

F-TRB3 mice were indistinguishable from control littermates at birth, but gained weight more slowly and had about 10% lower body mass at 8 weeks of age on a normal chow diet (FIG. 6). Under high-fat diet (HFD) conditions, however, F-TRB3 mice showed far lower weight gains compared with wild-type littermates (FIG. 1C). Epididymal and perirenal fat pads were each reduced about 50% in F-TRB3 mice, whereas BAT mass was decreased to a lesser extent (FIG. 1D). Histologically, BAT and WAT tissues from F-TRB3 animals had comparable cellularity to wild-type littermates; but average adipocyte size was significantly lower in F-TRB3 adipose, indicating that fat burning is enhanced in these mice (FIGS. 7 and 8).

Metabolic studies were conducted to determine why adiposity was reduced in F-TRB3 mice. Although physical activity was comparable between both groups, F-TRB3 mice actually consumed 20% more calories than control littermates (Table 1). Plasma metabolites were measured from mice under either fasting (17 hours) or ad libitum feeding conditions. Mice were maintained either on normal chow diet or 60% HFD for 6-7 weeks.

TABLE 1

Physiological plasma parameters of wt and Fa1-TRB3 to mice.

| | Normal chow diet (12% fat, 8-12 wk. n = 5-10) | | | | High-test diet (60% fat, 6-7 wk. n = 5) | | | |
|---|---|---|---|---|---|---|---|---|
| | Fasting | | Feeding | | Fasting | | Feeding | |
| | wt | tg | wt | tg | wt | tg | wt | tg |
| Energy intake (cal/day/g BW) | | | 696.1 ± 57.9 | 796.5 ± 9.9 | | | 285.0 ± 27.6 | 328.0 ± 35.4 |
| Glucose (mg/al) | 95.3 ± 3.3 | 78.3 ± 6.0* | 1729 ± 12.4 | 156.0 ± 8.9 | 196.1 ± 9.3 | 145.1 ± 9.9* | 186.3 ± 9.5 | 160.1 ± 6.7* |
| Triglycaride (mg/al) | 68.5 ± 2.9 | 63.3 ± 2.6 | 73.8 ± 3.5 | 62.3 ± 4.8 | 72.1 ± 2.6 | 73.1 ± 3.1 | 96.1 ± 11.9 | 69.3 ± 4.4* |
| β-hydroxybutyrate (mg/al) | 10.8 ± 1.1 | 98 ± 1.1 | 6.0 ± 0.5 | 5.3 ± 0.4 | 7.3 ± 0.7 | 6.9 ± 0.9 | 3.1 ± 0.3 | 5.2 ± 0.8* |
| Fatty acid (nmoll) | 709.1 ± 38.6 | 925.2 ± 80.7* | 271.5 ± 18.8 | 248.8 ± 50.6 | 696.6 ± 25.4 | 861.8 ± 25.2* | 220.8 ± 22.9 | 277.5 ± 23.4* |
| Inaulin (ng/ml) | 0.52 ± 0.06 | 0.51 ± 0.07 | 1.45 ± 0.23 | 2.15 ± 0.13 | 1.49 ± 0.32 | 0.96 ± 0.23 | 5.6 ± 1.1 | 3.8 ± 0.5 |
| Laptin (ng/ml) | 0.15 ± 0.05 | 0.39 ± 0.15 | 2.49 ± 0.62 | 3.53 ± 0.65 | 21.4 ± 1.9 | 7.1 ± 1.4** | 28.3 ± 3.5 | 13.2 ± 2.6** |
| Cholesterol (mg/al) | | | | | 250.4 ± 3.7 | 217.1 ± 11.8* | | |

N, mouse numbers.
*, P < 0.05;
**, P < 0.005 by two-tailed student's t-test assuming unequal variances.

Under HFD conditions, F-TRB3 mice showed a robust increase in $O_2$ consumption (31.04±0.30 (Tg) vs. 26.22±0.32 (WT) ml $O_2$/kg/min; FIG. 1E) as well as a persistent elevation in core body temperatures relative to controls (FIG. 1E) indicating that F-TRB3 mice are lean in part due to increased energy expenditure.

Free fatty acids (FFAs) were elevated in F-TRB3 mice compared to control littermates particularly under fasting conditions (Table 1). Notably, unsaturated fatty acids were increased preferentially over saturated fatty acids in F-TRB3 mice and resembled FFA profiles from exercised humans (Mougios et al., *Metabolism*, 44:681-8, 1995).

Figure 9:
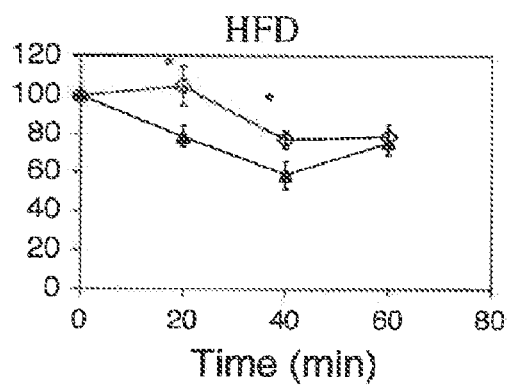
FIG. 9 is a graph showing the results of insulin tolerance tests (ITT) of F-TRB3 transgenic (open diamonds) and wild-type littermates (closed triangles) maintained under high fat diet conditions. Mice were injected i.p. with insulin (1 U/kg), and circulating glucose levels were monitored.

HFD feeding is thought to trigger insulin resistance in part by promoting lipid accumulation in the liver (hepatic steatosis). Hepatic steatosis was readily observed in control littermates on a HFD; but lipid accumulation was far less pronounced in livers of F-TRB3 mice (FIG. 1F). Correspondingly, F-TRB3 animals exhibited lower circulating glucose and insulin levels (Table 1); and they were more insulin sensitive than wild-type littermates by insulin tolerance test (FIG. 9).

Figure 2:
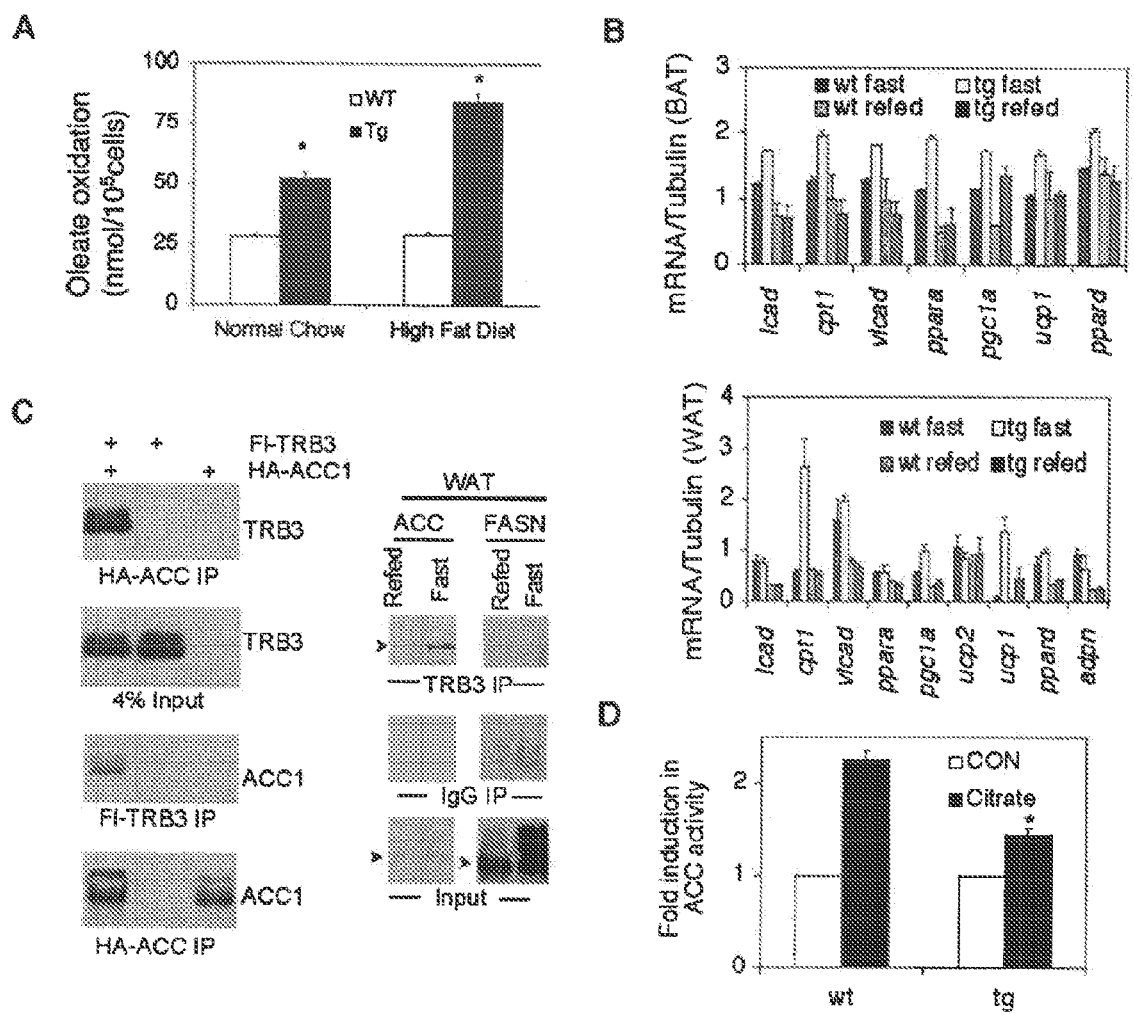
FIG. 2 panels collectively illustrate that TRB3 promotes fatty acid oxidation by disrupting acetyl-CoA carboxylase (ACC) activity.
Figure 10:
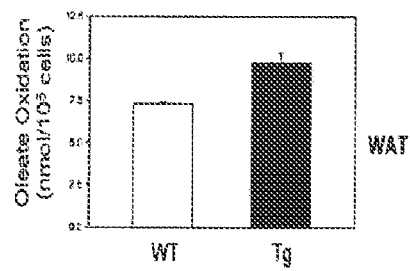
FIG. 10 is a bar graph showing levels of fatty acid oxidation in primary white adipocytes from refed wild-type (WT) and F-TRB3 (Tg) mice under normal chow conditions, WAT was isolated, and fatty acid oxidation was measured in adipocytes cultured for 12 hours in RPMI-1640 media containing 0.6 mM oleate (2.5 µCi/mL, [9,10-$^3$H]). Data shown are the means±SEM of three experiments.

In view of their elevated energy expenditure, F-TRB3 mice could be protected from hepatic steatosis due to a compensatory increase in fat burning. In fact, basal rates of fatty acid oxidation (FAO) in BAT and WAT were elevated 1.5 to 2 fold on normal chow and 3-fold on a HFD in F-TRB3 mice relative to control littermates (FIGS. 2A and 10). Correspondingly, FAO genes were upregulated in WAT and BAT from F-TRB3 mice compared to control littermates. mRNAs for key transcriptional regulators (PGC-1α, PPARα, and PPARδ) and FAO enzymes (CPT1; 4.6 fold higher) were significantly induced (FIG. 2B). Consistent with the elevated core body temperatures, amounts of uncoupling protein 1 (UCP1) mRNA were increased nearly 14-fold in WAT from F-TRB3 relative to control mice, indicating that TRB3 protects against diet-induced obesity by enhancing rates of fatty acid oxidation and subsequently dissipating this energy in part via thermogenesis.

Example 2

TRB3 Directly Interacts ACC and Inhibits ACC Enzymatic Activity

This Example demonstrates that TRB3 associates directly with ACC and inhibits its enzymatic activity.

Proteomic studies were performed to identify cellular proteins that associate with TRB3. Acetyl-CoA carboxylase 1 (ACC1), the rate limiting enzyme in fatty acid synthesis (Ruderman et al., *Endocrinol.*, 144:5166-71, 200) was recovered from immunoprecipitates of Flag-tagged TRB3 with significant sequence coverage (FIG. 11). The TRB3:ACC interaction was also observed in reciprocal co-immunoprecipitation (co-IP) studies using epitope-tagged TRB3 and ACC1 polypeptides (FIG. 2C, left) and in co-IPs of native proteins from WAT of wild-type mice under fasting but not refed conditions (FIG. 2C, right). Other enzymes in the fatty acid synthesis pathway such as fatty acid synthase (FASN) did not interact with TRB3), which indicates that the TRB3 interaction is specific for ACC.

Notably, mice with a knockout of the ACC2 −/− gene exhibit a lean phenotype, and are resistant to diet-induced obesity, due in part to an increase in fatty acid oxidation in adipose (Abu-Elheiga et al., *Proc. Natl. Acad Sci. USA*, 100: 10207-12, 2003; Oh et al., *Proc. Natl. Acad. Sci, USA*, 102: 1384-9, 2005). The phenotypic similarity between ACC2 −/− mice and F-TRB3 mice suggests a linkage between the metabolic effects of TRB3 and its association with ACC. Fittingly, in enzymatic assays, ACC activity was about 2-fold lower in WAT from F-TRB3 mice compared to normal littermates (FIG. 2D, left). Adenoviral TRB3 also inhibited ACC activity acutely in 3T3-L1 adipocytes indicating that the effects of TRB3 on ACC likely are cell autonomous.

Example 3

TRB3 Modulates ACC Activity Via a Phosphorylation-Independent Pathway

ACC enzymatic activity during fasting is inhibited by PKA and AMPK-mediated phosphorylation (Hardie and Guy, *Eur. J. Biochem.*, 110:167-77, 1980; Munday et al., *Eur. J. Biochem.*, 175:331-8, 1988). TRB3-expressing adenovirus (Ad-TRB3) had no effect on amounts of phospho (Ser79) ACC relative to total ACC protein in 3T3-L1 adipocytes. Likewise, the proportion of phospho (Ser79) ACC relative to total ACC in BAT and WAT was comparable between F-TRB3 mice and control littermates. AMPK activity, assessed by amounts of Thr172 phosphorylation (Mitchelhill et al., *J. Biol. Chem.*, 272:24475-9, 1997), was also indistinguishable between both groups, arguing against an effect of TRB3 on this phosphorylation-dependent pathway. Despite its ability to block activation of the Ser/Thr kinase AKT in liver following insulin stimulation (Du et al., *Science,* 300:1574-1577, 2003), TRB3 did not appear to disrupt this pathway in adipose because amounts of phospho (Ser473) AKT in WAT and BAT were comparable between F-TRB3 and control mice. Taken together, this Example illustrates that TRB3 modulates ACC activity during fasting via a phosphorylation-independent pathway.

Example 4

TRB3 Directly Interacts COP1

*Drosophila* tribbles (TRB), which shares sequence homology with TRB3, has been found to inhibit certain regulatory targets by promoting their ubiquitination and proteasome-mediated degradation. As demonstrated in this Example, TRB3 directly interacts with the E3 ubiquitin ligase Constitutive Photomorphogenic Protein-1 (COP1).

Figure 3:
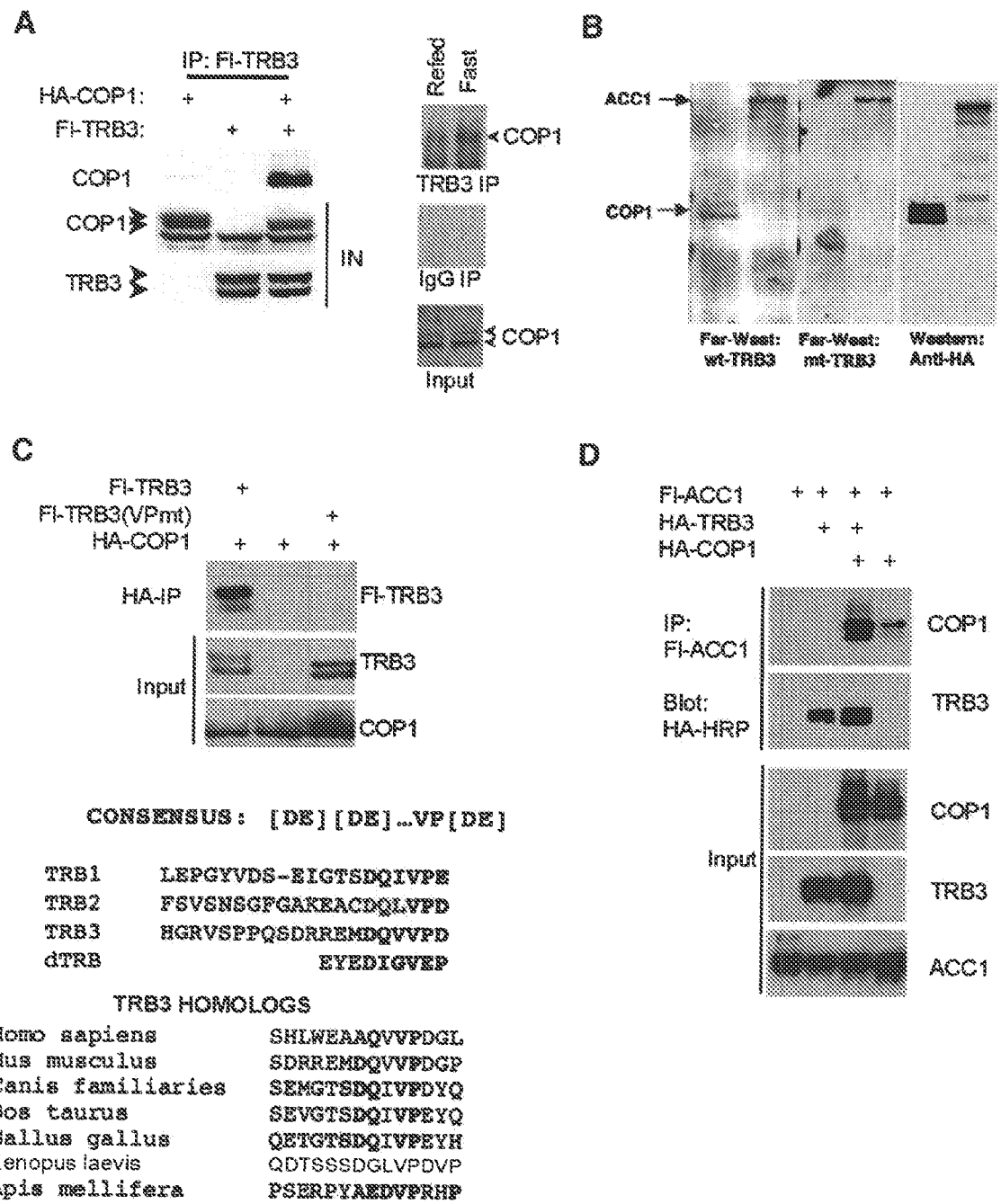
FIG. 3 shows in four panels that TRB3 mediates binding of ACC to the E3 ubiquitin ligase COP1.

In proteomic studies of TRB3 immunoprecipitates prepared from 3T3 L1 adipocytes infected with TRB3 adenovirus, COP1 was recovered (32% coverage), as was De-etiolated-1 (DET1; 14% coverage) and DNA damage binding protein-1 (DDB1; 6% coverage). These proteins are components of a Cul4A ubiquitin ligase complex previously shown to regulate the proteasomal degradation of the mammalian stress-inducible factors c-jun and p53 (Dornan et al., *Nature,* 429:86-92, 2004; Wertz et al., *Science,* 303:1371-4, 2004). Corroborating these results, a strong TRB3:COP1 interaction was observed in co-IP experiments using epitope-tagged polypeptides (FIG. 3A), Endogenous TRB3:COP1 complexes were also detected in WAT from fasted mice and at lower levels in refed mice (FIG. 3A, right).

Example 5

TRB3 Binds Directly to both ACC1 and COP1 Via Distinct Surfaces

This Example illustrates that TRB3 binds directly to both COP1 and ACC. This finding supports the proposed role of TRB3 as an adaptor protein. This Example further shows that a C-terminal truncated TRB3 mutant can bind ACC1 but does not bind COP1. Thus, TRB3 fragments lacking the C-terminus are useful for identifying agents that specifically disrupt the TRB3:ACC1 interaction, and C-terminal TRB3 fragments likely are useful for identifying agents that specifically disrupt the TRB3:COP1 interaction.

To determine whether TRB3 binds to COP1 and ACC via a direct mechanism, Far-Western blotting assays were performed with recombinant GST-TRB3 proteins. Full-length TRB3 was capable of binding directly to both ACC1 and COP1 proteins (FIG. 3B); and a truncated TRB3 polypeptide lacking the C-terminal 40 residues (amino acid residues 315-354) associated with ACC1 but not COP1.

Figure 13:
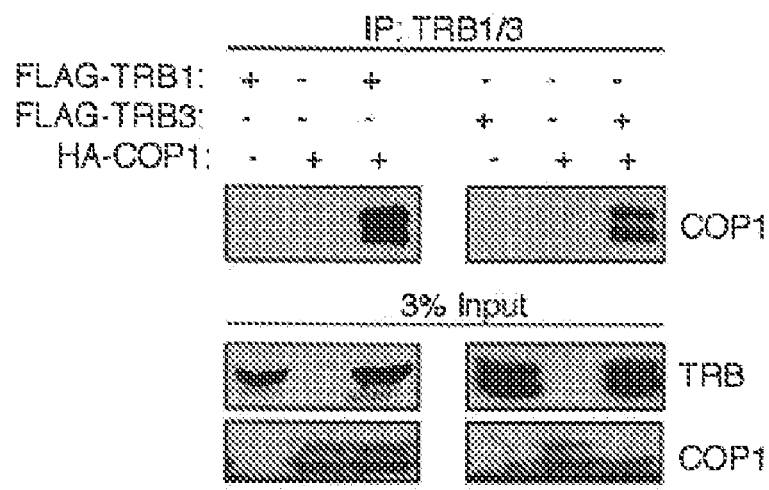
FIG. 13 shows by Western blot assay the recovery of HA-tagged COP1 from immunoprecipitates of Flag-TRB1 ad Flag-TRB3 prepared from HEK293T cells. Input levels of each protein are indicated.

The C-terminal region of TRB3 contains a near-consensus COP1 binding motif (Bianchi et al., *J. Biol. Chem.,* 278: 19682-90, 2003; Holm et al., *Embo J.,* 20:118-27, 2001; Wertz et al., *Science,* 303:1371-4, 2004), which is present in all TRB family members (FIG. 3C). Consistent with this finding, mammalian TRB1 and TRB2 were also found to associate with COP1 (as shown for TRB1 in FIG. 13). Moreover, mutation of TRB3 at key residues in the COP1 binding motif (from EMDQVVPD (residues 331-338 of SEQ ID NO: 2) to AMAQAAD (SEQ ID) NO: 26): VPmt) completely blocked the TRB3:COP1 interaction, but had no effect on TRB3:ACC complex formation (FIG. 3C).

Example 6

TRB3 Mediates COP1-Dependent Ubiquination and Degradation of ACC

Based on its ability to associate with both (COP1 and ACC, apparently via distinct surfaces, TRB3 was expected to (and did) mediate an interaction between these proteins and trigger ACC1 ubiquitination, as demonstrated by this Example.

Figure 4:
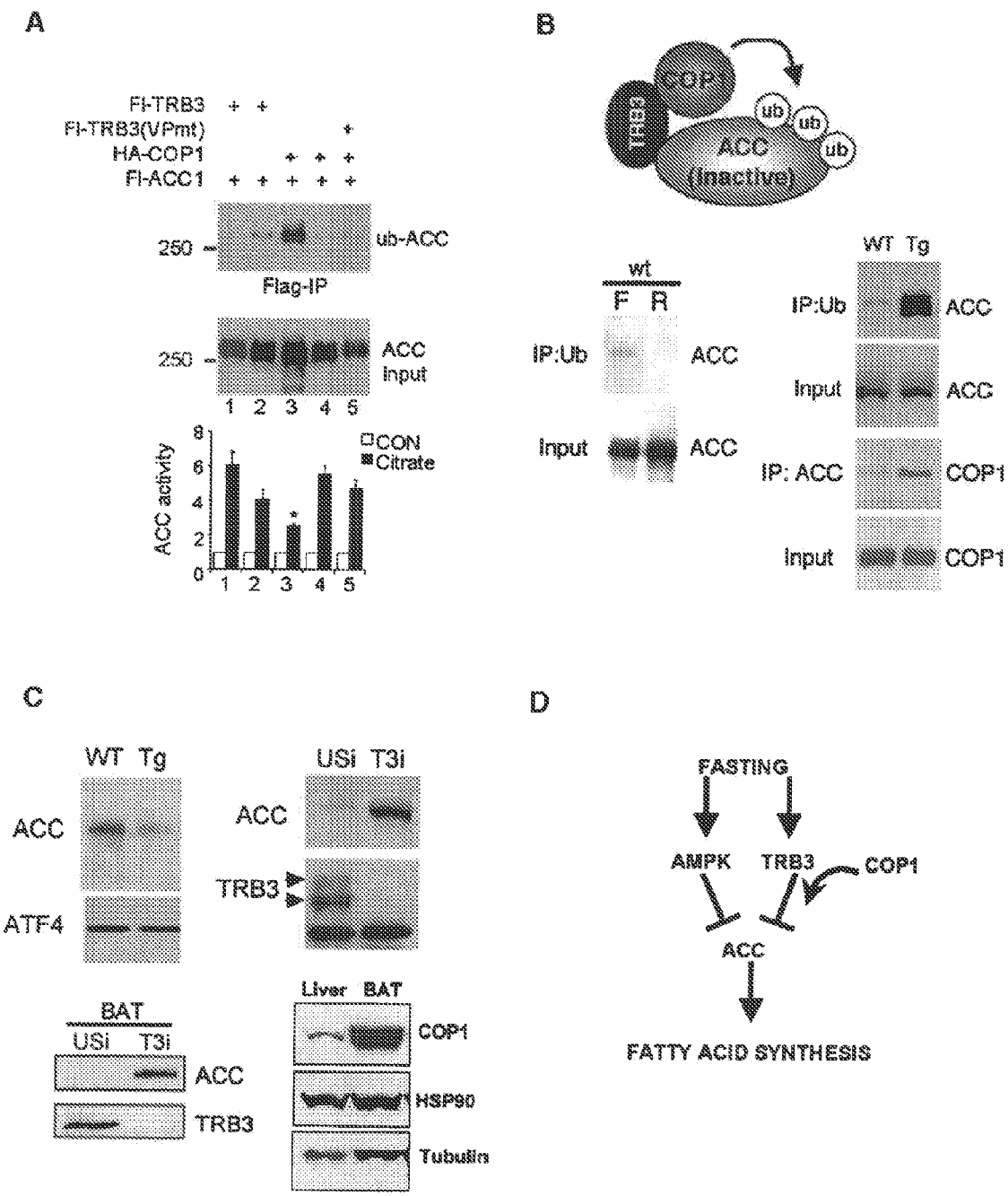
FIG. 4 includes several panels demonstrating that TRB3 mediates the ubiquitination and degradation of ACC by COP1.
Figure 14:
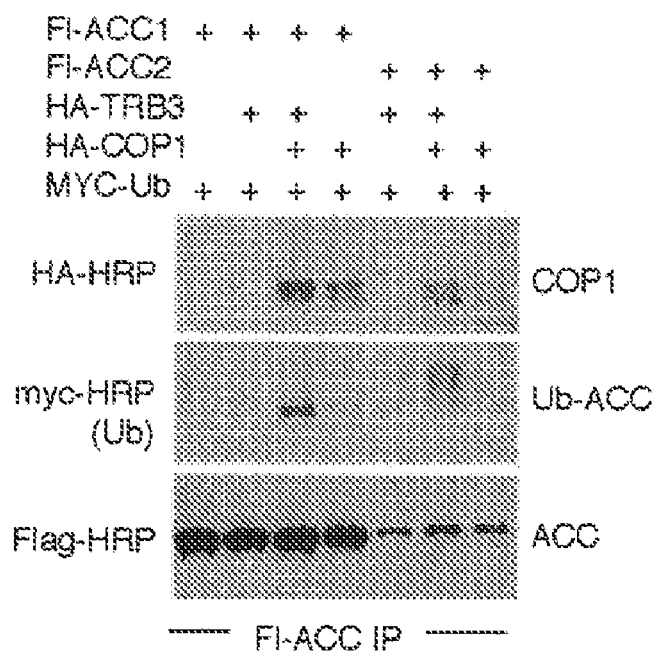
FIG. 14 shows by Western blot assay the amounts of COP1 and ubiquitinated ACC (ub-ACC) recovered from immunoprecipitates of Flag-tagged ACC1 (Fl-ACC1) and ACC2 (Fl-ACC2) prepared from HEK293T cells. Effect of TRB3 expression on levels of COP1 recovered from each immunoprecipitation shown (see lanes with "+" HA-TRB3). Ubiquitination of ACC1 and ACC2 assessed by co-transfection with myc-tagged ubiquitin expression vector (MYC-Ub). Collectively, these results show that TRB3 binds to and promotes COP1 mediated ubiquitination of ACC1 and ACC2.

TRB3 markedly enhanced the interaction of COP1 with ACC1 as well as ACC2 by co-IP assay (FIGS. 3D and 14). Commensurate with these effects TRB3 also stimulated the ubiquitination of ACC1 and ACC2 by COP1 (FIGS. 4A and 14). Confirming the importance of the TRB3 COP1 interaction in this setting, ACC was not ubiquitinated by COP1 in cells expressing VPmt TRB3 protein (FIG. 4A, compare lanes 3 and 4).

TRB3-dependent COP1 ubiquitination of ACC was then shown to be sufficient to inhibit ACC enzymatic activity, Wild-type TRB3 alone reduced ACC1 activity modestly in HEK293T cells, which express low levels of endogenous COP1 relative to 3T3 L1 adipocytes (FIG. 4A, compare lanes 1 and 2). However, ACC activity was reduced about 3-fold in cells co-expressing COP1 and TRB3 (FIG. 4A, lanes 1 and 3). By contrast, VPmt TRB3 had no effect on ACC1 activity in cells co-expressing COP1 (FIG. 4A).

Figure 15:
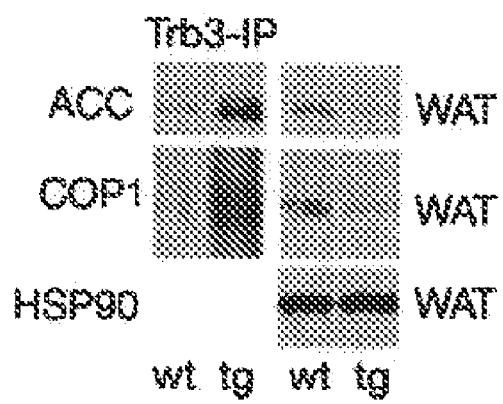
FIG. 15 shows by Western blot amounts of endogenous ACC and COP1 recovered from immunoprecipitations of TRB3 prepared from WAT of wild-type (wt) and F-TRB3 transgenic (tg) mice. HSP90 is shown as loading control.

Taken together, the foregoing results indicate that TRB3 promotes fat burning by mediating the COP1 dependent ubiquitination and inactivation of ACC. This non-limiting model for TRB3 function (see FIG. 4B, top) was further supported by examining the dynamics of ACC ubiquitination in wild-type and F-TRB3 transgenic mice. In keeping with the induction of endogenous TRB3 during fasting, amounts of ubiquitinated ACC in BAT were also higher in fasted compared to refed wild-type mice (FIG. 4B, left). Amounts of ubiquitinated ACC were notably increased in BAT from F-TRB3 mice compared to wild-type littermates (FIG. 4B top right). Further indicative of the role of TRB3 as an adaptor protein, amounts of COP1 associated with ACC in BAT were higher in F-TRB3 mice by Western blot assay of endogenous ACC immunoprecipitates. Conversely, amounts of COP1 and ACC associated with TRB3 were also elevated in adipose from F-TRB3 compared to wild-type littermates (FIG. 15). Taken together, these results demonstrate that TRB3 stimulates ACC ubiquitination in adipose during fasting by mediating its interaction with COP1.

Based on its ability to trigger ACC ubiquitination, TRB3 would be expected to enhance ACC degradation. Indeed, under HFD conditions, total amounts of ACC protein were significantly reduced in WAT and BAT of F-TRB3 mice relative to control littermates (FIG. 4C, top left). Conversely, knockdown of TRB3 with an adenoviral TRB3 siRNA in 3T3-L1 adipocytes induced ACC protein accumulation and enzymatic activity (FIG. 4c, top right, and FIG. 16). Similarly, knockdown of TRB3 in primary cultures of brown adipocytes dramatically increased amounts of ACC protein, confirming the importance of TRB3 in this setting (FIG. 4C, bottom left). Remarkably, COP1 protein levels in BAT are far higher than in other tissues such as liver by Western blot assay, likely explaining in part the distinct metabolic effects of TRB3 in these tissues (FIG. 4C bottom right).

Taken together, this Example demonstrates that TRB3 protects against diet-induced obesity by stimulating fatty acid oxidation in adipose during fasting via the COP1-mediated ubiquitination and degradation of ACC.

Example 7

TRB3 is Ubiquinated and Phosphorylated

Amounts of Flag-TRB3 protein in WAT and BAT of F-TRB3 mice were dramatically elevated (5-10 fold) during fasting relative to feeding. In comparison, mRNA for the F-TRB3 transgene was slightly increased (2-3 fold). The marked induction in amounts of TRB3 protein during fasting in F-TRB3 mice was unexpected, as nutrient and stress signals have been thought to modulate TRB3 expression primarily at the transcriptional level (Du et al., *Science*, 300:1574-1577, 2003), Koo et al., *Nat. Med.*, 10:530-4, 2004, Ord and Ord, *Biochem. Biophys. Res. Commun.*, 330:210-8, 2005). The complete absence of native TRB3 promoter sequences within the F-TRB3 transgene pointed to posttranscriptional control of TRB3 amounts during fasting and feeding.

Exposure of 3T3-L1 cells to the 26S proteasome inhibitor MG132 triggered the rapid accumulation of a slower migrating TRB3 band, suggesting that TRB3 is regulated by proteasomal degradation, with this modified form of TRB3 being targeted preferentially for proteolysis. Amounts of the slower migrating TRB3 band were also increased in 3T3-L1 cells exposed to thapsigargin, an endoplasmic reticulum (ER) stress agonist previously shown to promote expression of TRB3 gene (Ord and Ord, *Biochem. Biophys. Res. Commun.*, 330:210-8, 2005). Accumulation of modified TRB3 was also observed in BAT from TRB3 mice during fasting and in WAT from db/db diabetic mice, suggesting that the normal degradation of modified TRB3 during feeding is blocked during fasting and in insulin resistance. Further supporting this notion, amounts of modified TRB3 were elevated in cultured islet cells with a knockout of the insulin receptor.

Phosphorylation often serves as a targeting signal for degradation of cellular proteins via the 26S proteasome. The following demonstrates that the low mobility TRB3 band corresponds to phosphorylated TRB3 (Gao and Karin, *Mol. Cell.*, 19:581-93, 2005). In two-dimensional phospho-tryptic mapping studies of TRB3 recovered from HEK293T cells labeled with inorganic $^{32}$P, two major spots containing serine were detected by phosphoamino acid analysis. Using deletion mapping and mutagenesis studies, the phosphorylation sites on TRB3 were assigned to two residues corresponding to Ser51 and Ser323. Mutation of both Ser51 and Ser323 to Ala blocked TRB3 phosphorylation in $^{32}$P-labeling experiments and eliminated the slower migrating TRB3 band. Notably, Ser (51,323) Ala mutant protein accumulated to higher levels compared with the wildtype protein in HEK293T cells indicating that phosphorylation at these sites promotes TRB3 degradation.

As with other E3 ubiquitin ligase associated proteins, TRB3 may itself undergo ubiquitination and proteasomal degradation by COP1 complexes. Following treatment with proteasome inhibitor MG132 to permit accumulation of ubiquitinated products, a ladder of ubiquitinated TRB3 polypeptides was observed in cells expressing COP1+DET1. Indeed, MS analysis showed that COP1 promotes ubiquitination of wild-type but not COP1-interaction defective (VPmt) TRB3 at 3 major sites corresponding to Lys33), Lys97, and Lys197. Consistent with these effects, following removal of MG132, COP1+DET1 promoted degradation of wild-type but not VPmt TRB3 protein. TRB3 ubiquitination appeared to be critical in this regard, because a ubiquitination-defective TRB3 mutant (5K/R), containing arginine substitutions at each of the MS-identified (Lys33, Lys97, Lys197) plus two additional sites (Lys184, Lys219) did not undergo proteolysis in response to COP1+DET1. Moreover, a catalytically inactive mutant COP1ΔRING containing alanine substitutions at each of two key residues in the RING finger domain (Cys 136,139) (Wertz et al., *Science*, 303:1371-4, 2004), had no effect on amounts of TRB3 protein in cells co-expressing DET1. Conversely, knockdown of COP1 with COP1 siRNAs (Dornan et al., *Nature*, 429:86-92, 2004) in 3T3-L1 cells promoted accumulation of TRB3 as well as c-jun, another substrate for COP1.

Taken together, this Example illustrates that COP1 is involved not only in TRB3 dependent disruption of ACC1 activity but also in regulating TRB3 protein levels in response to fasting and feeding stimuli.

Example 8

Representative Materials and Methods

This Example provides representative materials and methods useful to obtain the results described in Examples 1-7.

A. Mice

The 5.6 kb aP2 promoter (with mutated Pact site) and 1 kb mouse TRB3 cDNA were cloned into the pWhere vector (Invivogen), flanked by H19insulators. The fragment was released by PacI and purified by phenol-chloroform and ethanol precipitation, and used for pronuclear injection into B6XBalb/c F2 embryos. Offspring (backcrossed twice to C57BL/6) were screened by 3-primer PCR and confirmed by Southern blot. PCR primers for the screening were: wt forward 5'-gagctacacctctggctgct (SEQ ID NO:27); Tg forward 5'-catacagggtctggtcatga (SEQ ID NO:28); R 5'-ggtgtactctgt-gcctgtgg (SEQ ID NO: 29), which gave a 281 pb wt band and 451 bp transgenic band with annealing temperature at 64° C. C57BL/6 and db/db mice were purchased from the Jackson Laboratories and bred in the facility. Mice were fed either normal chow diet (12% fat/60% carbohydrate/28% protein, LabDiet 5001) or high fat diet (HFD) (60% fat/20% carbohydrate/20% protein, Research Diets D12492) and maintained in a pathogen-free facility with 12 hours light/dark cycle. Body weight was measured after weaning as indicated in figures. All mouse protocols were approved by the Institutional Care and Use Committee at the Salk Institute.

B. Fat Cell Size Measurement

H&E stained epididymal WAT sections were photographed at 100× and measured for the pixel size of individual cells using the Photoshop and converted to the cell size (μm). A total of 390 cells from 4 independent mice were measured and plotted using Histogram function in Excel.

C. Cell Lines and Differentiation of 3T3-L1 Pre-Adipocytes

3T3-L1 preadipocytes were infected with TKB3 expressing, TRB3 RNAi, control RNAi, and control GFP lentiviruses. For differentiation of 3T3-L1, two days post confluency (day 0), 3T3-L1 preadipocytes were induced to differentiate in DMEM+10% FBS supplemented with 5 μg/ml insulin, 5 μM dexamethasone, and 1 mM IBMX for two days. The medium was then switched to culture medium supplemented with 5 μg/ml insulin and changed every other day. For adenoviral infections, cells at day 4 of the differentiation regimen were infected with virus, and biochemical studies were performed 2-3 days thereafter. Where indicated, cells were incubated with 10 μM MG132 or 50 nM thapsigargin (Calbiochem) for 1 hour prior to harvest.

D. DNA, Mutagenesis, RNAi and Transfection

Ubiquitin, DDB1, DET1 and COP1 cDNAs were obtained from HEK 293T cell total cDNA, and ACC1 and ACC2 cDNAs were obtained from mouse liver total cDNA by high-fidelity, PCR. Each cDNA was then cloned into the pcDNA3-CMV vector containing myc-, Flag-, or HA-tag Flag-TRB3 was previously described in (Du et al., *Science,* 300:1574-1577, 2003). TRB3-VPmt was generated by alanine substitution mutagenesis of Asp335, Val338, Pro339. Catalytically inactive COP1ΔRING contained alanine substitutions at Cys136 and Cys139 was as previously described by Wertz et al. (*Science,* 303:1371-4, 2004). RNAi oligo sequence for mouse TRB3 was 5'-acttgcactccttagtacg (SEQ ID NO: 30) and for mouse COP1 was 5'-aactgaccaagataacctt (SEQ ID NO: 31) (Dornan et al., *Nature,* 429:86-92, 2004). Negative control siRNA for TRB3 was as previously described by Koo et al. (*Nat. Med.,* 10:530-4, 2004); all RNAi oligos were purchased from Qiagen, HEK 293T cells were transfected using lipofectamine 2000 (Invitrogen) for 20 hours prior to analysis. 3T3-L1 adipocytes differentiated at day 7 were transfected with RNAi oligos for two days followed by re-transfection for an additional day.

E. Metabolic Analysis

Mouse activity, VO2, VCO2, heat production, and RER were measured using metabolic Oxymax V5.61 (Columbus Instruments, Columbus, Ohio). Mice were housed individually, acquainted to the cage for 24 hours to reduce stress and data were collected for the next 24 hours. Food intake was carried out by measuring the weights of food pellets for individually housed mice for 48 hours.

F. RNA Extraction and Q-PCR

Tissue RNA from soleus, liver, WAT and BAT were extracted by Trizol (Invitrogen) and further purified by the RNeasy column (Qiagen) and digested with DNase. For culture cells. RNAs were purified by Qiagen RNeasy column per protocol. After quantification, RNA was normalized to the same concentrations and used in RT-PCR reaction. Q-PCR primers used in this study were:

```
Lcad:
Forward 5' ACATGTGGGAGTACCCGATT    (SEQ ID NO: 32)

Reverse 5' AGAATCCGCATTAGCTGCAT    (SEQ ID NO: 33)

Cpt1:
Forward 5' CATGATCGCAGGAGAAAACA    (SEQ ID NO: 34)

Reverse 5' GGCAGCTGGGGTATCTCTTT    (SEQ ID NO: 35)

vlcad:
Forward 5' ACGGCACAGCATGAGAAAAT    (SEQ ID NO: 36)

Reverse 5' GCATCAGAGAAGGCACATGA    (SEQ ID NO: 37)

ppara:
Forward 5' TCTGTGGGCTCACTGTTCTG    (SEQ ID NO: 38)

Reverse 5' AACTACCTGCTCAGGGCTCA    (SEQ ID NO: 39)

Pgc1a:
Forward 5' CAAGTCTAACTATGCAGACC    (SEQ ID NO: 40)

Reverse 5' ACTTGCTCTTGGTGGAAGCA    (SEQ ID NO: 41)

Ucp1:
Forward 5' GGCCCTTGTAAACAACAAAATAC (SEQ ID NO: 42)

Reverse 5' GGCAACAAGAGCTGACAGTAAAT (SEQ ID NO: 43)

ppard:
Forward 5' CTCTTCATCGCGGCCATCATTCT (SEQ ID NO: 44)

Reverse 5' TCTGCCATCTTCTGCAGCAGCTT (SEQ ID NO: 45)

Ucp2:
Forward 5' GATGGCTTGGCAGTCAAGAA    (SEQ ID NO: 46)

Reverse 5' GAACTCCTGGAACTCGAGTTA   (SEQ ID NO: 47)

adpn:
Forward 5' ATCTGGAGGTGGGAGACCAA    (SEQ ID NO: 48)

Reverse 5' CCAGTAAATGTAGAGTCGTT.   (SEQ ID NO: 49)
```

G. GTT, ITT and Blood Metabolite Measurement

For glucose tolerance test (GTT) or insulin tolerance test (ITT) assays, mice were either fasted for 17 hours or 4 hours, followed by i.p. injection of either 2 g glucose or 1 U insulin per kg of body weight respectively. Glucose was measured at different time points using the One Touch Ultra glucometer Johnson and Johnson). Mouse blood was collected from the tail vein in a heparinized capillary tube. Plasma insulin, leptin and non-esterified free fatty acid levels were measured using commercially available ELISA kits from Mercodia (10115001), Linco (EZML-82K), and WAIK (994-75409), respectively. Plasma triglyceride and β-hydroxybutyrate levels were measured using PTS test strips with a CardioChek analyzer.

H. Measurement of Lipolysis and Fatty Acid Oxidation

The oxidation of oleate derived from triglyceride (TG) hydrolysis was determined by measuring $^3H_2O$ production in 3T3-L1 cells stably transduced with either lentivirus control or lentivirus-TRB3. To measure the oxidation of exogenous oleate, differentiated 3T3-L1 adipocytes were pre-incubated for 12 hours in DMEM containing 0.3 mM oleate (Sigma) bound to 0.5% fatty acid free bovine serum albumin (BSA; Celliance). TG stores were radiolabelled by incubating the cells for 12 hour in DMEM containing 0.3 mM oleate (2.5 μCi/mL, [9,10-$^3$H]) bound to 0.5% fatty acid free BSA. The cells were then washed 4 times with DMEM containing 0.5% BSA and were then incubated for 4 hours in DMEM containing 0.3 mM oleate bowed to 0.5% BSA, and vehicle or 100 μM isoproterenol. The media was collected at 0 hour and 4 hours, and the $^3H_2O$ was extracted from the media samples, as described by Saddik and Lopaschuk (*J. Biol. Chem.,* 266: 8162-70, 1991). At the end of the incubation, the cells were washed, harvested, and sonicated in PBS. Total protein content was then measured. Triglyceride lipolysis was examined as described by Picard et al. (*Cell,* 111:931-41, 2002). Briefly, differentiated 3T3-L1 were starved in DMEM for 4 hours prior to the addition of 10 μM isoproterenol (Sigma) for 1 hour. Glycerol released in the culture media was subsequently measured using GPO-Trinder kit (Sigma).

I. ACC Activity

ACC activity was determined using the standard $H^{14}CO_3^-$ fixation method in the presence of citrate, as described by Witters et al. (*J. Biol. Chem.,* 254:6644-9, 1979). Briefly, 50-100 mg WAT tissues, $10^6$ differentiated 3T3-L1 adipocytes or 293T cells were homogenized in 50-100 μl sucrose buffer (0.25 M sucrose, 1 mM DTT, 1 mM EDTA, phosphatase and protease inhibitors) and ultracentrifuged (for WAT) or microcentrifuged (for 3T3-L1 and 293T cells). The supernatants were adjusted to 2 μg/μl and assayed immediately. A total of 20-30 μg lysate was mixed with assay mixture containing acetyl-CoA (Sigma) and 1.5 μCi NaH$^{14}CO_3$ (MP Biomedicals) in the absence or presence of 2 mM (for 293T cells) or 10 mM (for adipocytes) citrate for 15 minutes at 37° C. The reaction was stopped by addition of 10% perchloric acid (PCA) followed by centrifugation at 6,000 rpm for 20 minutes at 40° C. Supernatant was transferred to glass scintillation vials (VWR) and blow dry, and the radioactivity was counted using the LS6000 liquid scintillation counter (Beckman Coulter).

J. Immunoprecipitation

One day after transfection, cells were washed with PBS and then lysed with lysis buffer (150 mM NaCl, 1% Triton X-100, 1 mM EDTA, 50 mM Tris pH 7.5, protease inhibitors). After preclearing with protein G agarose (Invitrogen) for 30 minutes at 40° C., lysates were incubated with either HA-agarose or Flag-agarose (Sigma) for 1 hour at 40° C. For immunoprecipitation with tissues, WAT lysates were spun at 105,000 g using Optima TLX120 ultracentrifuge for 60 minutes at 40° C. A total of 250-500 µg of lysates were precleared with control serum for 3 hours and protein G agarose for another 2 hours. Precleared lysates were incubated with specific antibodies at 40° C. overnight followed by protein G agarose for 1 hour or with poly-ubiquitin affinity beads (EMD Pharmaceuticals) at 40° C. overnight. The immunoprecipitated beads were extensively washed in lysis buffer, eluted with 2×SDS sample buffer and analyzed with Western blot.

K. Western Blot

Tissues were dissected and snap frozen in liquid nitrogen. WAT were homogenized in sucrose homogenization buffer (0.25 M sucrose, 1 mM DTT, 1 mM EDTA and protease inhibitors) followed by ultracentrifugation. BAT and liver tissues were sonicated in SDS-urea buffer. A total of 10-30 µg lysates were separated by SDS-PAGE and then blotted for the following antibodies specific for: Akt (1:1000, Cell Signaling), p-Ser473 and p-Thr308 Akt (1:1000, Cell Signaling), AMPK (1:1000, Cell Signaling), p-Thr172 AMPK (1:1000, cell Signaling), ACC (1:1000, (cell Signaling), p-Ser79 ACC (1:1000, Cell Signaling), TRB3 (1:5000), FASN (1:1000, Novus Biologicals), COP1 (1:5000, Biomol), HSP90 (1:5000, Santa Cruz), HSL (IgY 1:1000, ProSci), Ub (1:1000, Santa Cruz) followed by the secondary antibodies: goat anti-rabbit IgG HRP (1:10,000, Biorad) or rabbit anti-chicken IgY HRP (1:1000, Upstate). The HRP-conjugated antibodies used were: Flag-HRP (1:7500, Sigma); HA-HRP (1:7500, Santa Cruz), and c-myc-HRP (1:1000, Santa Cruz).

L. Immunohistofluorescence Staining and Microscopy

Staining was carried out essentially as described by Koo et al. (*Nature*, 437:1109-11, 2005), using antibodies against TRB3 (1:600), HA (Santa Cruz, 1:500) or FLAG (1:2000) followed by donkey anti-rabbit FITC (1:200) or donkey anti-mouse Cy3 (1:300, Jackson ImmunoResearchLaboratories), Microscopic images were taken using Nikon immunofluorescence microscope or Leica TCS SP2 AOBS confocal microscope (Leica).

M. Tryptic Digestion and Mapping of Phosphorylation Sites

Tryptic digestion and mapping of phosphorylation sites were carried out essentially as described by Screaton et al. (*Cell*, 119:61-74, 2004).

N. Multidimensional Protein Identification Technology (MudPIT)

The protein digest was pressure loaded onto a fused silica capillary desalting column containing 5 cm of 5 µm Polaris C18-A material (Metachem, Ventura, Calif.) packed into a 250 µm i.d. capillary with a 2 µm filtered union (UpChurch-Scientific Oak Harbor, Wash.). The desalting column washed with buffer containing 95% water, 5% acetonitrile, and 0.9% formic acid. After desalting, a 100 µm i.d. capillary with a 5 µm pulled tip packed with 10 cm 3 µm Aqua C18 material (Phenomenex, Ventura, Calif.) followed by 3 cm 5 µm Partisphere strong cation exchanger (Whatman, Clifton, N.J.) was attached to the filter union and the entire split column (desalting column—filter union—analytical column) was placed inline with an Agilent 1100 quaternary HPLC (Palo Alto, Calif.) and analyzed using a modified 12-step separation as described by Washburn et al. (*Nat. Biotechnol.*, 19:242-7, 2001). The buffer solutions used were 5% acetonitrile/0.1% formic acid (buffer A), 80% acetonitrile/0.1% formic acid (buffer B), and 500 mM ammonium acetate/5% acetonitrile/0.1% formic acid (buffer C). Step 1 consisted of a 100 minute gradient from 0-100% buffer B. Steps 2-11 had the following profile: Three (3) minutes of 100% buffer A, 2 minutes of X % buffer C, a 10 minute gradient from 0-15% buffer B, and a 97 minute gradient from 15-45% buffer B. The 2 minute buffer C percentages (X) were 10, 15, 20, 25, 30, 35, 40, 45, 50, or 60%, respectively for the 12-step analysis. The final step, the gradient contained: Three (3) minutes of 100% buffer A, 20 minutes of 100% buffer C, a 10 minute gradient from 0-15% buffer B, and a 107 minute gradient from 15-70% buffer B. As peptides eluted from the microcapillary column, they were electrosprayed directly into an LTQ 2-dimensional ion trap) mass spectrometer (ThermoFinnigan, Palo Alto, Calif.) with the application of a distal 2.4 kV spray voltage. A cycle of one full-scan mass spectrum (400-1400 m/z) followed by 8 data-dependent MS/MS spectra at a 35% normalized collision energy was repeated continuously throughout each step of the multidimensional separation. Application of mass spectrometer scan functions and HPLC solvent gradients were controlled by the Xcalibur data system.

O. Analysis of Tandem Mass Spectra

MS/MS spectra were analyzed using the following software analysis protocol. Poor quality spectra were removed from the dataset using an automated spectral quality assessment algorithm (Bern et al., *Bioinformatics*, 20(Suppl. 1):I49-I54, 2004). MS/MS spectra remaining after filtering were searched with the SEQUEST™ algorithm against the human-mouse-rat database created by concatenating the three protein databases from EBI current to Apr. 1, 2004. All searches were parallelized and performed on a Beowulf computer cluster consisting of 100 1.2 GHz Athlon CPUs (Sadygov et al., *J. Proteome Res.*, 1:211-5, 2002), No enzyme specificity was considered for any search. SEQUEST™ results were assembled and filtered using the DTASelect (version 2.0) program (Tabb et al., *J. Proteome Res.*, 1:21-26, 2002). DTASelect 2.0 uses a linear discriminant analysis to dynamically set XCorrand DeltaCN thresholds for the entire dataset to achieve a user-specified false positive rate (5% in this analysis). The false positive rates are estimated by the program from the number and quality of spectral matches to the decoy database. The resulting protein list was used to create a subset database to expedite SEQUEST™ differential modification searches. The MS/MS spectra were then re-searched against the subset database to consider modifications of 114 on K to identify, ubiquitination sites or (i) +80 on STY to identify phosphorylation. The MS/MS spectra for the modified peptides were manually evaluated using criteria reported previously (Link et al., *Nat. Biotechnol.*, 17:676-82, 1999). Modified peptide spectra exceeding these criteria were re-searched using SEQUEST™ against the NCBI non-redundant protein database.

P. Statistical Analysis

P values between data sets were determined using two-tailed students' t-test assuming unequal variances.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A method of identifying an agent having potential to mobilize fat stores in a subject, comprising:
   (i) contacting a test system comprising a TRB3 polypeptide with at least one test agent, wherein the test system is selected from a non-human animal, an isolated tissue, an isolated cell or an isolated TRB3 polypeptide;
   (ii) following contact of the at least one test agent with the test system, detecting:
      (a) increased expression of a nucleic acid encoding the TRB3 polypeptide, wherein expression of the nucleic acid encoding the TRB3 polypeptide is increased at least 10% relative to expression of the nucleic acid encoding the TRB3 polypeptide prior to addition of the test agent;
      (b) increased expression of the TRB3 polypeptide, wherein expression of the TRB3 polypeptide is increased at least 10% relative to expression of the TRB3 polypeptide prior to addition of the test agent;
      (c) a posttranslational modification of the TRB3 polypeptide. wherein the posttranslational modification of the TRB3 polypeptide comprises phosphorylation or ubiquitination, and wherein the level of phosphorylation or ubiquitination is increased at least 20% relative to the level of phosphorylation or ubiquitination prior to addition of the agent; and/or
      (d) an enhanced activity of the TRB3 polypeptide, wherein enhanced activity of the TRB3 polypeptide comprises increased formation of TRB3-COP1 complexes, increased formation of TRB3-ACC complexes, or increased TRB3-dependent ACC ubiquitination, and wherein the amount of TRB3-COP1 complexes, TRB3-ACC complexes or TRB3-dependent ACC ubiquitination is increased at least 20% relative to the amount of TRB3-COP1 complexes, TRB3-ACC complexes or TRB3-dependent ACC ubiquitination prior to addition of the test agent; and
   (iii) identifying the at least one test agent as an agent having potential to mobilize fat stores in a subject.

2. The method of claim 1, comprising:
   administering the at least one test agent to a non-human subject having adipocytes comprising the TRB3 polypeptide; and
   detecting in the adipocytes following administration of the at least one test agent:
      (a) increased expression of a nucleic acid encoding the TRB3 polypeptide, wherein expression of the nucleic acid encoding the TRB3 polypeptide is increased at least 10% relative to expression of the nucleic acid encoding the TRB3 polypeptide prior to addition of the test agent;
      (b) increased expression of the TRB3 polypeptide, wherein expression of the TRB3 polypeptide is increased at least 10% relative to expression of the TRB3 polypeptide prior to addition of the test agent;
      (c) a posttranslational modification of the TRB3 polypeptide, wherein the posttranslational modification of the TRB3 polypeptide comprises phosphorylation or ubiquitination, and wherein the level of phosphorylation or ubiquitination is increased at least 20% relative to the level of phosphorylation or ubiquitination prior to addition of the agent; and/or
      (d) an enhanced activity of the TRB3 polypeptide, wherein enhanced activity of the TRB3 polypeptide comprises increased formation of TRB3-COP1 complexes, increased formation of TRB3-ACC complexes, or increased TRB3-dependent ACC ubiquitination, and wherein the amount of TRB3-COP1 complexes, TRB3-ACC complexes or TRB3-dependent ACC ubiquitination is increased at least 20% relative to the amount of TRB3-COP1 complexes, TRB3-ACC complexes or TRB3-dependent ACC ubiquitination prior to addition of the test agent.

3. The method of claim 2, wherein the adipocytes are from brown adipose tissue.

4. The method of claim 2, wherein the adipocytes are from white adipose tissue.

5. The method of claim 1, wherein the test system comprises an isolated cell comprising a TRB3 polypeptide.

6. The method of claim 5, wherein the isolated cell comprises endogenous TRB3 polypeptide.

7. The method of claim 6, wherein the isolated cell is an isolated adipocyte or an adipose cell line.

8. The method of claim 7, wherein the adipose cell line is 3T3-L1, PAZ6, T37i, 3T3-F442A, or HIB-1B.

9. The method of claim 5, wherein the isolated cell comprises exogenous TRB3 polypeptide.

10. The method of claim 9, wherein the isolated cell has substantially no endogenous TRB3 polypeptide.

11. The method of claim 5, wherein the isolated cell has been stably or transiently transfected with an expression vector encoding the TRB3 polypeptide.

12. The method of claim 5, wherein the isolated cell has been stably or transiently transfected with one or more expression vectors encoding the TRB3 polypeptide and one or both of a COP1 polypeptide and/or an ACC polypeptide.

13. The method of claim 12, wherein the ACC polypeptide is ACC1 or ACC2.

14. The method of claim 1, comprising contacting with the at least one test agent an isolated TRB3 polypeptide and detecting following contact with the at least one test agent an enhanced activity of the TRB3 polypeptide.

15. The method of claim 14, further comprising contacting the at least one test agent and the isolated TRB3 polypeptide with one or both of a COP1 polypeptide and/or an ACC polypeptide, and detecting following contact with the at least one test agent increased formation of TRB3-COP1 complexes, and/or increased formation of TRB3-ACC complexes.

16. The method of claim 1, wherein the at least one test agent is one or more of natural products, chemical compositions, biochemical compositions, polypeptides, peptides, or antibodies.

17. The method of claim 1, wherein the nucleic acid encoding the TRB3 polypeptide is a TRB3 mRNA.

* * * * *